(12) United States Patent
Kassab et al.

(10) Patent No.: US 10,892,067 B2
(45) Date of Patent: Jan. 12, 2021

(54) DEVICES AND SYSTEMS FOR OBTAINING CONDUCTANCE DATA AND METHODS OF MANUFACTURING AND USING THE SAME

(71) Applicant: 3DT Holdings, LLC, San Diego, CA (US)

(72) Inventors: Ghassan S. Kassab, La Jolla, CA (US); Mark Svendsen, Indianapolis, IN (US); William Combs, Galena, OH (US); Kevin Mauser, Indianapolis, IN (US); John Browder, Shelbyville, IN (US); Lynette Peters, Maineville, OH (US)

(73) Assignee: 3DT Holdings, LLC, San Diego, CA (US)

( * ) Notice: Subject to any disclaimer, the term of this patent is extended or adjusted under 35 U.S.C. 154(b) by 567 days.

(21) Appl. No.: 15/677,296

(22) Filed: Aug. 15, 2017

(65) Prior Publication Data
US 2018/0061524 A1    Mar. 1, 2018

Related U.S. Application Data

(62) Division of application No. 13/646,129, filed on Oct. 5, 2012, now Pat. No. 9,734,938.
(Continued)

(51) Int. Cl.
*H01B 7/04*    (2006.01)
*A61B 5/053*   (2006.01)
(Continued)

(52) U.S. Cl.
CPC .......... *H01B 7/048* (2013.01); *A61B 5/0538* (2013.01); *A61B 5/01* (2013.01); *A61B 5/6851* (2013.01);
(Continued)

(58) Field of Classification Search
CPC ............... A61B 5/0538; A61B 5/6851; A61B 2562/222; A61B 5/01; A61M 25/09; A61M 2025/09191; H01B 7/048
See application file for complete search history.

(56) References Cited

U.S. PATENT DOCUMENTS

| | | |
|---|---|---|
| 3,896,373 A | 7/1975 | Zelby |
| 4,380,237 A | 4/1983 | Newbower |

(Continued)

FOREIGN PATENT DOCUMENTS

| | | |
|---|---|---|
| EP | 1 025 805 A1 | 8/2000 |
| JP | 2006334198 A | 12/2006 |

(Continued)

OTHER PUBLICATIONS

International Searching Authority, International Search Report, dated Aug. 16, 2012 (PCT/US2011/023911).
(Continued)

*Primary Examiner* — Sean P Dougherty
(74) *Attorney, Agent, or Firm* — Reichel Stohry Dean LLP; Mark C. Reichel; Natalie J. Dean

(57) ABSTRACT

Devices and systems for obtaining conductance data and methods of manufacturing and using the same. In at least one embodiment of a device of the present disclosure, the device is an elongated body with at least one groove defined therein, the at least one groove configured to receive one or more conductor wires therein. In another embodiment, the device is an elongated core body having a plurality of conductive elements positioned thereon and a coating to result in a device having an overall round-cross section.

17 Claims, 33 Drawing Sheets

Related U.S. Application Data

(60) Provisional application No. 61/644,685, filed on May 9, 2012, provisional application No. 61/585,535, filed on Jan. 11, 2012, provisional application No. 61/543,899, filed on Oct. 6, 2011.

(51) Int. Cl.
   *A61B 5/01* (2006.01)
   *A61B 5/00* (2006.01)
   *A61M 25/09* (2006.01)

(52) U.S. Cl.
   CPC ........ *A61B 2562/222* (2013.01); *A61M 25/09* (2013.01); *A61M 2025/09191* (2013.01)

(56) References Cited

U.S. PATENT DOCUMENTS

| | | |
|---|---|---|
| 4,457,973 A | 7/1984 | Matsui |
| 4,587,975 A | 5/1986 | Salo et al. |
| 4,840,182 A | 6/1989 | Carlson |
| 4,840,186 A * | 6/1989 | Lekholm ................ A61N 1/056 607/116 |
| 4,873,987 A | 10/1989 | Djordjevich et al. |
| 4,957,110 A | 9/1990 | Vogel et al. |
| 5,058,583 A | 10/1991 | Geddes et al. |
| 5,125,410 A | 6/1992 | Misono et al. |
| 5,233,994 A | 8/1993 | Shmulewitz |
| 5,303,704 A * | 4/1994 | Molacek ............ A61B 5/0422 600/377 |
| 5,366,443 A | 11/1994 | Eggers et al. |
| 5,453,576 A | 9/1995 | Krivitski |
| 5,665,103 A | 9/1997 | Lafontaine et al. |
| 5,827,192 A | 10/1998 | Gopakumaran et al. |
| 5,842,998 A | 12/1998 | Gopakumaran et al. |
| 5,935,159 A | 8/1999 | Cross, Jr. |
| 5,971,933 A | 10/1999 | Schluter |
| 6,112,115 A | 8/2000 | Feldman et al. |
| 6,113,557 A | 9/2000 | Fagan |
| 6,165,977 A | 12/2000 | Mochly-Rosen |
| 6,187,744 B1 | 2/2001 | Rooney |
| 6,191,136 B1 | 2/2001 | Marban |
| 6,270,493 B1 | 8/2001 | Lalonde et al. |
| 6,296,615 B1 | 10/2001 | Brockway et al. |
| 6,325,762 B1 | 12/2001 | Tjin |
| 6,354,999 B1 | 3/2002 | Dgany et al. |
| 6,360,123 B1 | 3/2002 | Kimchi et al. |
| 6,398,738 B1 | 6/2002 | Millar |
| 6,411,760 B1 | 6/2002 | Avellanet |
| 6,471,656 B1 | 10/2002 | Shalman et al. |
| 6,494,832 B1 | 12/2002 | Feldman et al. |
| 6,501,991 B1 * | 12/2002 | Honeck ................ A61N 1/056 607/122 |
| 6,511,413 B2 | 1/2003 | Landesberg |
| 6,545,678 B1 | 4/2003 | Ohazama |
| 6,569,862 B1 | 5/2003 | Marban |
| 6,663,661 B2 | 12/2003 | Boneau |
| 6,666,828 B2 | 12/2003 | Greco et al. |
| 6,925,334 B1 * | 8/2005 | Salys ..................... A61N 1/056 600/374 |
| 6,926,674 B2 | 8/2005 | Tenerz et al. |
| 6,939,313 B2 | 9/2005 | Saadat |
| 7,069,072 B2 | 6/2006 | Jansen et al. |
| 7,141,019 B2 | 11/2006 | Pearlman |
| 7,169,107 B2 | 1/2007 | Jersey-Willuhn et al. |
| 7,189,208 B1 | 3/2007 | Beatty et al. |
| 7,236,820 B2 | 6/2007 | Mabary et al. |
| 7,311,702 B2 | 12/2007 | Tallarida et al. |
| 7,326,241 B2 | 2/2008 | Jang |
| 7,877,151 B2 * | 1/2011 | Wengreen ............ A61N 1/056 607/122 |
| 8,099,161 B2 | 1/2012 | Kassab |
| 8,114,143 B2 | 2/2012 | Kassab et al. |
| 8,185,194 B2 | 5/2012 | Kassab |
| 8,437,864 B2 * | 5/2013 | Seifert ................ A61N 1/0563 607/116 |
| 8,849,415 B2 * | 9/2014 | Bedenbaugh .......... H01R 4/363 607/115 |
| 9,084,883 B2 * | 7/2015 | Scheuermann ........ A61N 1/056 |
| 9,186,209 B2 * | 11/2015 | Weber ................ A61N 1/0551 |
| 2002/0049488 A1 | 4/2002 | Boneau |
| 2002/0088931 A1 * | 7/2002 | Danisch ................ G01D 5/268 250/227.14 |
| 2003/0088187 A1 | 5/2003 | Saadat |
| 2004/0019318 A1 | 1/2004 | Wilson |
| 2004/0024329 A1 | 2/2004 | Jansen et al. |
| 2004/0054301 A1 | 3/2004 | Cassell |
| 2004/0097965 A1 * | 5/2004 | Gardeski .......... A61M 25/0021 606/129 |
| 2004/0116816 A1 | 6/2004 | Tenerz et al. |
| 2004/0230131 A1 | 11/2004 | Kassab |
| 2004/0254495 A1 | 12/2004 | Mabary et al. |
| 2005/0054905 A1 | 3/2005 | Corl |
| 2006/0074318 A1 | 4/2006 | Ahmed |
| 2006/0235314 A1 * | 10/2006 | Migliuolo ............ A61B 1/0011 600/505 |
| 2007/0161914 A1 | 7/2007 | Zdeblick et al. |
| 2007/0241975 A1 | 10/2007 | Kimoto |
| 2007/0299366 A1 | 12/2007 | Sharrow |
| 2008/0047732 A1 | 2/2008 | Park |
| 2008/0176271 A1 | 7/2008 | Silver et al. |
| 2008/0194991 A1 | 8/2008 | Teague |
| 2008/0194996 A1 | 8/2008 | Kassab |
| 2008/0269581 A1 | 10/2008 | Wood et al. |
| 2009/0069709 A1 | 3/2009 | Schmitz |
| 2009/0216133 A1 | 8/2009 | Kassab |
| 2010/0030098 A1 | 2/2010 | Fojtik |
| 2010/0041984 A1 | 2/2010 | Shapland et al. |
| 2010/0228202 A1 * | 9/2010 | O'Dea ............ A61M 25/0013 604/264 |
| 2011/0224720 A1 * | 9/2011 | Kassab ............ A61B 17/00491 606/213 |
| 2014/0236126 A1 | 8/2014 | Lupton |
| 2015/0032027 A1 * | 1/2015 | Lupton ................ A61B 5/6851 600/585 |
| 2018/0019039 A1 * | 1/2018 | Kassab ................ A61B 5/0538 |

FOREIGN PATENT DOCUMENTS

| WO | WO 98/35611 | 8/1998 |
| WO | WO 02/19905 | 3/2002 |
| WO | WO 02/085442 | 10/2002 |
| WO | WO 03/092495 A1 | 11/2003 |

OTHER PUBLICATIONS

International Searching Authority, Written opinion of the International Searching Authority, dated Aug. 16, 2012 (PCT/US2011/023911).

International Searching Authority, International Search Report, dated Aug. 30, 2012 (PCT/US2011/024961).

International Searching Authority, Written opinion of the International Searching Authority, dated Aug. 30, 2012 (PCT/US2011/024961).

International Searching Authority, International Search Report, dated Sep. 7, 2012 (PCT/US2011/026337).

International Searching Authority, Written opinion of the International Searching Authority, dated Sep. 7, 2012 (PCT/US2011/026337).

International Searching Authority, International Search Report, dated Jul. 6. 2005 (PCT/US2004/04828).

International Searching Authority, Written opinion of the International Searching Authority, dated Jul. 6, 2005 (PCT/US2004/04828).

International Searching Authority, International Search Report, dated Aug. 8, 2007 (PCT/US2006/05985).

International Searching Authority, Written opinion of the International Searching Authority, dated Aug. 8, 2007 (PCT/US2006/05985).

(56) References Cited

OTHER PUBLICATIONS

Supplementary European Search Report for EP Application Serial No. 04 71 2383 to Electro-Cat, LLC, dated Aug. 3, 2007.

Hoekstein and Inbar, "Cardiac Stroke Volume Estimation . . . " Technion Department of Electrical Engineering Publication EE PUB No. 991; Feb. 1994.

L. Kornet, et al. "Conductance Method for the Measurement of . . . " Annals of Biomedical Engineering, vol. 27. pp. 141-150, 1999.

Douglas A. Hettrick, et al. "Finite Element Model Determination of . . . " Annals of Biomedical Engineering. vol. 27, pp. 151-159, 1999.

Douglas A. Hettrick, et al. "In Vivo Measurement of Real-Time Aortic Segmental Volume . . . " Annals of Biomedical Engineering. vol. 26, pp. 431-440, 1998.

\* cited by examiner

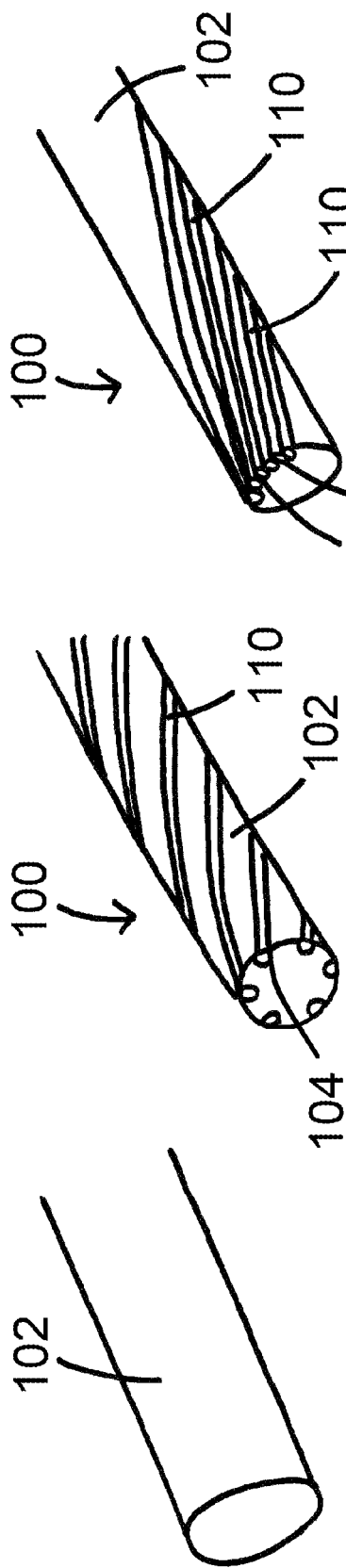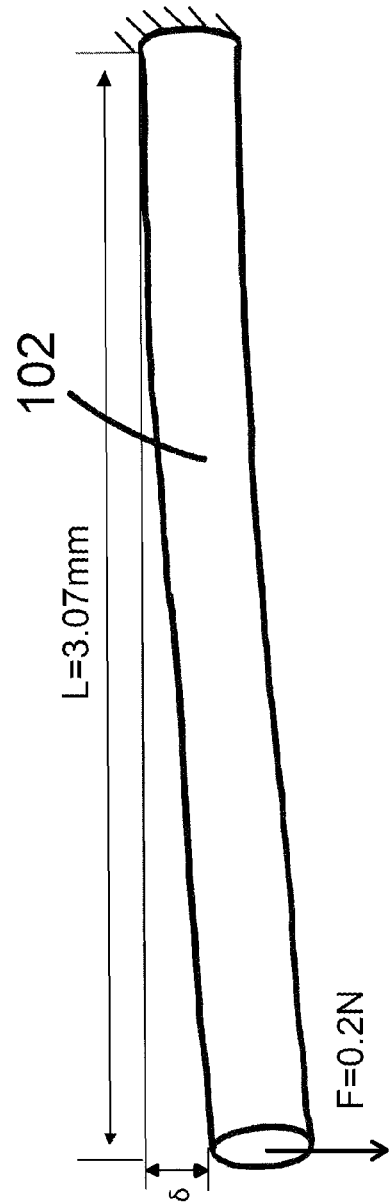

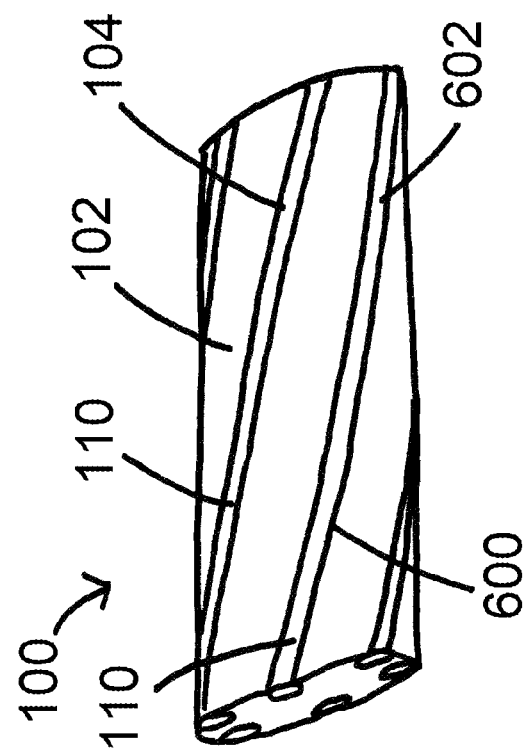
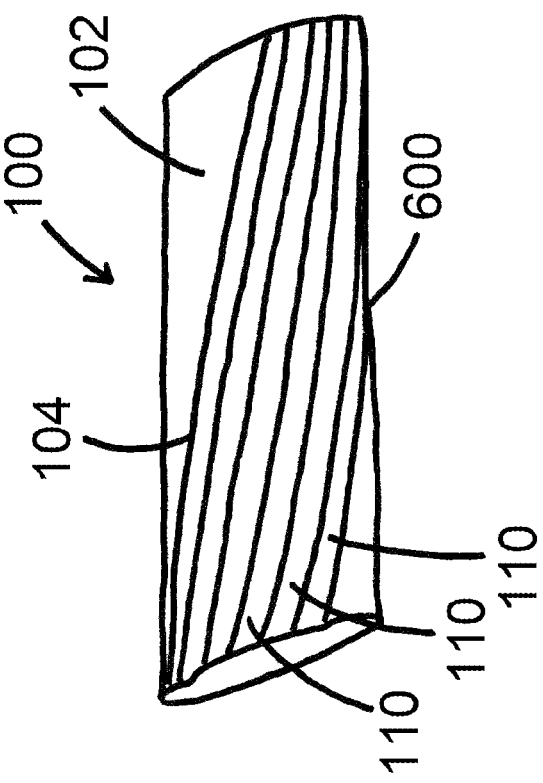
FIG. 6A
FIG. 6B

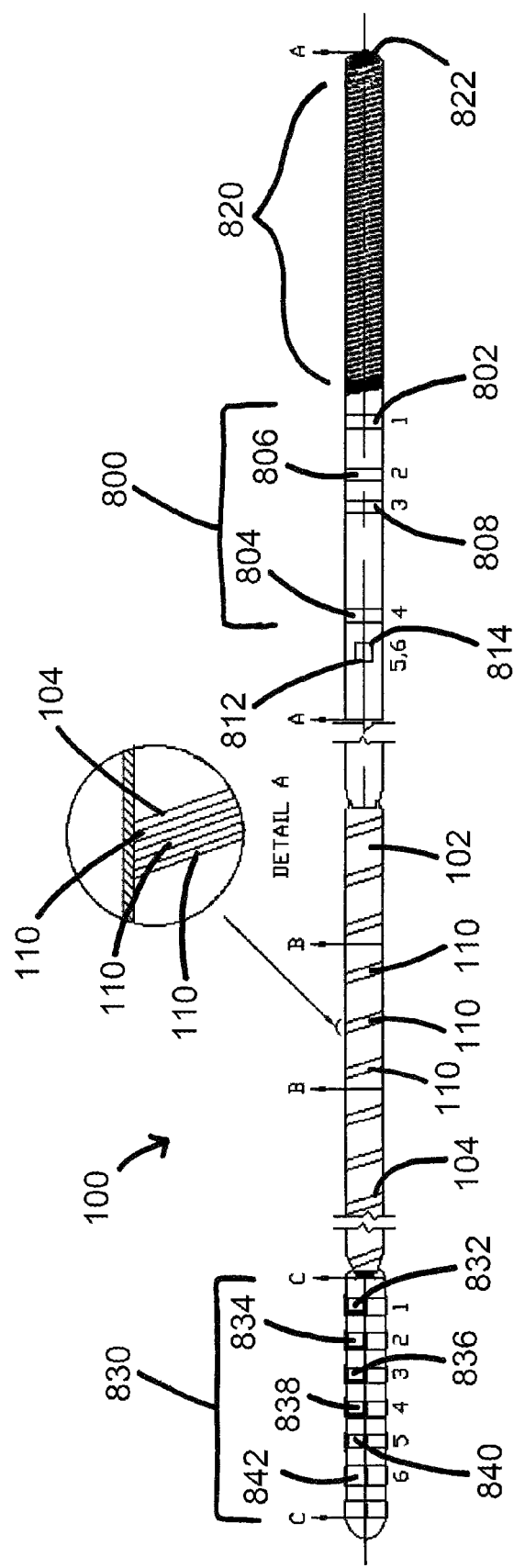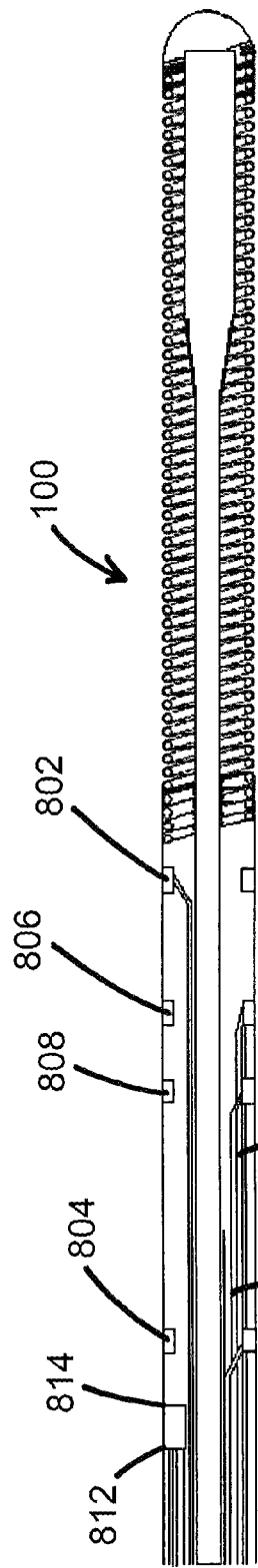
FIG. 8A
FIG. 8B

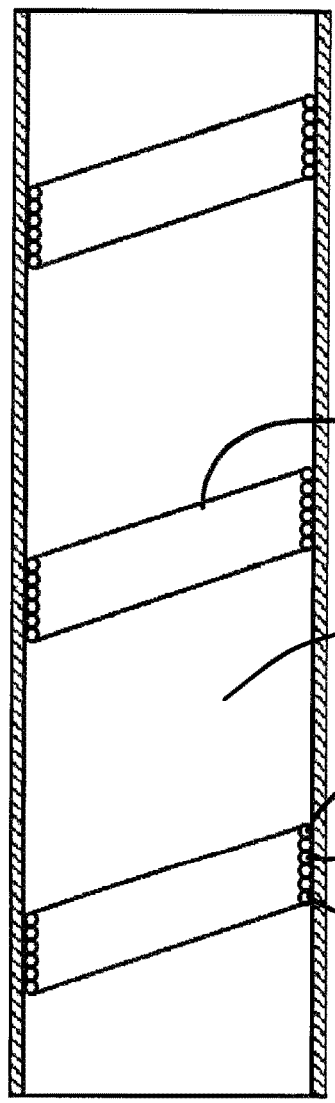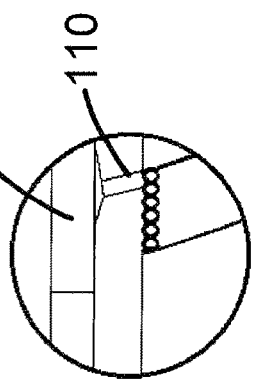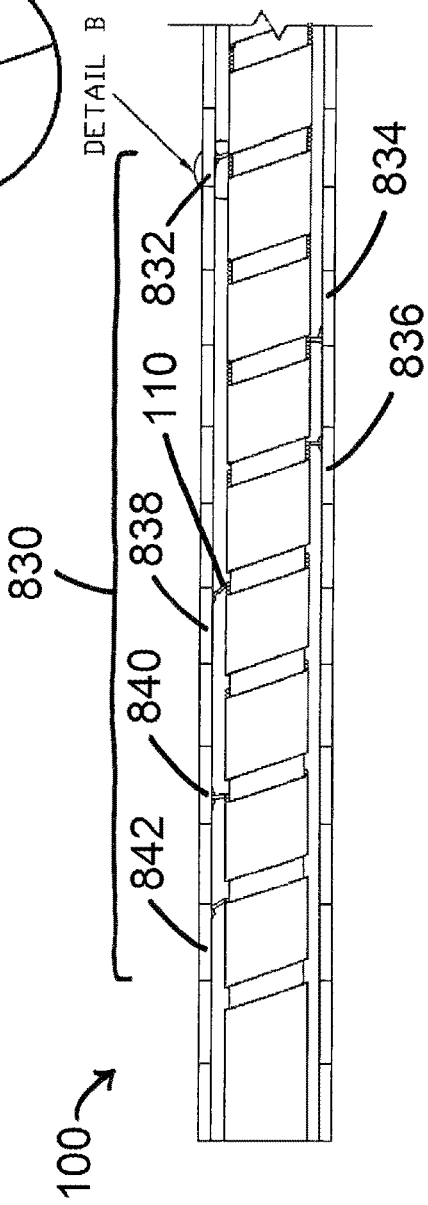
FIG. 9A
FIG. 9B

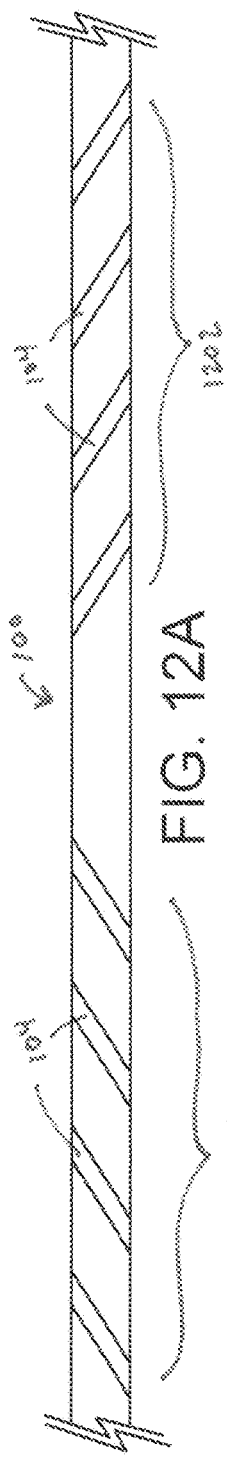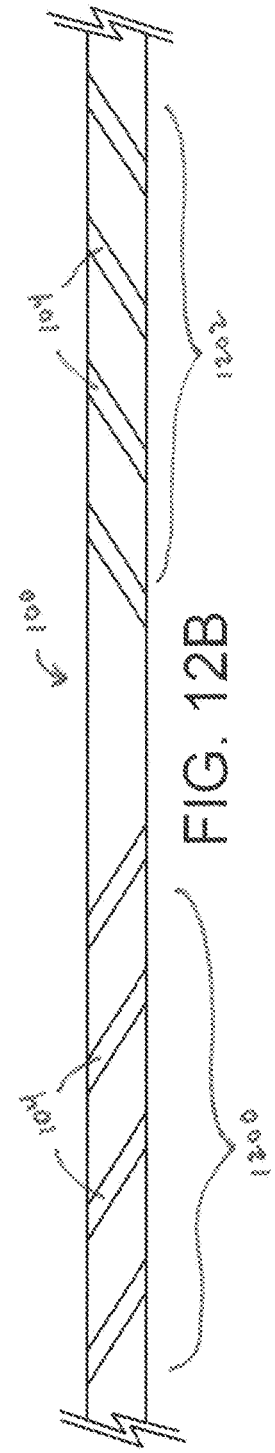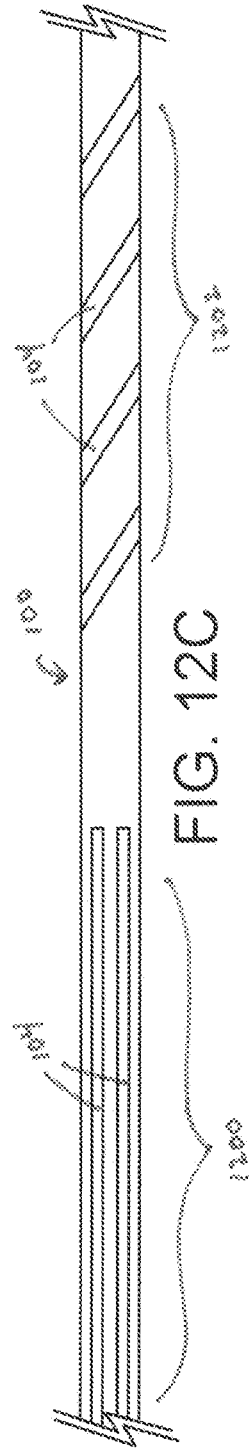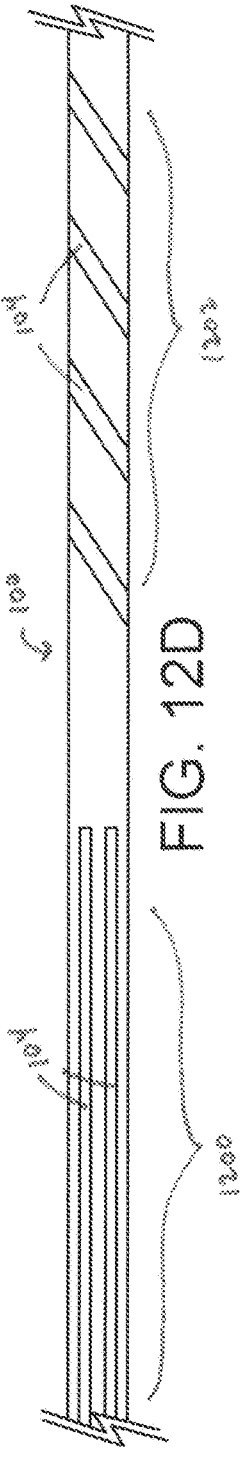

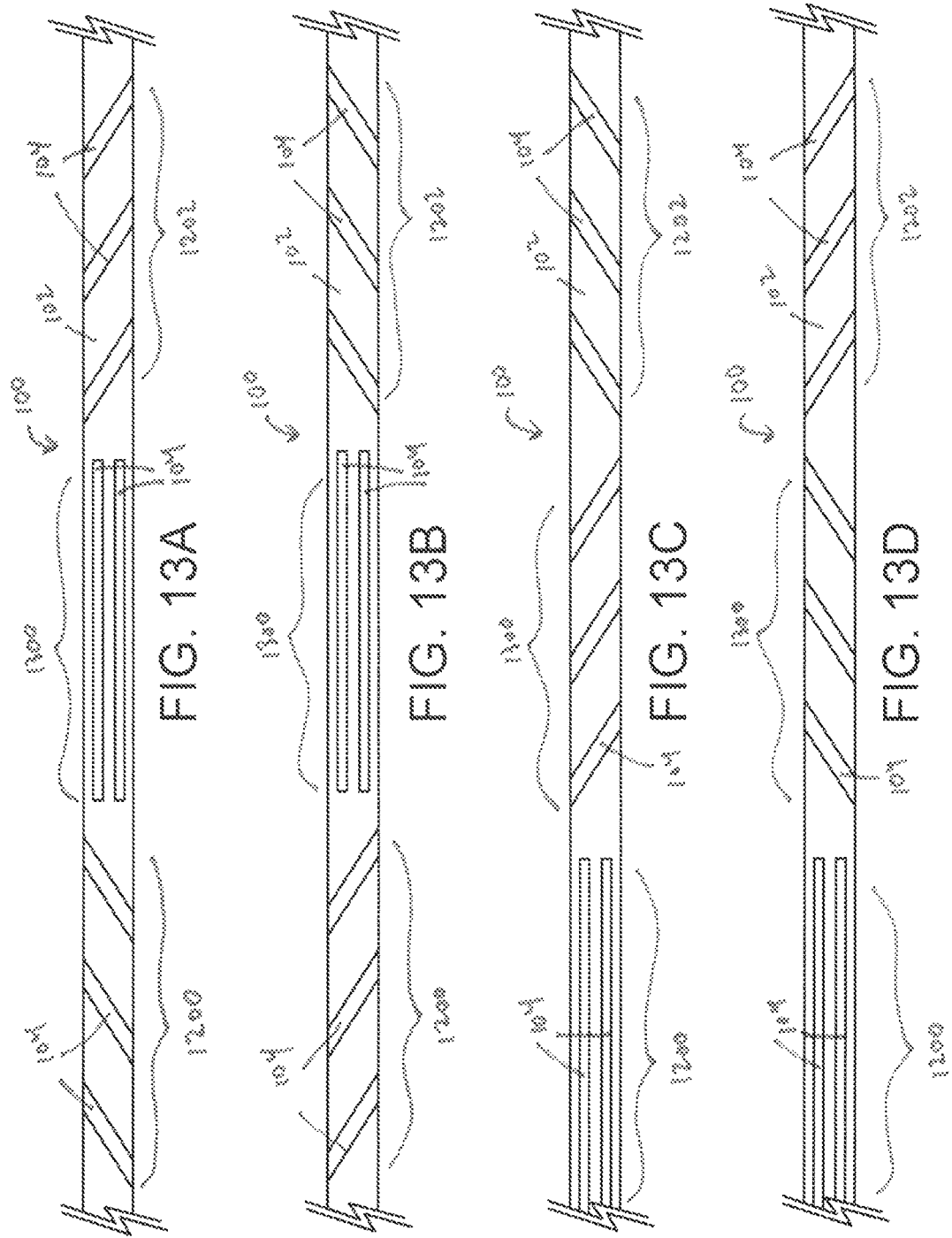

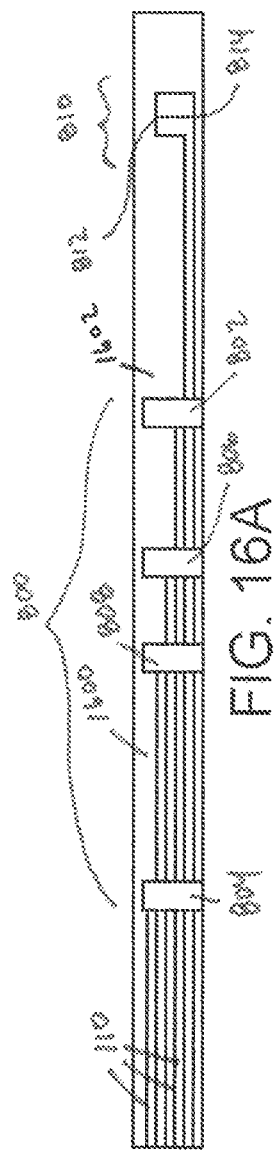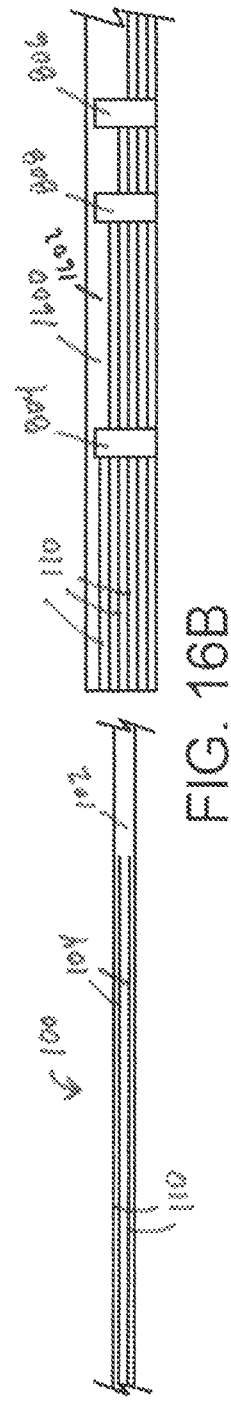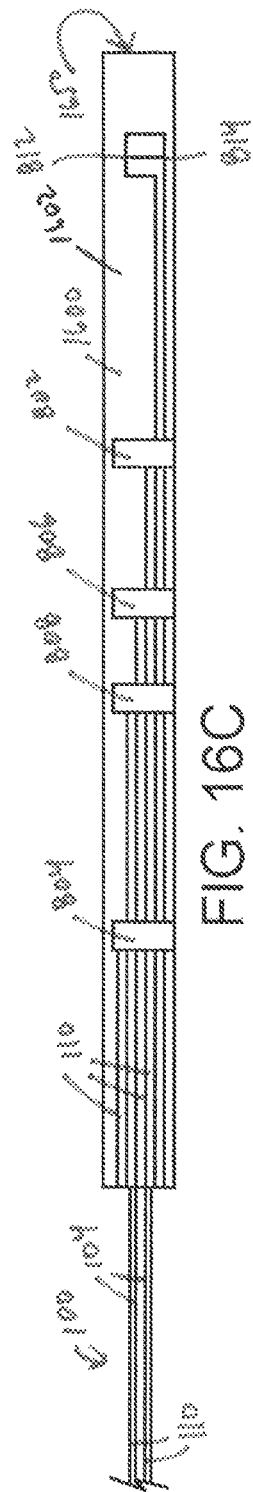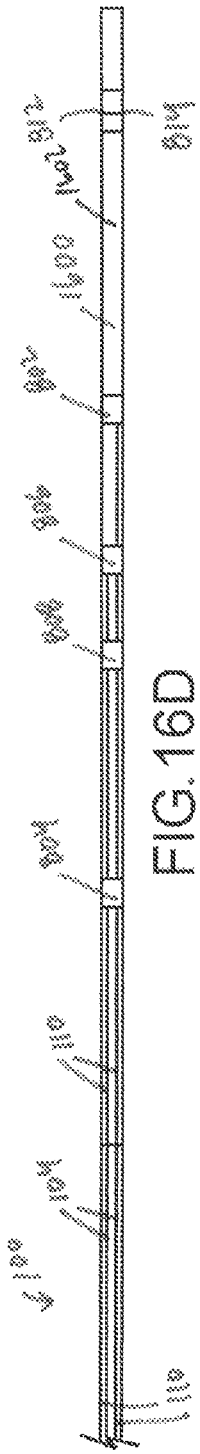

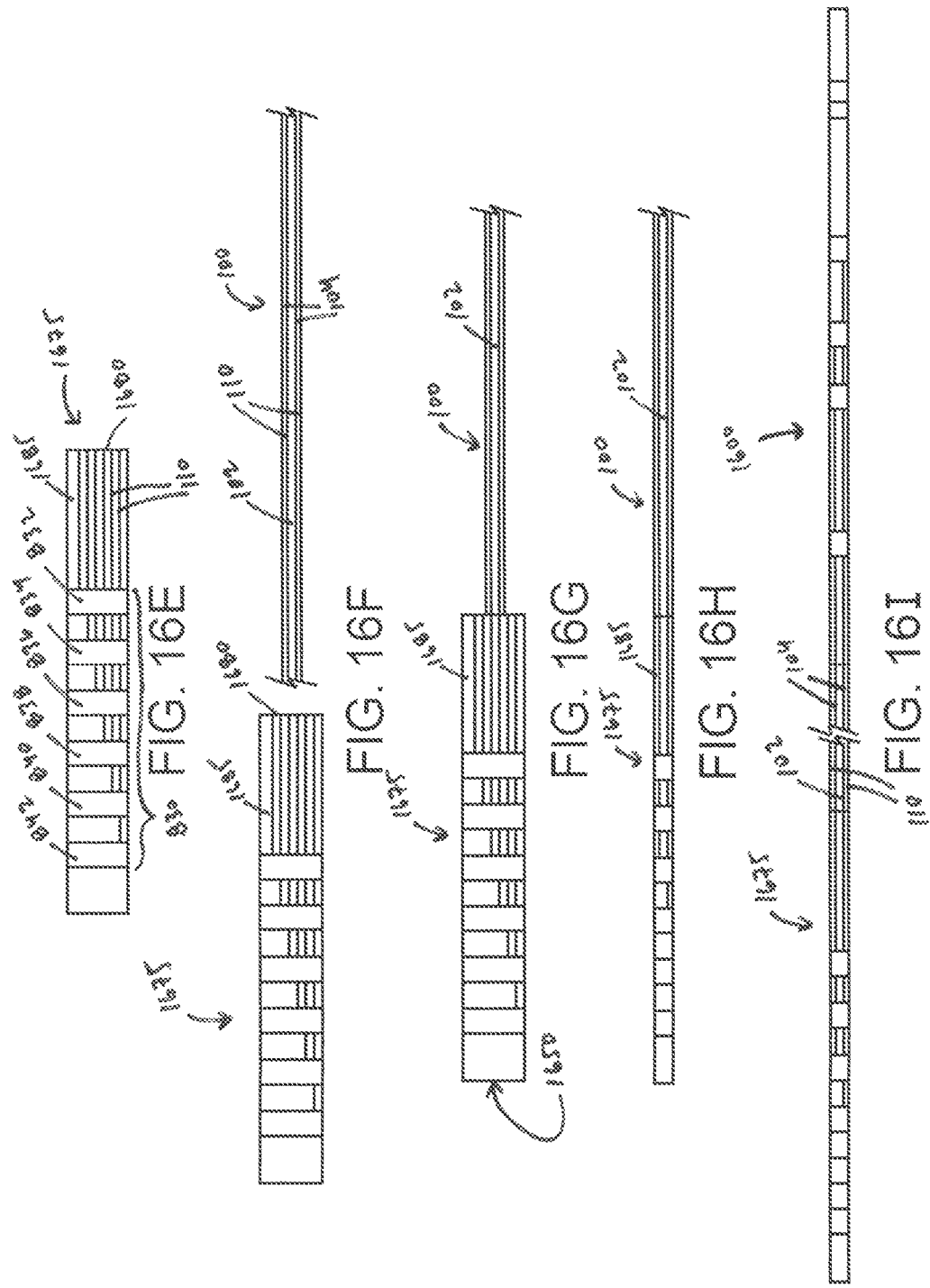

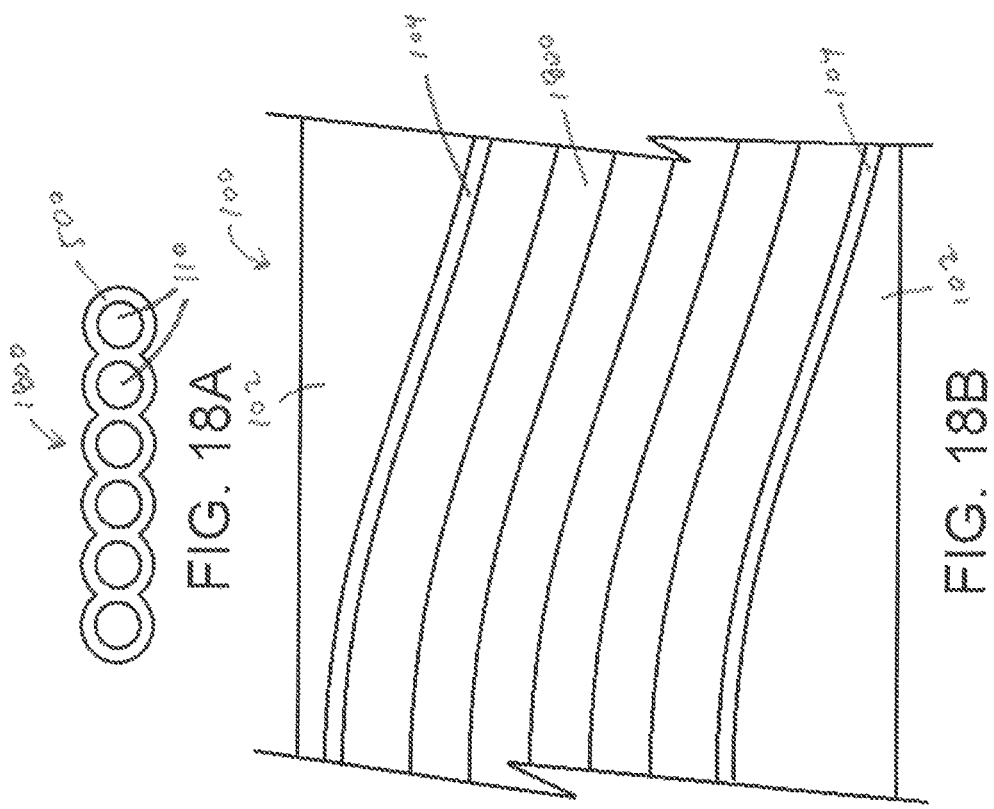

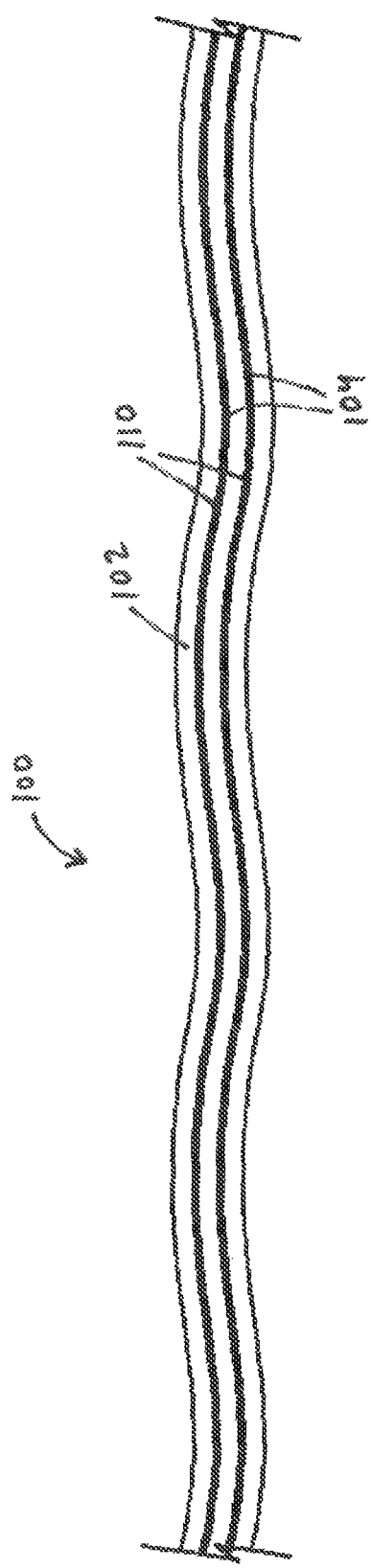

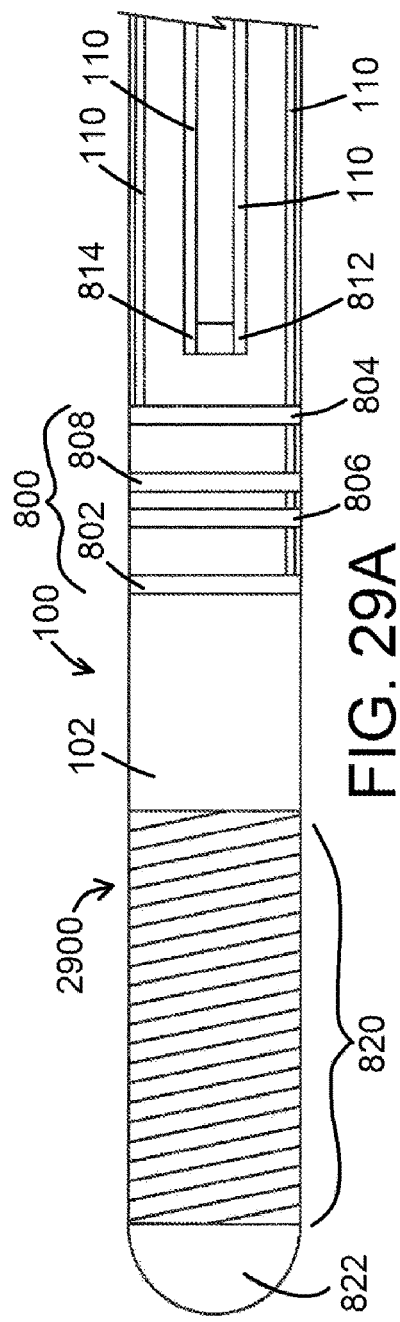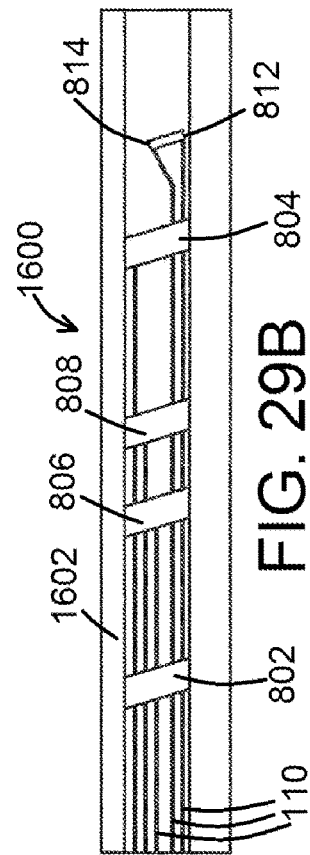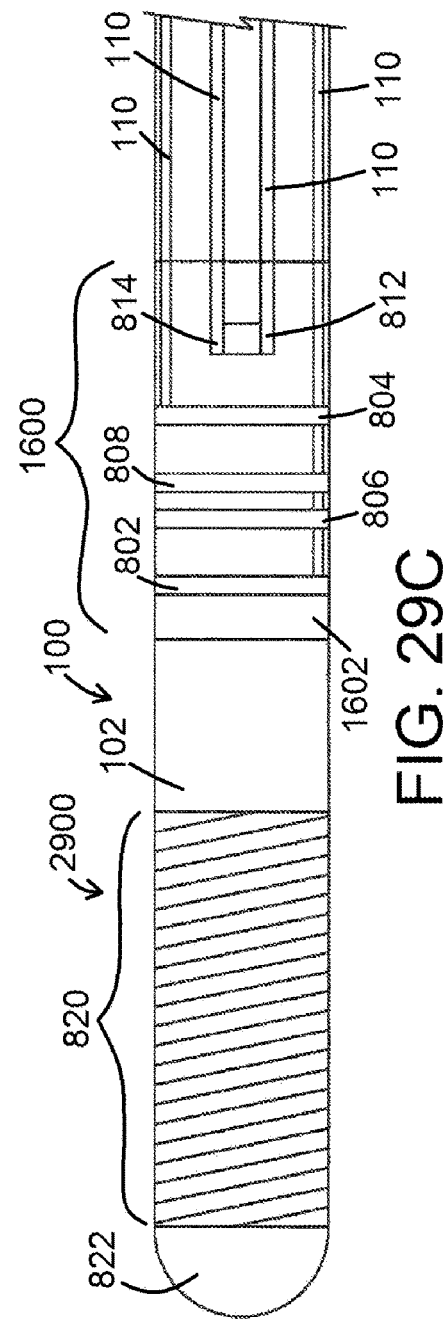

DEVICES AND SYSTEMS FOR OBTAINING CONDUCTANCE DATA AND METHODS OF MANUFACTURING AND USING THE SAME

PRIORITY

The present application is related to, claims the priority benefit of, and is a divisional patent application of, U.S. Nonprovisional patent application Ser. No. 13/646,129, filed Oct. 5, 2012 and issued as U.S. Pat. No. 9,734,938 on Aug. 15, 2017, which is related to, and claims the priority benefit of, U.S. Provisional Patent Application Ser. No. 61/543,899, filed Oct. 6, 2011, U.S. Provisional Patent Application Ser. No. 61/585,535, filed Jan. 11, 2012, and U.S. Provisional Patent Application Ser. No. 61/644,685, filed May 9, 2012. The contents of each of the foregoing are incorporated by reference in their entirety into this disclosure.

BACKGROUND

In the medical arts, various medical devices are required to be effective, durable, and small or compact so to meet the particular needs of physicians and/or other interventionalists. Conductive devices, which can be catheters, wires, and the like, having various electrodes thereon or therein need to be particularly compact so to fit within narrow bodily lumens like a patient's vasculature and various other luminal organs, such as the heart.

Wires may be preferred over catheters due to their relatively smaller size and the ability to fit one or more wires within a catheter lumen, for example. However, given the size of a typical guidewire (0.014" or 0.035" in diameter, for example), conductive wire placement along the guidewire having those dimensions typically increases the overall cross-sectional area of the guidewire, making the guidewire unsuitable for certain applications.

Accordingly, a compact device useful to carry various conductive wires and sensors, configured for various interventional uses within a patient's body, would be well received in the marketplace.

BRIEF SUMMARY

In at least one embodiment of a device of the present disclosure, the device comprises an elongated body with at least one groove defined therein, wherein the at least one groove can be one groove, two grooves, three grooves, or four or more grooves, the at least one groove configured to receive one or more conductor wires therein. In various embodiments, the elongated body has an outer diameter between approximately 0.010" and approximately 0.050." In another embodiment, the elongated body has an outer diameter selected from the group consisting of approximately 0.014" and 0.035". In yet another embodiment, the at least one groove has a depth of approximately 0.003".

In at least one embodiment of a device of the present disclosure, the at least one groove has a width between approximately 0.003" and approximately 0.020". In an additional embodiment, the at least one groove has a width selected from the group consisting of approximately 0.003" and approximately 0.018". In yet an additional embodiment, the at least one groove is sized and shaped to receive at least four conductor wires therein. In another embodiment, the at least one groove is sized and shaped to receive at least six conductor wires therein.

In at least one embodiment of a device of the present disclosure, the at least one groove comprises one groove, and the at least one conductor wire comprises six wires. In another embodiment, the at least one groove comprises six grooves, and the at least one conductor wire comprises six wires. In yet another embodiment, the device further comprises the at least one conductor wire positioned within the at least one groove. In an additional embodiment, the at least one groove comprises one groove, and the at least one conductor wire comprises six wires. In yet an additional embodiment, the at least one groove comprises six grooves, and the at least one conductor wire comprises six wires.

In at least one embodiment of a device of the present disclosure, the at least one groove does not completely encapsulate the at least one conductor wire when the at least one conductor wire is positioned therein. In an additional embodiment, the at least one conductor wire substantially or completely spans a length of the elongated body. In another embodiment, a proximal end of the elongated body is configured to effectively couple to a coupler unit. In yet another embodiment, the coupler unit is selected from the group consisting of a current source and a data acquisition and processing system.

In at least one embodiment of a device of the present disclosure, the device further comprises at least one sensor positioned along the elongated body, the at least one sensor coupled to the at least one wire when the at least one wire is positioned within the at least one elongated groove. In another embodiment, the at least one sensor is selected from the group consisting of an excitation electrode, a detection electrode, a pressure sensor, a thermistor, a pH sensor, and a terminal electrode connector array. In yet another embodiment, the at least one groove comprises six grooves, the at least one conductor wire comprises six wires, and the at least one sensor comprises five or six sensors.

In at least one embodiment of a device of the present disclosure, the device further comprises a sheath positioned around at least a portion of the elongated body. In an additional embodiment, the elongated body comprises a non-conductive material, and the at least one conductor wire comprises a conductive material. In yet an additional embodiment, the elongated body and the at least one conductor wire each comprises a conductive material. In another embodiment, the conductive material is selected from the group consisting of stainless steel, a nickel titanium alloy (such as Nitinol), copper, a nickel alloy (such as Monel), and a combination thereof. In yet another embodiment, the elongated body has one or more non-conductive coatings positioned around the elongated body to insulate the elongated body from the at least one conductor wire. In an additional embodiment, the at least one conductor wire has one or more non-conductive coatings positioned around the at least one conductor wire.

In at least one embodiment of a device of the present disclosure, the at least one groove is defined horizontally or helically around the elongated body. In another embodiment, the device further comprises a coupler unit coupled to a proximal end of the elongated body. In yet another embodiment, a signal can be carried along the at least one conductor wire to and/or from the coupler unit and the at least one sensor.

In at least one embodiment of a device of the present disclosure, the elongated body having the at least one groove defined therein is sufficiently rigid so to be safely inserted into a patient. In an additional embodiment, the device has a flexural rigidity of no less than 80% of a flexural rigidity of a second elongated body without at least one groove defined therein, wherein the elongated body and the second elongated body comprise the same material and have the same outer dimensions. In yet an additional embodiment, the at least one groove comprises one groove, and the flexural rigidity of the device is no less than approximately 16% of the flexural rigidity of the second elongated body. In another embodiment, the at least one groove comprises six grooves, and the flexural rigidity of the device is no less than approximately 20% of the flexural rigidity of the second elongated body.

In at least one embodiment of a device of the present disclosure, the device has a flexural rigidity of no less than 80% of a flexural rigidity of a second elongated body without at least one groove defined therein, wherein the elongated body and the second elongated body comprise the same material. In another embodiment, the at least one groove comprises one groove, the elongated body has an outer diameter of approximately 0.013", the second body has an outer diameter of approximately 0.0134", and the flexural rigidity of the device is no less than approximately 96% of the flexural rigidity of the second elongated body. In yet another embodiment, the at least one groove comprises six grooves, the elongated body has an outer diameter of approximately 0.013", the second body has an outer diameter of approximately 0.0134", and the flexural rigidity of the device is no less than approximately 92% of the flexural rigidity of the second elongated body.

In at least one embodiment of a device of the present disclosure, the at least one groove has a pitch between approximately 0.030" and approximately 1.50". In an additional embodiment, the at least one groove has a pitch selected from the group consisting of approximately 0.040" and approximately 0.120". In yet an additional embodiment, the device further comprises a coating positioned along the elongated body where the at least one wire is positioned within the at least one groove. In another embodiment, the device further comprises a bonding agent positioned along the elongated body where the at least one wire is positioned within the at least one groove.

In at least one embodiment of a device of the present disclosure, the device further comprises the at least one conductor wire positioned within the at least one groove, and at least one sensor positioned along the elongated body, the at least one sensor coupled to the at least one wire. In another embodiment, the at least one conductor wire comprises four conductor wires, the at least one sensor comprises four sensors, and the four conductor wires are separately coupled to the four sensors. In yet another embodiment, the four sensors comprise two outer excitation electrodes and two inner detection electrodes, wherein the excitation electrodes are operable to generate an electric field within a luminal organ that can be detected by the detection electrodes.

In at least one embodiment of a device of the present disclosure, the at least one groove comprises six grooves, the at least one conductor wire comprises six conductor wires, and the at least one sensor comprises four or five sensors. In another embodiment, the at least one conductor wire comprises six conductor wires, the at least one sensor comprises four sensors and one thermistor, and four of the six conductor wires are separately coupled to the four sensors, and the other two of the six conductor wires are coupled to the thermistor. In yet another embodiment, the at least one conductor wire comprises six conductor wires, the at least one sensor comprises four sensors or six sensors, and the six conductor wires are either separately coupled to the six sensors, or four of the conductor wires are coupled to four sensors and the other two conductor wires are coupled to the fifth sensor. In an additional embodiment, the six sensors comprise two outer excitation electrodes, two inner detection electrodes, and two thermistor wire ends, wherein the excitation electrodes are operable to generate an electric field within a luminal organ that can be detected by the detection electrodes, and wherein the thermistor wire ends are operable to detect a temperature of a fluid within the luminal organ.

In at least one embodiment of a device of the present disclosure, the elongated body defines a compliant portion positioned distal to an impedance portion, the impedance portion comprising one or more impedance electrodes and the compliant portion being relatively more flexible than a portion of the elongated body having the at least one groove defined therein. In another embodiment, the compliant portion is configured to assist a user with the delivery, positioning, and/or anchoring of the device within a luminal organ. In yet another embodiment, the device further comprises an atraumatic tip present at a distal end of the compliant portion, the atraumatic tip configured to avoid and/or limit the risk of puncture of a luminal organ by the device. In an additional embodiment, the elongated body further defines a connection portion at or near a proximal end of the device, the connection portion configured so that the at least one conductor wire may be electrically coupled to a coupler unit. In yet an additional embodiment, the connection portion comprises at least one connector, the at least one connector coupled to the at least one conductor wire. In another embodiment, the at least one conductor wire comprises six conductor wires, the at least one connector comprises six connectors, and the six conductor wires are separately coupled to the six connectors.

In at least one embodiment of a device of the present disclosure, the elongated body has a first portion having a first groove configuration and a second portion having second groove configuration, the first groove configuration and the second groove configuration each selected from the group consisting of a clockwise spiral configuration, a counter-clockwise spiral configuration, and a straight configuration. In another embodiment, the first groove configuration and the second groove configuration are configured to cancel negative effects of device whip and improve torque transfer. In yet another embodiment, the elongated body has a first portion having a first groove configuration, a second portion having second groove configuration, and a third portion having a third groove configuration, the first groove configuration, the second groove configuration, and the third groove configuration each selected from the group consisting of a clockwise spiral configuration, a counter-clockwise spiral configuration, and a straight configuration. In an additional embodiment, the at least one groove is also configured to receive a conductive polymer therein, the conductive polymer capable of transmitting a signal therethrough.

In at least one embodiment of a device of the present disclosure, the at least one groove comprises at least a first groove and a second groove, the first groove defined around the elongated body in a clockwise configuration, and the second groove defined around the elongated body in a counter-clockwise configuration. In an additional embodiment, the first groove and the second groove cancel negative effects of device whip and improve torque transfer. In yet an additional embodiment, the device further comprises the at least one conductor wire positioned within the first groove. In another embodiment, the device further comprises a coating positioned within the second groove. In yet another embodiment, the at least one conductor wire positioned within the first groove and the coating positioned within the second groove cancel negative effects of device whip and improve torque transfer.

In at least one embodiment of a device of the present disclosure, the elongated body has a first portion having a first groove configuration and a second portion having second groove configuration different from the first groove configuration. In another embodiment, the first portion and the second portion are in communication with one another at a coupler portion. In yet another embodiment, a circumferential notch is defined at the coupler portion. In an additional embodiment, the device further comprises a coupler positioned around the device at the circumferential notch, the coupler configured to hold the at least one conductor wire when positioned within the at least one groove.

In at least one embodiment of a device of the present disclosure, a distal end of the elongated body is tapered, and when at least one conductor wire is positioned within the at least one groove, a distal portion of the at least one conductor wire is released at or near the tapered distal end of the elongated body. In an additional embodiment, the device further comprises a flexible coating positioned around at least part of the elongated body, so that when the elongated body is curved or bent, the flexible coating remains sufficiently around at least part of the elongated body. In another embodiment, the one or more conductor wires form an assembly of wires whereby each of the one or more conductor wires are insulated from one another by way of a coating. In yet another embodiment, the device further comprises the assembly of wires positioned within the at least one groove.

In at least one embodiment of a device of the present disclosure, the elongated body comprises a nonconductive material comprising carbon fiber and a flexible polymer. In another embodiment, the device further comprises an elongated core material positioned within the elongated body. In yet another embodiment, the elongated core material is selected from the group consisting of stainless steel, copper and a nickel titanium alloy.

In at least one embodiment of a device of the present disclosure, the elongated body comprises a nonconductive material, and the at least one groove is defined therein by pushing or pulling the elongated body through a die having an outer portion and one or more die tabs, the one or more die tabs define the at least one groove. In an additional embodiment, the device further comprises an elongated core material positioned within the elongated body, the elongated core material selected from the group consisting of stainless steel, copper, and a nickel titanium alloy. In yet an additional embodiment, the at least one groove is defined therein in a spiral configuration by turning the die relative to the elongated body when the elongated body is pushed or pulled therethrough. In another embodiment, the at least one groove is defined therein in a spiral configuration by turning the elongated body relative to the die when the elongated body is pushed or pulled therethrough.

In at least one embodiment of a device of the present disclosure, the elongated body comprises a wavy configuration. In an additional embodiment, the coupler unit comprises a tiered receptacle configured to fit the proximal end of the elongated body, the tiered receptacle comprising an inner portion and an outer portion configured to receive the elongated body having a first outer diameter or a second different outer diameter. In another embodiment, a proximal end of the elongated body is configured to fit within an outer portion of an adapter, the adapter configured to fit within a coupler unit.

In at least one embodiment of a method to manufacture a device of the present disclosure, the method comprises the steps of positioning a plurality of conductor wires within an elongated shell, whereby the plurality of conductor wires are separate from one another, and filling the elongated shell with a first material, wherein when the first material is cured and/or cooled, the first material and the plurality of conductor wires form an elongated device. In another embodiment, the first material comprises a nonconductive material comprising carbon fiber and a flexible polymer. In yet another embodiment, the method further comprises the step of positioning a core metallic body within the elongated shell at or near a relative center of the elongated shell prior to filling the elongated shell with the first material.

In at least one embodiment of an impedance substrate of the present disclosure, the impedance substrate comprises a flexible material substrate having an impedance portion with at least one impedance electrode and at least one first conductor wire positioned thereon and/or therein, the at least one first conductor wire operatively connected to the impedance portion and terminating at or near a proximal end of the impedance substrate, the impedance substrate configured to fit around at least part of an elongated body sized and shaped to fit within a mammalian body lumen. In another embodiment, the impedance substrate further comprises a temperature portion and at least one second conductor wire positioned thereon and/or therein, the at least one second conductor wire operatively connected to the temperature portion and terminating at or near a proximal end of the impedance substrate. In yet another embodiment, when the impedance substrate is wrapped around a portion of the elongated body having at least one first elongated body conductor wire positioned thereon and/or therein, and wherein when the at least one first elongated body conductor wire contacts the at least one first conductor wire, a signal may be transmitted from the impedance portion, through the at least one first conductor wire, and through the at least one first elongated body conductor wire. In an additional embodiment, when the impedance substrate is wrapped around a portion of the elongated body having at least one first elongated body conductor wire and at least one second elongated body conductor wire positioned thereon and/or therein, and wherein when the at least one first elongated body conductor wire contacts the at least one first conductor wire and the at least one second elongated body conductor wire contacts the at least one second conductor wire, a first signal may be transmitted from the impedance portion, through the at least one first conductor wire, and through the at least one first elongated body conductor wire, and a second signal may be transmitted from the temperature portion, through the at least one second conductor wire, and through the at least one second elongated body conductor wire.

In at least one embodiment of an impedance substrate of the present disclosure, the flexible material substrate is relatively thicker at the temperature portion than at the impedance portion. In an additional embodiment, when the impedance substrate is wrapped around a portion of the elongated body having a tapered portion, and wherein the temperature portion of the impedance substrate is positioned at the tapered portion of the elongated body, the impedance substrate maintains a consistent outer dimension. In yet an additional embodiment, the flexible material substrate is configured so that it can be wound around at least part of the elongated body.

In at least one embodiment of an connector substrate of the present disclosure, the connector substrate comprises a flexible material substrate having a connection portion with at least one connector and at least one first conductor wire positioned thereon and/or therein, the at least one first conductor wire operatively connected to the connection portion and terminating at or near a distal end of the connector substrate, the connector substrate configured to fit around at least part of an elongated body sized and shaped to fit within a mammalian body lumen. In another embodiment, when the connector substrate is wrapped around a portion of the elongated body having at least one first elongated body conductor wire positioned thereon and/or therein, and when the at least one first elongated body conductor wire contacts the at least one first conductor wire, a signal may be transmitted through the at least one first elongated body conductor wire, through the at least one first conductor wire, and to the connection portion.

In at least one embodiment of a device of the present disclosure, the device comprises an elongated body having at least one elongated body conductor wire positioned thereon and/or therein, an impedance substrate of the present disclosure positioned around at least part of the elongated body at a first end, and a connector substrate of the present disclosure positioned around at least part of the elongated body at a second end, wherein a signal may be transmitted from the impedance substrate, through the at least one elongated body conductor wire, to the connector substrate. In another embodiment, the impedance substrate and/or the connector substrate are coupled to the elongated body using an adhesive. In yet another embodiment, the impedance substrate and/or the connector substrate are shrink-wrapped or heat-shrinked around the elongated body.

In at least one embodiment of a device of the present disclosure, the device comprises an elongated body with at least one groove defined therein, the at least one groove configured to receive a conductive polymer therein, the conductive polymer capable of transmitting a signal therethrough.

In at least one embodiment of a device of the present disclosure, the device comprises an elongated body with a plurality of conductor wires embedded therein, each of the plurality of conductor wires separated from one another by at least part of the elongated body, whereby the plurality of conductor wires are positioned around a perimeter of the elongated body. In another embodiment, each of the plurality of conductor wires are surrounded by a coating. In yet another embodiment, the core body comprises a conductive material, and wherein the coating comprises a non-conductive material. In an additional embodiment, the plurality of conductor wires comprises six conductor wires.

In at least one embodiment of a device of the present disclosure, the plurality of conductive wires are not exposed along a surface of the elongated body. In an additional embodiment, the plurality of conductive wires are nominally exposed along a surface of the elongated body. In yet an additional embodiment, approximately 10% or less of a circumference of the plurality of conductor wires are exposed along a surface of the elongated body.

In at least one embodiment of an elongated wrap of the present disclosure, the elongated wrap comprises a flexible wrap body having a plurality of conductor wires or traces positioned thereon and/or therein around a relative perimeter of the flexible wrap body, the flexible wrap body configured to fit around at least part of an elongated body sized and shaped to fit within a mammalian body lumen. In an additional embodiment, the flexible wrap body is capable of adhering to the elongated body using an adhesive. In yet an additional embodiment, the flexible wrap body is capable of adhering to the elongated body by way of heat-shrinking or shrink-wrapping. In another embodiment, the flexible wrap body is sized and shaped to fit around an elongated body having a diameter of approximately 0.0131". In another embodiment, the flexible wrap body comprises a polyimide.

In at least one embodiment of an elongated wrap of the present disclosure, the plurality of conductor wires are within an assembly of conductor wires. In another embodiment, the plurality of conductor wires or traces are positioned along the flexible wrap body in a configuration selected from the group of a straight configuration and a helical configuration. In yet another embodiment, the elongated wrap further comprises at least one portion selected from the group consisting of an impedance portion, a temperature portion, and connection portion. In an additional embodiment, the plurality of conductor wires or traces comprises thirty-six total conductor wires or traces.

In at least one embodiment of an elongated wrap of the present disclosure, the plurality of conductor wires have a cross-section selected from the group consisting of round, square, and rectangular. In an additional embodiment, the plurality of conductor wires or traces are separated by one or more shrink zones configured to shrink around an elongated body.

In at least one embodiment of an elongated wrap of the present disclosure, the elongated wrap comprises a flexible wrap body having a plurality of wide conductors embedded therein or positioned thereon and/or therein around a relative perimeter of the flexible wrap body, the flexible wrap body configured to fit around at least part of an elongated body sized and shaped to fit within a mammalian body lumen. In another embodiment, the plurality of conductor wires or traces are separated by one or more shrink zones configured to shrink around an elongated body. In yet another embodiment, the plurality of wide conductors have a cross-section selected from the group consisting of a rectangular cross-section or a quasi-rectangular cross-section. In an additional embodiment, the elongated wrap further comprises at least one portion selected from the group consisting of an impedance portion, a temperature portion, and connection portion.

In at least one embodiment of a device of the present disclosure, the elongated body comprises inherent properties of flexural rigidity, pushability, and torque transfer, wherein said properties are sufficient to permit a user to advance, retract, and steer the elongated body as desired within a patient's luminal organ.

In at least one embodiment of a system of the present disclosure, the system comprises an exemplary device of the present disclosure and a coupler unit, wherein a proximal end of the exemplary device is configured to effectively couple to the coupler unit.

In at least one embodiment of a method of manufacturing a device of the present disclosure, the method comprises the steps of introducing at least one groove into an elongated body of a device, and positioning at least one conductor wire within at least part of the at least one groove. In another embodiment, the method further comprises the step of applying a coating of non-conductive material to at least part of the elongated body. In yet another embodiment, the method further comprises the step of applying an adhesive agent to the at least one groove and/or the at least one conductor wire. In an additional embodiment, the method further comprises the step of applying a coating to the at least one conductor wire within the at least one groove.

In at least one embodiment of a method of manufacturing a device of the present disclosure, the method further comprises the step of applying one or more electrodes and/or one or more thermistor electrodes to the device. In an additional embodiment, the method further comprises the step of connecting the one or more electrodes and/or the one or more thermistor wire ends to one or more connectors by way of the at least one conductive wire. In yet an additional embodiment, the at least one conductor wire comprises at least four conductor wires.

In at least one embodiment of a method of using a device of the present disclosure, the method comprises the steps of inserting an exemplary device of the present disclosure into a luminal organ of a patient, and advancing the exemplary device to a desired location within the patient. In another embodiment, the method further comprises the step of activating the exemplary device by applying a current therethrough. In yet another embodiment, the method further comprises the step of injecting a fluid into the luminal organ so that the fluid passes one or more electrodes of the exemplary device to facilitate one or more impedance readings. In an additional embodiment, the one or more impedance readings include those useful to ultimately determine one or more of a fractional flow reserve, a coronary flow reserve, a cross-sectional area, and a temperature reading.

In at least one embodiment of a method of using a device of the present disclosure, a disease or a disorder of the patient may be diagnosed in connection with one or more determinations. In another embodiment, the method further comprises the step of withdrawing the exemplary device from the patient.

In at least one embodiment of a device of the present disclosure, the device comprises an elongated core body having a length, a perimeter, and a cross-sectional configuration, a plurality of conductive elements positioned around the perimeter of the core body and extending a majority of the length of the core body, the plurality of conductive elements surrounded by a first substantially or completely non-conductive coating, wherein the device, having the first (or at least one) substantially or completely non-conductive coating, has an overall round cross-section and an overall diameter between approximately 0.013" and approximately 0.050". In another embodiment, the elongated core body has a plurality of grooves defined therein, each of the plurality of grooves configured to receive at least one of the plurality of conductive elements therein. In yet another embodiment, the plurality of conductive elements comprises a plurality of conductive wires. In an additional embodiment, the elongated core body has a plurality of grooves defined therein, each of the plurality of grooves configured to receive at least one of the plurality of conductive wires therein. In yet an additional embodiment, each of the plurality of conductive wires is surrounded by the first substantially or completely non-conductive coating.

In at least one embodiment of a device of the present disclosure, the device is further surrounded by a second substantially or completely non-conductive coating, the second substantially or completely non-conductive coating defining the overall round cross-section. In an additional embodiment, the elongated core body is at least partially surrounded by the first substantially or completely non-conductive coating, and wherein the plurality of conductive wires are not individually coated prior to placement within the plurality of grooves In yet an additional embodiment, the device is further surrounded by a second substantially or completely non-conductive coating, the second substantially or completely non-conductive coating defining the overall round cross-section.

In at least one embodiment of a device of the present disclosure, the cross-sectional configuration comprises a round cross-sectional configuration. In another embodiment, the cross-sectional configuration comprises a hexagonal cross-sectional configuration defining six planar sides. In yet another embodiment, the hexagonal cross-sectional configuration further defines one or more reduced corners. In an additional embodiment, the elongated core body is at least partially surrounded by the first substantially or completely non-conductive coating, and wherein the plurality of conductive elements are positioned on the first substantially or completely non-conductive coating.

In at least one embodiment of a device of the present disclosure, the plurality of conductive elements comprise a plurality of conductor wires having a rectangular cross-section. In an additional embodiment, the plurality of conductive elements are positioned on the first substantially or completely non-conductive coating using an adhesive. In yet an additional embodiment, the device is further surrounded by a second substantially or completely non-conductive coating, the second substantially or completely non-conductive coating defining the overall round cross-section.

In at least one embodiment of a device of the present disclosure, the device is further surrounded by a second substantially or completely non-conductive coating. In another embodiment, the device is further surrounded by a third substantially or completely non-conductive coating, the third substantially or completely non-conductive coating defining the overall round cross-section. In yet another embodiment, each of the plurality of conductive elements is surrounded by the first substantially or completely non-conductive coating. In an additional embodiment, the device is further surrounded by a second substantially or completely non-conductive coating, so that the second substantially or completely non-conductive coating surrounds at least part of the plurality of conductive elements surrounded by the first substantially or completely non-conductive coating. In an additional embodiment, the device is further surrounded by a third substantially or completely non-conductive coating, the third substantially or completely non-conductive coating defining the overall round cross-section.

In at least one embodiment of a device of the present disclosure, the elongated core body is at least partially surrounded by the first substantially or completely non-conductive coating, and wherein the plurality of conductive elements are positioned on the first substantially or completely non-conductive coating. In an additional embodiment, the plurality of conductive elements are selected from the group consisting of a plurality of conductive wires and a plurality of conductive traces. In yet an additional embodiment, the plurality of conductive elements comprises a plurality of conductive traces produced by initially placing one or more conductive traces upon the elongated core body at least partially surrounded by the first substantially or completely non-conductive coating and removing portions of the one or more conductive traces to result in the plurality of conductive traces. In another embodiment, the plurality of conductive elements comprises a plurality of conductive traces produced by initially coating the elongated core body with a single conductive trace and removing portions of the single conductive trace to result in the plurality of conductive traces. In yet another embodiment, the plurality of conductive traces each have a gap defined therebetween. In an additional embodiment, the device is further surrounded by a second substantially or completely non-conductive coating, the second substantially or completely non-conductive coating defining the overall round cross-section.

In at least one embodiment of a device of the present disclosure, the plurality of conductive elements comprise a plurality of conductive traces. In another embodiment, the plurality of conductive traces are produced by initially placing one or more conductive traces upon the elongated core body at least partially surrounded by the first substantially or completely non-conductive coating and removing portions of the one or more conductive traces to result in the plurality of conductive traces. In an additional embodiment, the plurality of conductive traces each have a gap defined therebetween. In yet an additional embodiment, the device is further surrounded by a second substantially or completely non-conductive coating, the second substantially or completely non-conductive coating defining the overall round cross-section.

In at least one embodiment of a device of the present disclosure, the elongated core body comprises stainless steel, and wherein the plurality of conductive elements comprise a material selected from the group consisting of gold and copper. In an additional embodiment, the device further comprises a detector coupled to the device at or near a distal end of the device, the detector configured to obtain conductance data when the device is operated in a fluid environment. In yet an additional embodiment, the detector is coupled to one or more of the plurality of conductive elements, so that a signal may be transmitted along the one or more of the plurality of conductive elements to and/or from the detector. In another embodiment, the detector comprises two detection electrodes positioned in between two excitation electrodes, wherein the excitation electrodes are operable to generate an electric field within a luminal organ that can be detected by the detection electrodes to obtain conductance data indicative of the luminal organ. In yet another embodiment, the device further comprises two thermistor wire ends operable to detect a temperature of a fluid within the luminal organ.

In at least one embodiment of a device of the present disclosure, the detector comprises part of an impedance substrate positioned upon the device. In an additional embodiment, the device further comprises a connection portion coupled to the device at or near a proximal end of the device, the connection portion configured to transmit conductance data from the plurality of conductive elements through the connection portion to a coupler unit. In an additional embodiment, the connection portion comprises part of a connector substrate positioned upon the device.

In at least one embodiment of a device of the present disclosure, the device comprises an elongated core body having a length, a perimeter, and a cross-sectional configuration selected from the group consisting of a round configuration and a hexagonal configuration, a plurality of conductive elements positioned around the perimeter of the core body and extending a majority of the length of the core body, the plurality of conductive elements surrounded by a first substantially or completely non-conductive coating, and a detector coupled to the device at or near a distal end of the device and operably connected to one or more of the plurality of conductive elements, the detector configured to obtain conductance data when the device is operated in a fluid environment and to transmit the conductance data along one or more of the plurality of conductive elements, wherein the device, having the first (or at least one) substantially or completely non-conductive coating, has an overall round cross-section and an overall diameter between approximately 0.013" and approximately 0.050". In another embodiment, the detector comprises two detection electrodes positioned in between two excitation electrodes, wherein the excitation electrodes are operable to generate an electric field within a luminal organ that can be detected by the detection electrodes to obtain conductance data indicative of the luminal organ. In yet another embodiment, the device further comprises two thermistor wire ends operable to detect a temperature of a fluid within the luminal organ. In an additional embodiment, the detector comprises part of an impedance substrate positioned upon the device. In yet an additional embodiment, the plurality of conductive elements are selected from the group consisting of a plurality of conductive wires and a plurality of conductive traces.

In at least one embodiment of a device of the present disclosure, the device further comprises a connection portion coupled to the device at or near a proximal end of the device, the connection portion configured to transmit conductance data from the plurality of conductive elements through the connection portion to a coupler unit.

In at least one embodiment of a method of preparing a device of the present disclosure, the method comprises the steps of positioning a plurality of conductive elements upon an elongated conductive core to form a partial device, and applying an outer substantially or completely non-conductive coating to the partial device so that the device, having the outer substantially or completely non-conductive coating applied thereon, has an overall round cross-section and an overall diameter between approximately 0.013" and approximately 0.050". In an additional embodiment, the positioning step is performed by positioning the plurality of conductive elements upon the elongated conductive core that is surrounded by an inner substantially or completely non-conductive coating. In an additional embodiment, the method further comprises the step of connecting a detector to the device at or near a distal end of the device, the detector configured to obtain conductance data when the device is operated in a fluid environment. In another embodiment, the connecting step is performed by connecting the detector to one or more of the plurality of conductive elements so that a signal may be transmitted along the one or more of the plurality of conductive elements to and/or from the detector. In yet another embodiment, the connecting step is performed by connecting the detector comprising two inner detection electrodes and two outer excitation electrodes to two or more of the plurality of conductive elements so that a signal may be transmitted along the two or more of the plurality of conductive elements to and/or from the detector.

In at least one embodiment of a method of preparing a device of the present disclosure, the connecting step is further performed by connecting two thermistor wire ends to two or more of the plurality of conductive elements so that a signal may be transmitted from the two thermistor wire ends along the two or more of the plurality of conductive elements. In another embodiment, the positioning step is performed by positioning the plurality of conductive elements within a plurality of grooves defined within the elongated conductive core. In yet another embodiment, the positioning step is performed by positioning the plurality of conductive elements upon the elongated conductive core having a hexagonal cross-section so that each conductive element of the plurality of conductive elements is positioned on a separate side of the elongated conductive core. In an additional embodiment, the positioning step is performed by positioning the plurality of conductive elements upon the elongated conductive core that is surrounded by an inner substantially or completely non-conductive coating. In yet an additional embodiment, the positioning step further comprises applying a middle substantially or completely non-conductive coating to the partial device.

In at least one embodiment of a method of preparing a device of the present disclosure, the positioning step is performed by positioning the plurality of conductive elements comprising a plurality of conductive traces upon the elongated conductive core that is surrounded by an inner substantially or completely non-conductive coating. In an additional embodiment, the method further comprises the step of etching at least one of the plurality of conductive elements to increase an overall number of conductive elements. In yet an additional embodiment, the positioning step is performed by positioning the plurality of conductive traces upon the elongated conductive core having a cross-section selected from the group consisting of a round cross-section and a hexagonal cross-section. In another embodiment, the step of connecting the detector to the device is performed by connecting the detector comprising part of an impedance substrate to the device.

In at least one embodiment of a method of preparing a device of the present disclosure, the method further comprises the step of connecting a connection portion to the device at or near a proximal end of the device, the connection portion configured to transmit conductance data from the plurality of conductive elements through the connection portion to a coupler unit. In another embodiment, the step of connecting the connection portion to the device is performed by connecting the connection portion comprising part of a connector substrate to the device.

BRIEF DESCRIPTION OF THE DRAWINGS

The disclosed embodiments and other features, advantages, and disclosures contained herein, and the matter of attaining them, will become apparent and the present disclosure will be better understood by reference to the following description of various exemplary embodiments of the present disclosure taken in conjunction with the accompanying drawings, wherein:

FIG. 3A shows a perspective view of a core wire prior to having any grooves defined therein, according to an exemplary embodiment of the present disclosure;

FIG. 3B shows a perspective view of a device body having a plurality of grooves defined therein and a plurality of wires positioned therein, according to an exemplary embodiment of the present disclosure;

FIG. 3C shows a perspective view of a device body having a single groove defined therein and a plurality of wires positioned therein, according to an exemplary embodiment of the present disclosure;

FIG. 3D shows a schematic representative of flexural rigidity testing, according to an exemplary embodiment of the present disclosure;

FIGS. 6A and 6B show devices having a single groove and a plurality of grooves and a plurality of wires positioned therein and a coating positioned thereon, according to an exemplary embodiment of the present disclosure;

FIG. 8A shows a device having various components, electrodes, and connectors positioned thereon, according to an exemplary embodiment of the present disclosure;

FIG. 8B shows a distal portion of device having various electrodes positioned thereon, according to an exemplary embodiment of the present disclosure;

FIG. 9A shows a cut-away side view of a portion of a device with a groove defined therein, according to an exemplary embodiment of the present disclosure;

FIG. 9B shows a proximal portion of device having various connectors positioned thereon, according to an exemplary embodiment of the present disclosure;

FIGS. 12A-12D show side views of devices with two groove configurations, according to exemplary embodiments of the present disclosure;

FIGS. 13A-13D show side views of devices with two groove configurations, according to exemplary embodiments of the present disclosure;

FIG. 16A shows an impedance substrate with an impedance portion and a temperature portion, according to an exemplary embodiment of the present disclosure;

FIG. 16B shows the impedance substrate of FIG. 16A positioned next to an elongated body, according to an exemplary embodiment of the present disclosure;

FIG. 16C shows the impedance substrate of FIG. 16A positioned upon part of an elongated body, according to an exemplary embodiment of the present disclosure;

FIG. 16D shows the impedance substrate of FIG. 16A wrapped around part of an elongated body, according to an exemplary embodiment of the present disclosure;

FIG. 16E shows a connector substrate with an impedance portion and a temperature portion, according to an exemplary embodiment of the present disclosure;

FIG. 16F shows the connector substrate of FIG. 16E positioned next to an elongated body, according to an exemplary embodiment of the present disclosure;

FIG. 16G shows the connector substrate of FIG. 16E positioned upon part of an elongated body, according to an exemplary embodiment of the present disclosure;

FIG. 16H shows the connector substrate of FIG. 16E wrapped around part of an elongated body, according to an exemplary embodiment of the present disclosure;

FIG. 16I shows an impedance substrate and a connector substrate wrapped around part of an elongated body, according to an exemplary embodiment of the present disclosure;

FIG. 18A shows a cross-sectional view of a conductor wire assembly, according to an exemplary embodiment of the present disclosure;

FIG. 18B shows a portion of a conductor wire assembly placed within a groove of a core body, according to an exemplary embodiment of the present disclosure;

FIG. 23 shows a side view of a device having a wavy configuration, according to an exemplary embodiment of the present disclosure;

FIGS. 26A-28A show cross-sectional configurations of various devices having conductive elements therein, according to exemplary embodiments of the present disclosure;

FIG. 28B shows exemplary profiles of device distal ends, according to exemplary embodiments of the present disclosure;

FIG. 29A shows a distal portion of a device, according to an exemplary embodiment of the present disclosure;

FIG. 29B shows an impedance substrate, according to an exemplary embodiment of the present disclosure; and FIG. 29C shows a distal portion of a device with an impedance substrate positioned thereon, according to an exemplary embodiment of the present disclosure.

Figure 1A:
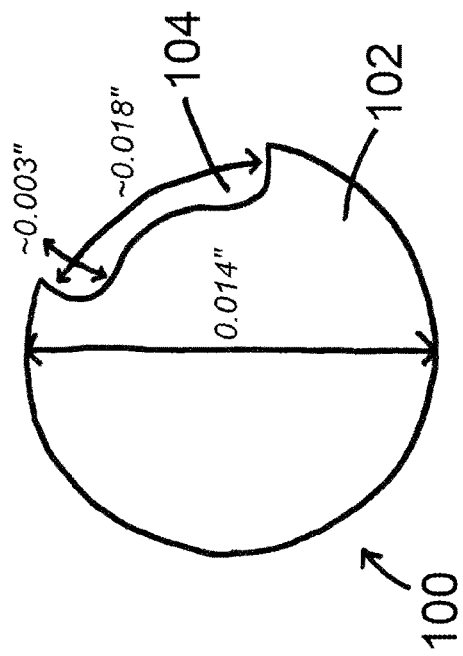
FIG. 1A shows a perspective view of a device according to an exemplary embodiment of the present disclosure.

An overview of the features, functions and/or configurations of the components depicted in the various figures will now be presented. It should be appreciated that not all of the features of the components of the figures are necessarily described. Some of these non-discussed features, such as various couplers, etc., as well as discussed features are inherent from the figures themselves. Other non-discussed features may be inherent in component geometry and/or configuration.

DETAILED DESCRIPTION

For the purposes of promoting an understanding of the principles of the present disclosure, reference will now be made to the embodiments illustrated in the drawings, and specific language will be used to describe the same. It will nevertheless be understood that no limitation of the scope of this disclosure is thereby intended.

In at least one embodiment of a device 100 of the present application, device 100 comprises an elongated body 102 having at least one groove 104 defined therein. Groove 104, in various embodiments, is configured to receive one or more conductor wires 110 therein.

Figure 1B:
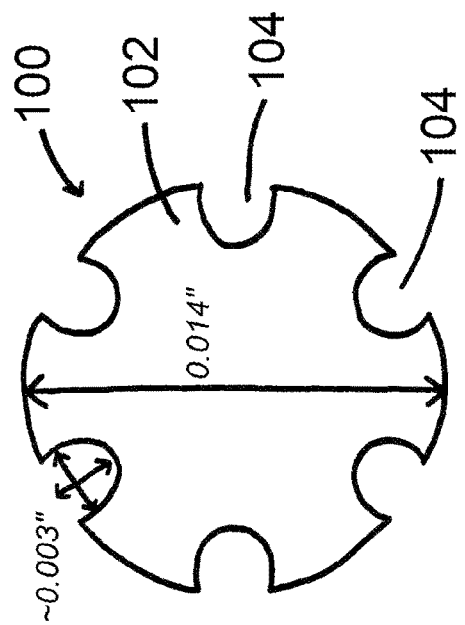
FIG. 1B shows a cross-sectional view of the device of FIG. 1A, according to an exemplary embodiment of the present disclosure.

FIGS. 1A and 1B show perspective and cross-sectional views, respectively, of an exemplary device 100 of the present disclosure, whereby body 102 is a solid body having a single groove 104 defined therein. As shown in FIG. 1B, an exemplary body 102 has an outer diameter of 0.014", a groove 104 depth of approximately 0.003", and a relative groove width of approximately 0.018". In other embodiments, different sizes/measurements may be used, such as a 0.035" outer diameter body 102, smaller or larger outer diameter bodies 102, and/or smaller or larger groove 104 depths and relative widths. In various embodiments, body 102 has an outer diameter between approximately 0.010" and approximately 0.050."

Figure 1C:
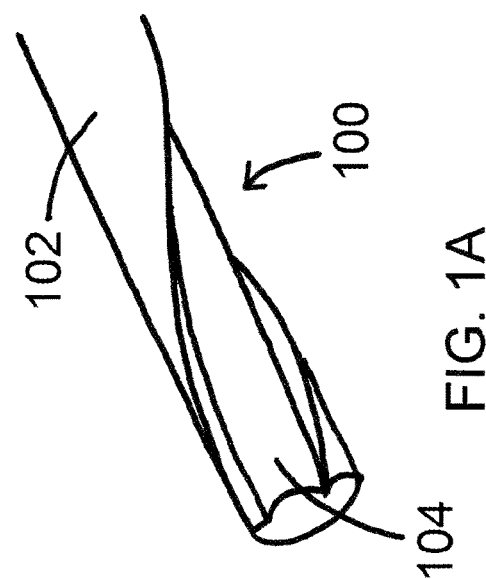
FIG. 1C shows a perspective view of a device according to another exemplary embodiment of the present disclosure.
Figure 1D:
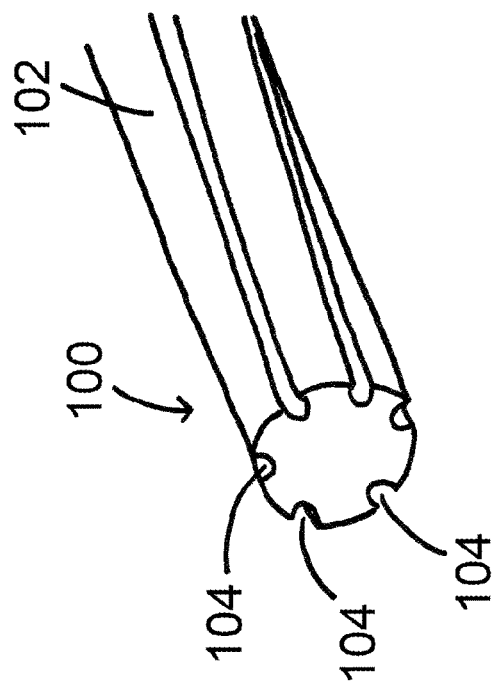
FIG. 1D shows a cross-sectional view of the device of FIG. 1C, according to an exemplary embodiment of the present disclosure.

FIGS. 1C and 1D show perspective and cross-sectional views, respectively, of an exemplary device 100 of the present disclosure, whereby body 102 is a solid body having a plurality of grooves 104 defined therein. As shown in FIG. 1D, six grooves 104 are defined therein, and in other embodiments, more or fewer grooves 104 may be defined therein. In at least one embodiment, and as shown in FIG.

1D, an exemplary body 102 has an outer diameter of 0.014", and a groove 104 depth and relative width of approximately 0.003" each.

Figure 2A:
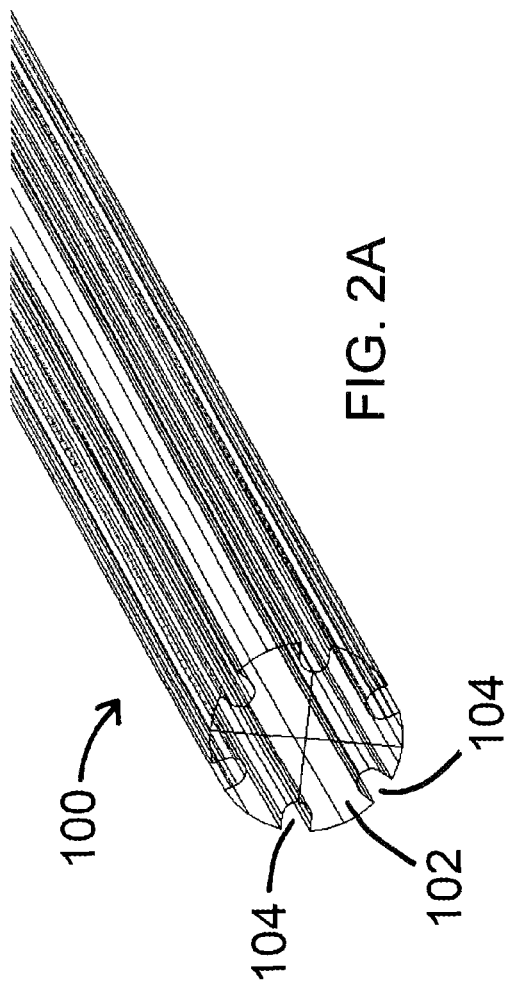
FIG. 2A shows a line drawing perspective view of a device according to an exemplary embodiment of the present disclosure.

A line-drawing perspective view of an exemplary device 100 embodiment is shown in FIG. 2A. As shown in FIG. 2A, device 100 comprises a body 102 having a plurality of grooves 104 defined therein, whereby a groove 104 does not completely encapsulate a conductor wire 110 when conductor wire 110 is positioned therein.

Figure 2B:
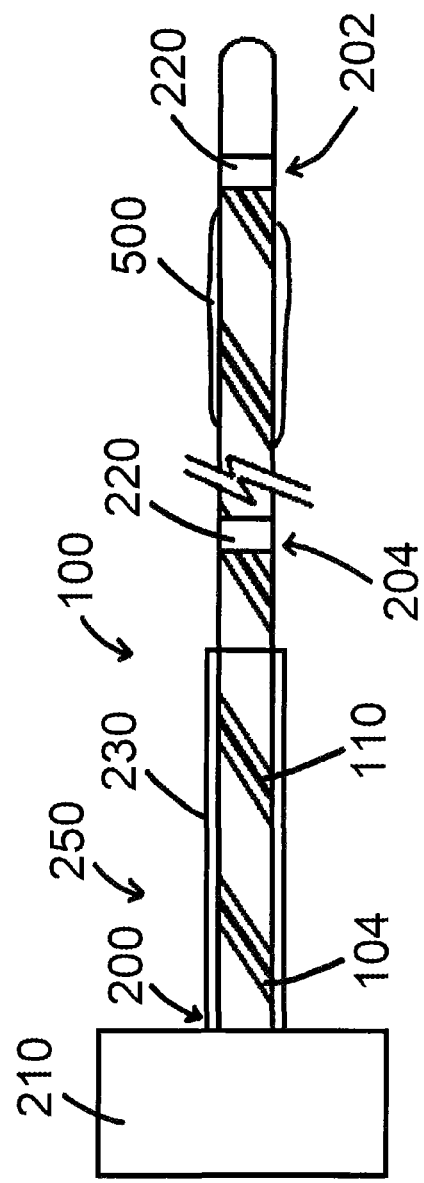
FIG. 2B shows a side view of a device coupled to a coupler unit, according to an exemplary embodiment of the present disclosure.

As shown in FIG. 2B, grooves 104 of device 100 are configured so that conductor wires 110 present therein can substantially or completely span the length of device 100. In such an embodiment, a proximal end 200 of conductor wire 110 can effectively connect to a coupler unit 210 such as, for example, a console, a current source, a data acquisition and processing system, and/or the like, and so that another portion of conductor wire 110, such as a distal end 202 and/or an internal portion 204 of conductor wire 110, can couple to and/or form a sensor 220, such as an excitation electrode, a detection electrode, a pressure sensor, a thermistor, a pH sensor, a terminal electrode connector array and/or the like. An exemplary sensor 220 of the present disclosure may be one or more of an electrode 802, 804, 806, 808 and/or a thermistor (temperature portion 810, having thermistor wire ends 812, 814, as referenced in further detail herein). In addition, and in at least one embodiment, a sheath 230 may be positioned around at least a portion of body 102, as shown in FIG. 2B, to cover at least part of device 100. As referenced herein, and as shown in FIG. 2B, an exemplary system 250 of the present disclosure comprises an exemplary device 100 of the present disclosure and at least one other component, such as, for example, a coupler unit 210.

In various embodiments, body 102 comprises a non-conductive material, and conductor wires 110 comprise a conductive material. In other embodiments, and as described in further detail herein, body 102 and conductor wires 110 are each conductive, and a non-conductive material, such as one or more non-conductive coatings 500 positioned around body 102 and/or one or more conductor wires 110, may be used to effectively insulate body 102 from conductor wires 110.

In various embodiments, grooves 104 can be defined in various configurations along body 102, such a horizontally (or substantially horizontally) as shown in FIG. 2A, helically (or substantially helically) as shown in FIGS. 1A-1D, and/or another configuration whereby a conductor wire 110 present therein is capable of carrying a signal (data, electrical, and/or otherwise) along conductor wire 110, to and/or from a coupler unit 210 and/or a sensor 220, for example.

FIG. 3A shows an exemplary core wire used as a body 102 of the present application prior to having any grooves therein. As shown in FIG. 3A, body 102 is an elongated core wire which may be comprised of stainless steel, a nickel titanium alloy (such as Nitinol), copper, a nickel alloy (such as Monel), a combination of the foregoing, and/or another material suitable as a conductor wire 110 that is sufficiently rigid, when one or more grooves 104 are present therein, to be safely inserted into a patient. FIG. 3B shows an exemplary device 100 of the present disclosure having six grooves 104 defined within body 102 and showing six separate conductor wires 110, wherein one conductor wire 110 positioned within each groove 104. FIG. 3C shows another exemplary device 100 of the present disclosure, whereby a single helical groove 104 is defined within body 102, whereby the single helical groove 104 is sized and shaped to receive all six conductor wires 110 therein. In various other embodiments of devices 100 of the present disclosure, devices 100 may have a single groove 104 or two or more grooves 104, and said grooves 104 may be horizontal along a horizontal axis of body 102, helically around body 102, or in some other configuration around body 102.

The exemplary device 100 embodiments shown in FIGS. 3B and 3C were tested, in various experiments, to determine the flexural rigidities relative to each other and relative to the core, ungrooved body shown in FIG. 3A. In each experiment, a body 102 having an outer diameter of 0.013" was tested, and conductor wires 110 of 0.002" in diameter were used. A calculated flexural rigidity ($EI=FL^3/(3\delta)$, wherein EI is the flexural rigidity of dimension $N \cdot mm^2$ (a combination of E, which is the effective Young's Modulus of the composite material and I is the second moment of inertia), F is the downward pull force at the end of the exposed length of the body used in the test, L is the exposed length of the body used in the test, and $\delta$ is the spatial deflection at the free end due to the overall downward pull force. A flexural rigidity of 116.7 for the core body shown in FIG. 3A was obtained as compared to 98.95 (a 15.2% decrease) for the device 100 shown in FIG. 3B and as compared to 93.84 (a 19.6% decrease) for the device 100 shown in FIG. 3C. In various embodiments, flexural rigidity increased to 108.79 (a 3.79% decrease compared to the core shown in FIG. 3A) for a device 100 shown in FIG. 3B having an increased body 102 diameter of 0.0134", and a corresponding flexural rigidity of 107.85 (a 7.58% decrease compared to the core shown in FIG. 3A) for a device 100 shown in FIG. 3C having an increased body 102 diameter of 0.0134".

Figure 3E:
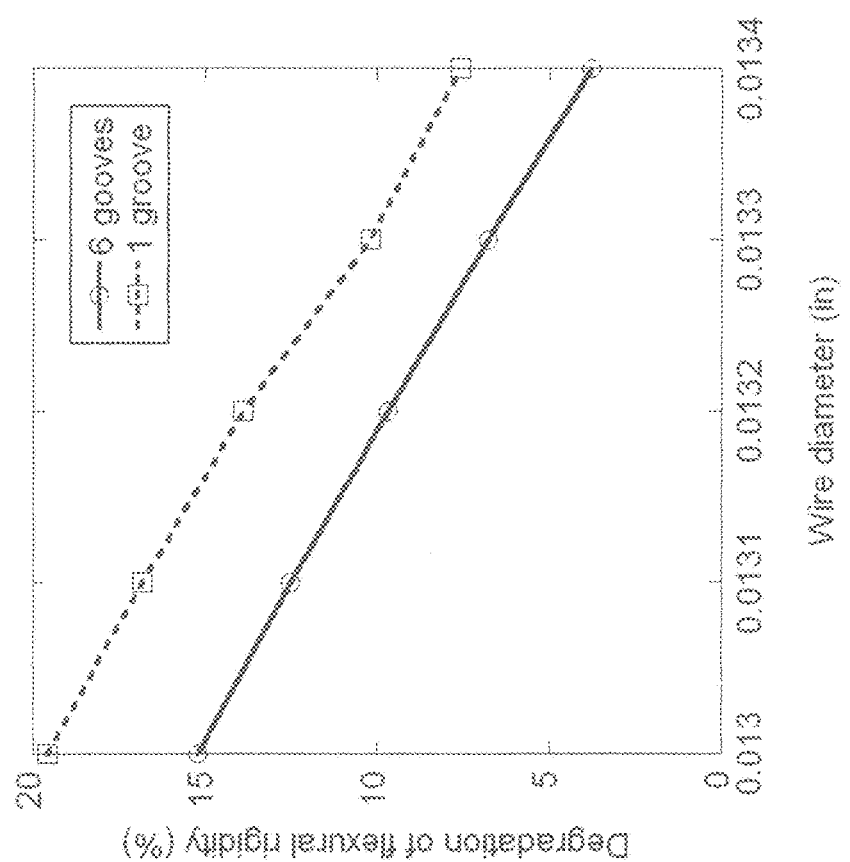
FIG. 3E shows a chart depicting the percentage degradation of flexural rigidity versus the outer diameter of a device, according to various exemplary device embodiments of the present disclosure.

The above-referenced data was obtained whereby the exposed length (L) of the body was 3.07 mm, as shown in FIG. 3D. FIG. 3E shows a graph of the data (percentage degradation of flexural rigidity versus the outer diameter of the wire), whereby the largest percentage degradation exists at the most narrow diameter wire embodiments. As shown therein, and consistent with the data above, an increase of 0.004" has a significant effect on flexural rigidity.

As the core body, comprising one or more materials described herein, has the highest flexural rigidity given that there are no grooves therein (so that a relative 100% of body mass is preserved), any grooves 104 cut or otherwise defined within body 102 would serve to decrease the overall flexural rigidity. At least one optimally designed device 100 of the present disclosure, depending on intended use, would have as high of a flexural rigidity as possible compared to a desired flexural rigidity of a core body (used as an interventional guidewire, for example) and be prepared at as low of a cost as possible. In view of the same, and depending on the mechanism used to introduce grooves 104 into body 102, a fewer number of grooves may result in a lesser overall manufacturing cost.

Figure 4B:
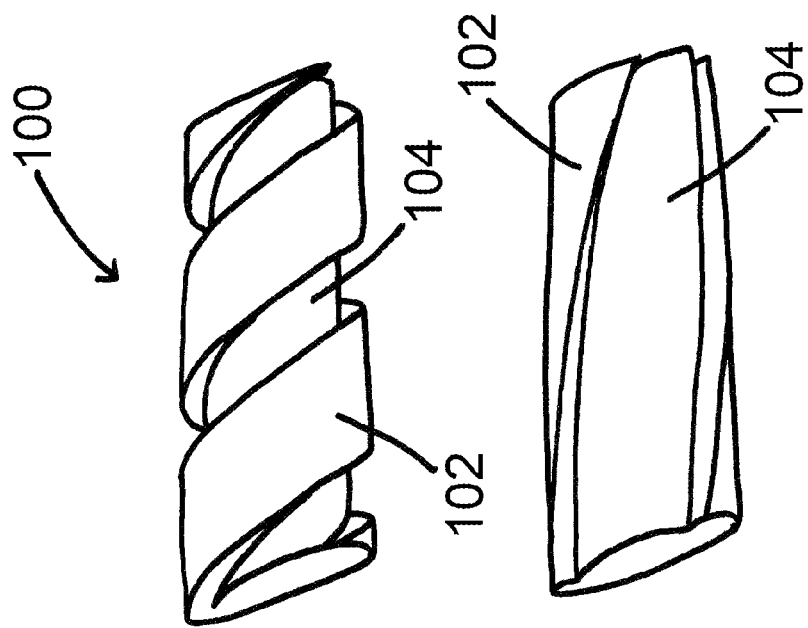
FIGS. 4A and 4B show a series of devices of the present disclosure having various groove pitches, according to an exemplary embodiments of the present disclosure.
Figure 4A:
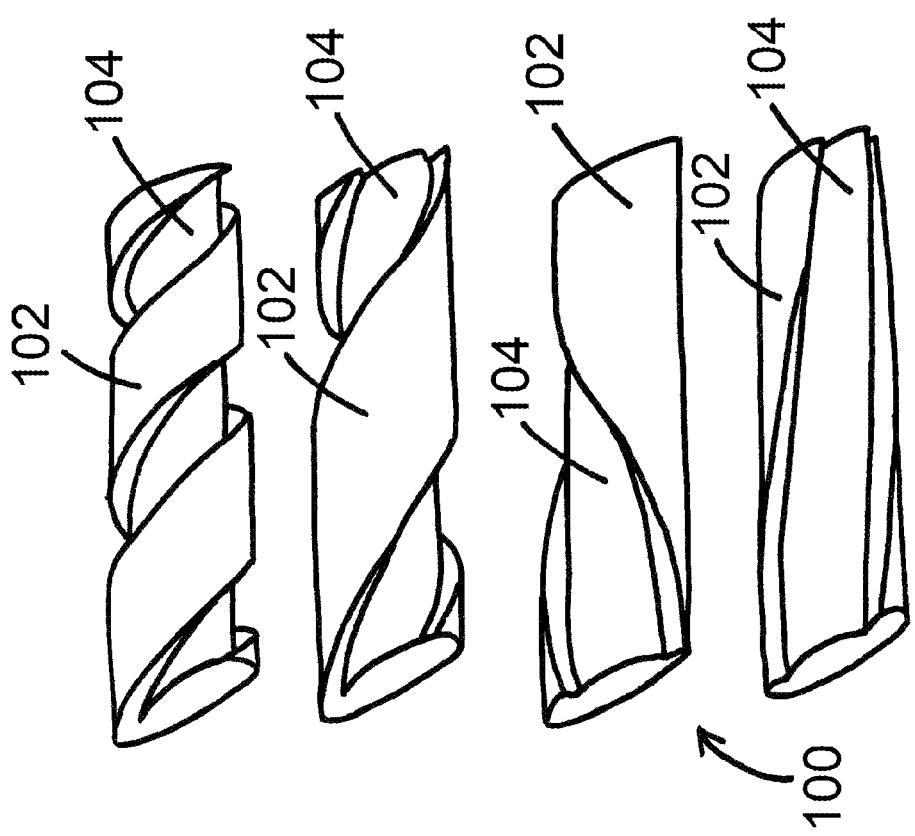

FIGS. 4A and 4B show portions of various exemplary embodiments of devices 100 of the present disclosure having a single groove 104 defined therein. FIG. 4A shows a series of devices 100 having various pitches (the number of turns in a given length), with the smallest pitch (top device 100 device shown therein) of 0.040" and the largest pitch (the bottom device 100 shown in FIG. 4A) of 1.050". The larger the pitch, the more that the groove 104 formed a relatively flat portion of body 102. Additional exemplary device 100 embodiments may have a smaller or larger pitch than those shown in FIGS. 4A and 4B. FIG. 4B shows a closer view of two of the devices 100 shown in FIG. 4A, namely devices 100 having pitches of 0.040" and 1.050", respectively. In various embodiments, devices 100 have pitches between approximately 0.030" and 1.50".

Figure 5B:
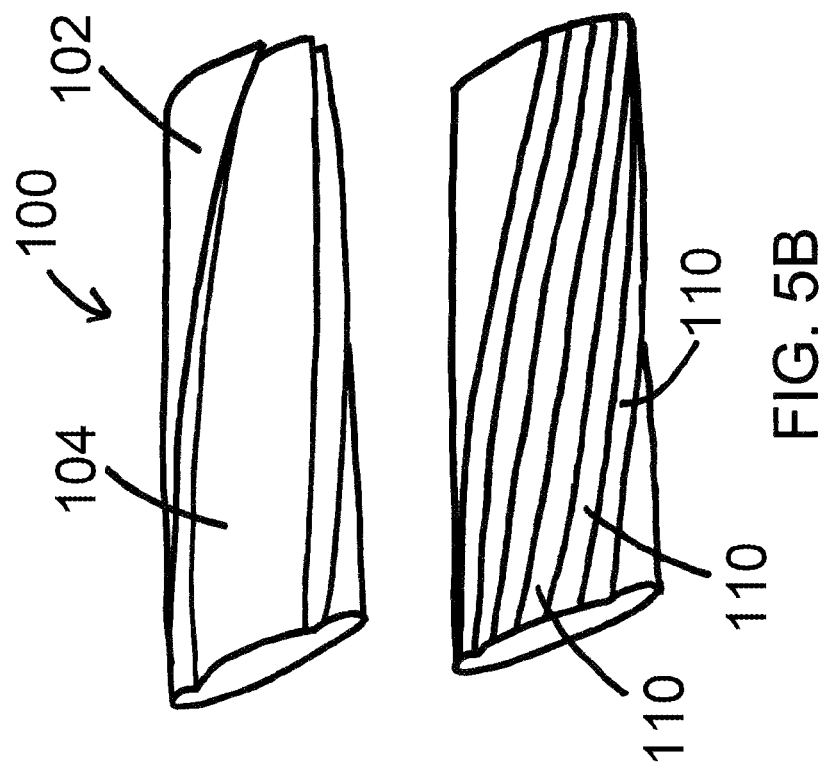
FIGS. 5A and 5B show devices having a single groove with and without a plurality of wires positioned therein, according to an exemplary embodiment of the present disclosure.
Figure 5A:
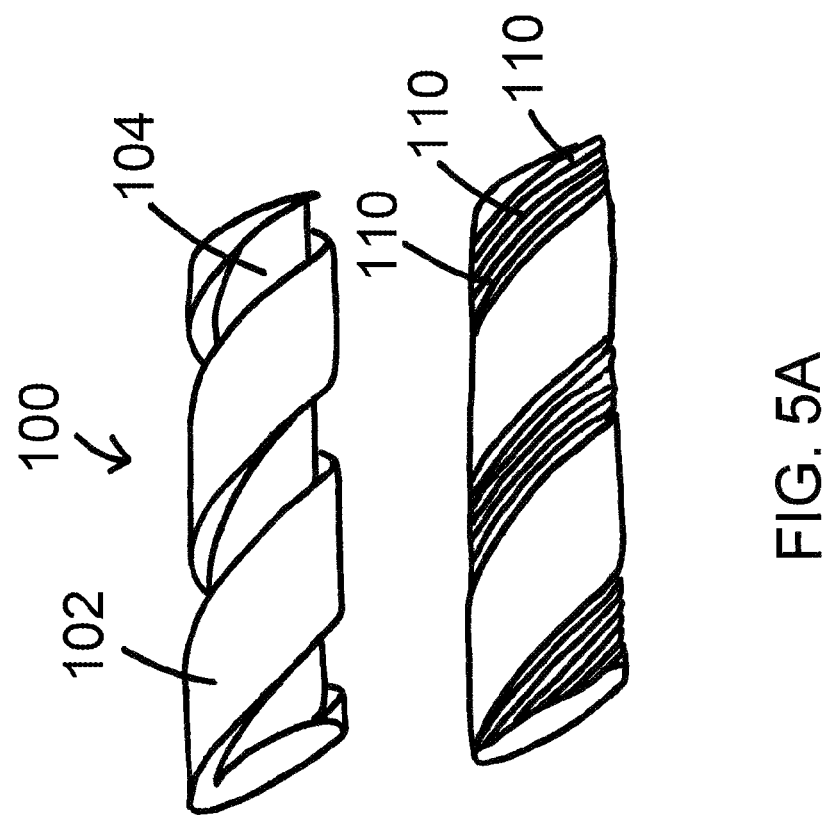

FIGS. 5A and 5B show exemplary devices 100 of the present disclosure. FIG. 5A shows an exemplary device 100 having a 0.040" pitch without (top figure) and with (bottom figure) without conductor wires 110. FIG. 5B shows an exemplary device 100 having a 1.050" pitch without (top figure) and with (bottom figure) conductor wires 110. As shown in FIGS. 5A and 5B, devices 100 have a single groove 104 defined therein, configured to receive a plurality of conductor wires 110 therein. In these exemplary embodiments, six conductor wires 110 are shown therein, whereby conductor wires 110 span a length of device 100.

FIGS. 6A and 6B also show exemplary devices 100 of the present disclosure having a 1.050" pitch, with FIG. 6A showing a device 100 with one groove 104 and FIG. 6B showing a device 100 with multiple grooves 104. In the embodiment shown in FIG. 6A, multiple conductor wires 110 are positioned within one groove 104, and in the embodiment shown in FIG. 6B, a single conductor wire 110 is positioned within each groove 104. In these embodiments, at least part of device 100 is coated with polyethylene terephthalate (PET), and as shown in FIG. 6B, for example, coating 600 is present along device 100 where the conductor wire(s) 110 are positioned within groove 104. Other coatings 600 may be used, as well as various agents 602 used to bond one or more conductor wires 110 to device 100. Other potential coatings 600 include, but are not limited to, thin-walled polymer jackets and various epoxies, and exemplary agents 602 may include, but are not limited to, various epoxies and/or ultraviolet light. As portions of device 100 have an intended use within a patient's body, coatings 500, 600 and/or agents 602, in various embodiments, are used because they are biologically-compatible.

In various embodiments, coatings 500, 600 may be present around core body 102 so to maintain an overall outer diameter although the core itself may be tapered at or near the distal end of body 102. For example, and in at least one embodiment, distal end of body 102 may be tapered down to 0.010" from 0.014", and a coating 500, 600 may be positioned at or near the distal end in greater quantities than at the non-tapered portion so to maintain a consistent overall outer diameter. In other embodiments of devices 100 of the present disclosure, the tapering may be from a first size to a second size, wherein the first size and second size differ from 0.010" and 0.014" as referenced above by way of example. Furthermore, and in various embodiments, the distal end of body 102 is tapered so to increase overall flex of that portion of body 102. Should an increase in overall flex of body 102 in its entirety be desired, the overall outer diameter of body 102 could be decreased. In at least one embodiment, the outer diameter of body 102 is decreased by 0.006" to increase flex.

Figure 6C:
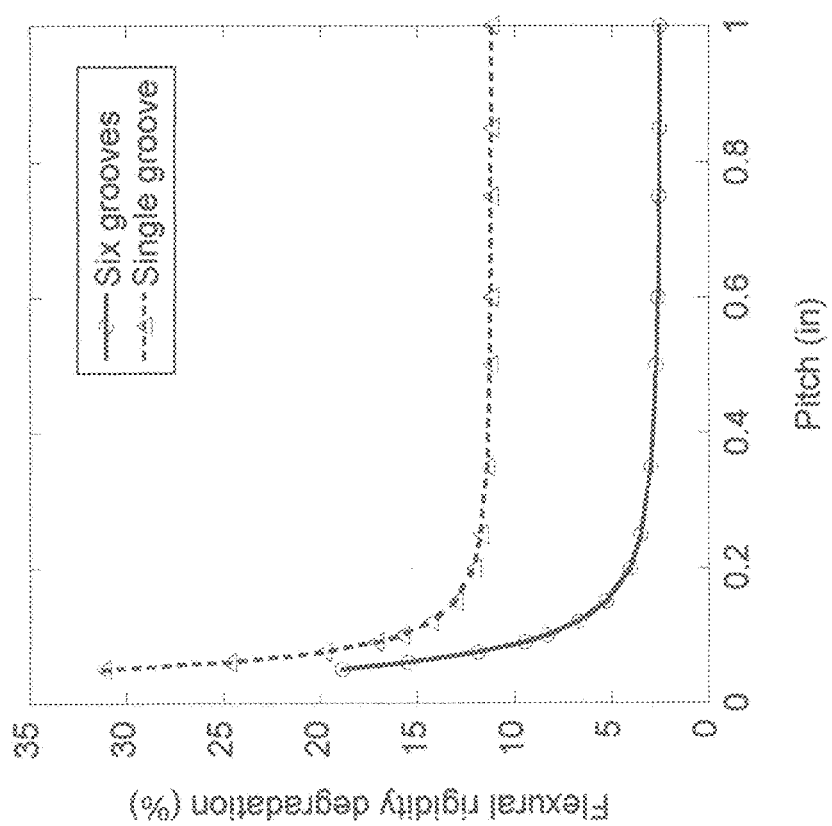
FIG. 6C shows a chart depicting the effect of pitch on the degradation of flexural rigidity, according to exemplary device embodiments of the present disclosure.

FIG. 6C shows a chart depicting the effect of pitch on the degradation of flexural rigidity. As shown in FIG. 6C, device 100 embodiments having a smaller relative pitch have a higher percentage of flexural degradation, noting that the single groove embodiments have a higher relative percentage degradation than the six groove embodiments. For example, a single groove device 100 embodiment having a groove pitch of 0.05" has a 31.17% degradation as compared to an ungrooved wire, while a six groove device embodiment having the same pitch has only a 18.86% degradation.

Figure 7C:
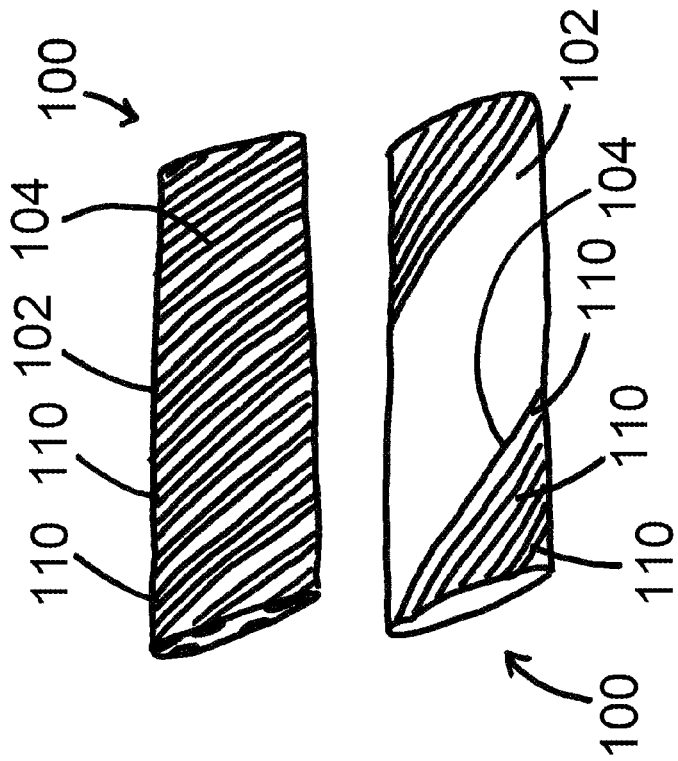
FIGS. 7A-7C show additional devices according to exemplary embodiments of the present disclosure.
Figure 7A:
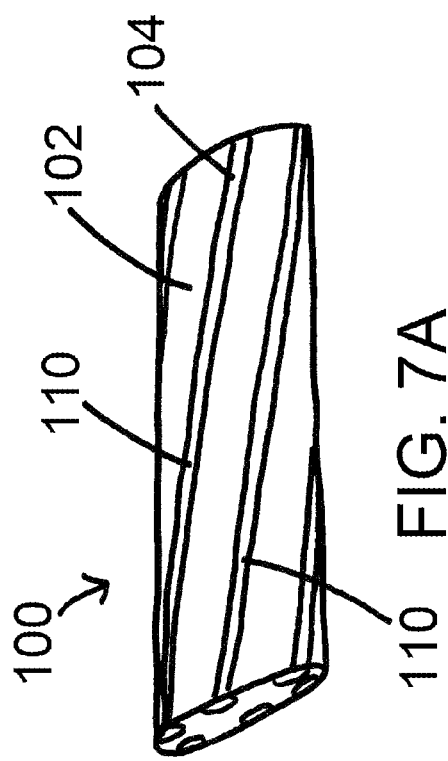
Figure 7B:
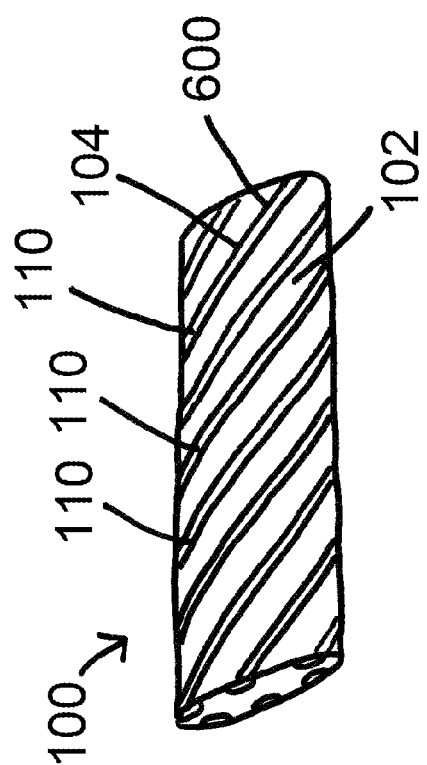

FIGS. 7A and 7B show exemplary devices 100 of the present disclosure having various pitches. In these embodiments, at least part of device 100 is coated with PET, and as shown in FIG. 7B, for example, coating 600 is present along device 100 where the conductor wire(s) 110 are positioned within groove(s) 104. FIG. 7C shows a comparison between an exemplary device 100 of the present disclosure having multiple grooves 104 and a single conductor wire 110 within each groove 104, and an exemplary device 100 of the present disclosure having one groove 104 and multiple conductor wires 110 therein.

FIG. 8A shows a side view of an exemplary device 100 of the present disclosure. As shown in FIG. 8A, device 100 comprises a body 102 having at least one groove 104 defined within at least a part of body 102. In FIG. 8A, groove 104 is shown as being helically defined a relatively central portion of device 100. "Detail A," as shown in FIG. 8A, is a magnified view of a portion of device 100 showing a plurality of conductor wires 110 positioned within groove 104.

FIG. 8A also shows additional components of an exemplary embodiment of device 100 of the present disclosure, including an impedance portion 800 comprising one or more electrodes. As shown in FIG. 8A, four impedance electrodes (mechanically numbered as 1, 2, 3, and 4 below device 100 and labeled with patent application reference numbers 802, 806, 808, 804 above device 100), whereby electrodes 802, 804 comprise the relative two outer electrodes, and wherein electrodes 806, 808 comprise the relative two inner electrodes. Electrodes 802, 804, in at least one embodiment, are referred to as the excitation electrodes, as electrodes 802, 804 are operable to generate an electric field within a luminal organ that can be detected by detection electrodes 806, 808. In at least one embodiment of a device 100 of the present disclosure, device 100 further comprises a temperature portion 810 comprising two thermistor wire ends (mechanically numbered as 5 and 6 below device 100 and labeled with patent application reference numbers 812, 814 above device 100), whereby thermistor wire ends 812, 814 are operable to detect a temperature of a fluid, for example, within a luminal organ at the location of thermistor wire ends 812, 814.

FIG. 8A also shows a compliant portion 820 of device 100 positioned distal to impedance portion 800. Compliant portion 820 is relatively more flexible than the portion of device 100 having groove(s) 104 and wire(s) 110 positioned therein, as compliant portion 820 assists with the potential delivery, positioning, and/or anchoring of device 100 within a luminal organ. An atraumatic tip 822 is present at a distal end of compliant portion 820, in at least one embodiment, of a device 100 of the present disclosure, so to avoid and/or limit the risk of puncture of a luminal organ by device 100.

An exemplary device 100 of the present disclosure also comprises a connection portion 830 located at or near a proximal end of device 100, whereby relative proximal ends of conductor wires 110 may be electrically coupled to a coupler unit 210 such as, for example, current source, a data acquisition and processing system, and/or the like. As shown in FIG. 8A, connection portion 830 includes connectors for each of mechanically numbered items 1-6, which correspond to connectors 832, 834, 836, 838, 840, 842. In at least one embodiment, electrode 802 is coupled to a conductor wire 110 having a connector 832, positioned at or near a proximal end of conductor wire 110. Similarly, electrode 806 corresponds to connector 834, electrode 808 corresponds to connector 836, electrode 804 corresponds to connector 838, thermistor wire end 812 corresponds to connector 840, and thermistor wire end 814 corresponds to connector 842, through one or more connector wires 110.

FIG. 8B shows a cut-away side view of an exemplary portion of a device 100 (along A-A as shown in FIG. 8A) of the present disclosure. As shown therein, an exemplary device 100 has four electrodes, whereby each of electrodes 802, 806, 808, 804, from the distal end to the proximal end, are each effectively coupled to at least one connector wire 110. In at least one embodiment, each of electrodes 802, 806, 808, 804 comprise ring electrodes, noting that non-ring electrodes may also be used. One or more thermistor wire ends 812, 814 may also be coupled to connector wires 110 as shown in FIG. 8B.

In various other embodiments of devices 100 of the present disclosure, devices 100 may have more or fewer electrode and/or wire components. For example, an exemplary device 100 of the present disclosure may have six impedance electrodes and no thermistor, four impedance electrode and one thermistor, three thermistors and no impedance electrodes, and/or more or less electrodes and/or thermistors. In embodiments with more than four impedance electrodes and one thermistor, more connector wires 110 and more connectors would be present within and/or along device 100. In an embodiment of a device 100 with fewer electrodes (or, for example, four electrodes and no thermistor), fewer connectors at the proximal end of device 100 would be required.

In addition, and in at least one embodiment of a device 100 of the present disclosure, body 102 (or a portion thereof) is conductive and can be used in place of a conductive wire 110. For example, an impedance electrode, thermistor, pressure sensor, etc., can be coupled to body 102 at or near the distal end of device 100, and a connector can be coupled to body 102 at the proximal end (or body 102 itself can operate as a connector) in lieu of one or more conductor wires 110. In various embodiments, one or more conductor wires 110 can be used along with body 102 as a conductor.

FIGS. 9A and 9B show cut-away side views of exemplary portions of devices 100 of the present disclosure. As shown in FIG. 9A, a portion of device 100 is shown (along B-B as shown in FIG. 8A) whereby conductor wires 110 are shown positioned within a groove 104 defined within body 102 of device 100. FIG. 9B shows an exemplary connection portion 830 (along C-C as shown in FIG. 8A), whereby conductor wires 110 are coupled to connectors 832, 834, 836, 838, 840, 842. As shown in the magnified view identified as "Detail B" within FIG. 9B, a conductor wire 110 is shown as extending to conductor 832 of device 100.

Figure 10:
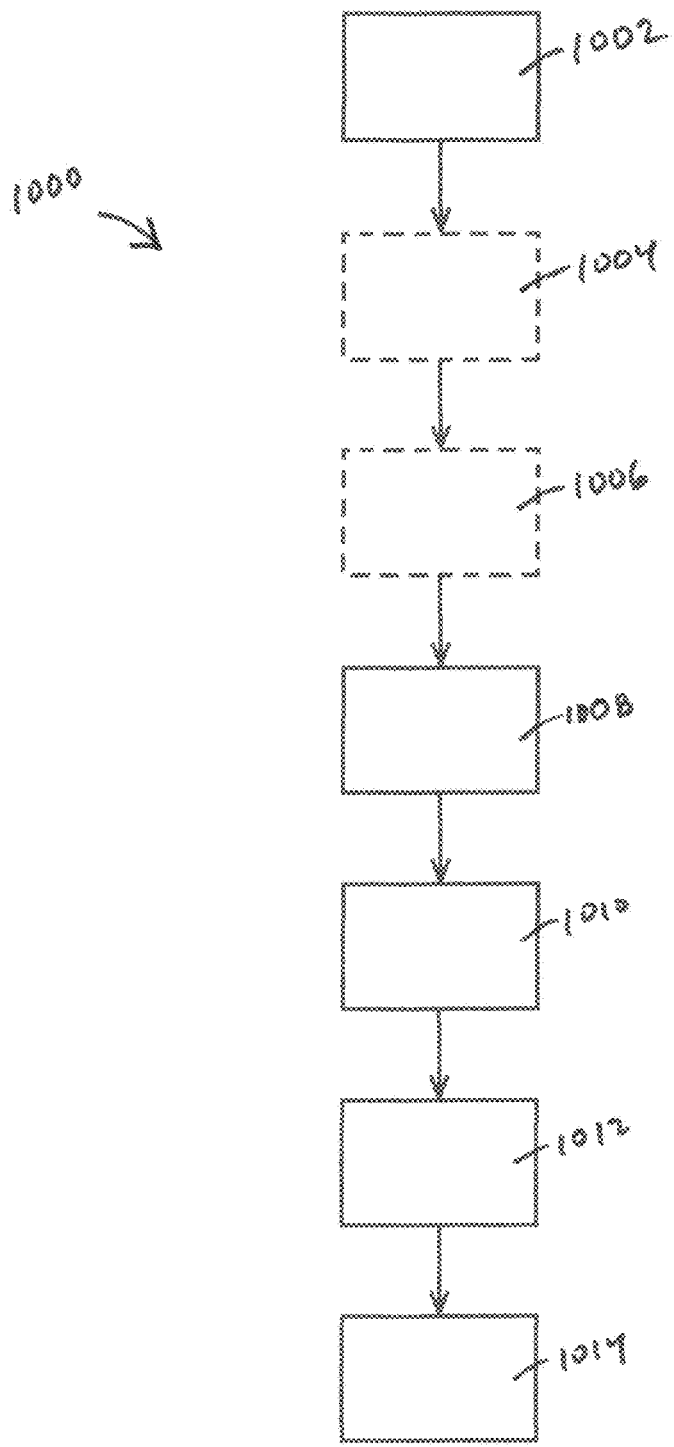
FIG. 10 shows steps of a method of manufacturing a device, according to an exemplary embodiment of the present disclosure.
Figure 11:
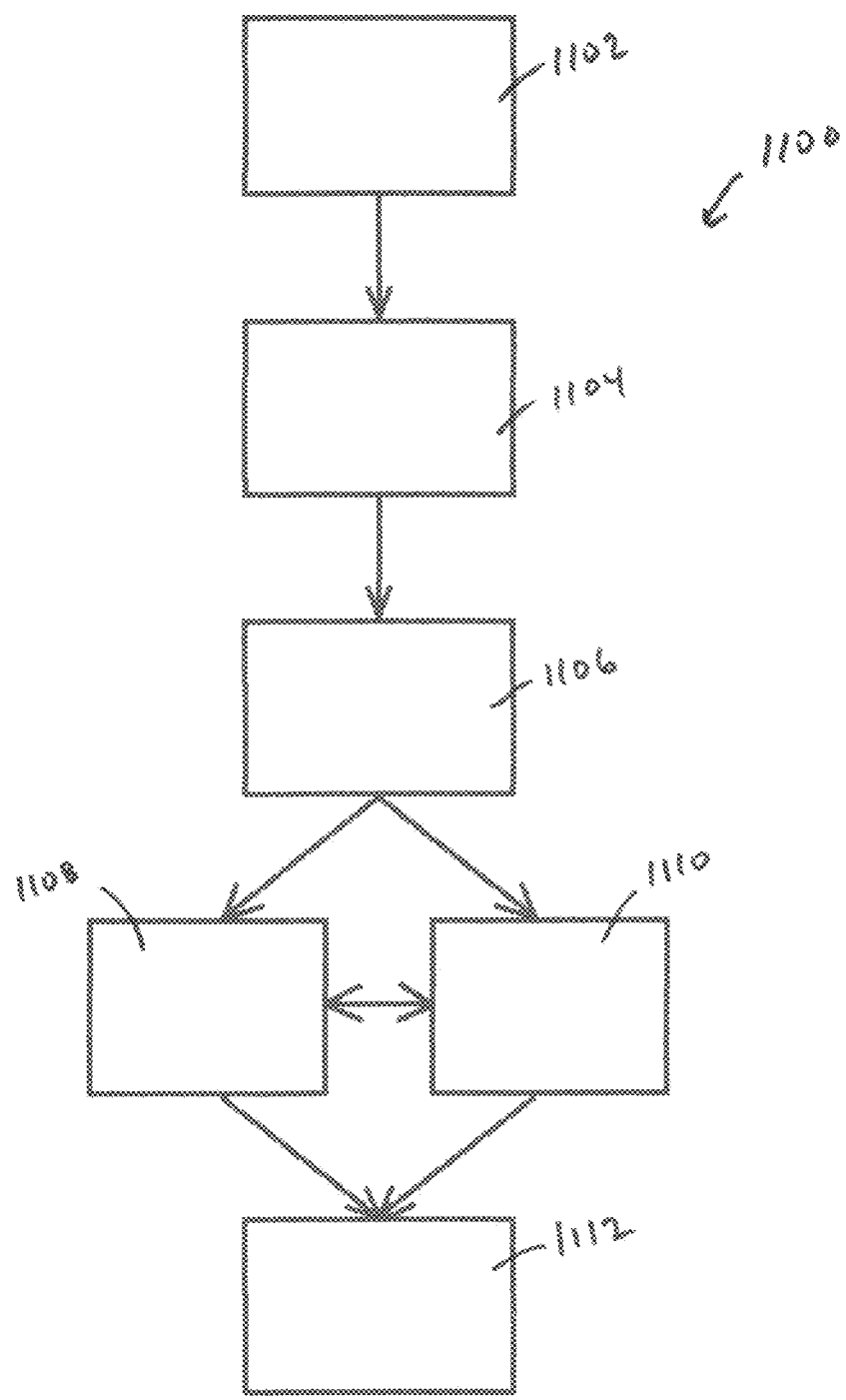
FIG. 11 shows steps of a method of using a device, according to an exemplary embodiment of the present disclosure.

At least one embodiment of a method of manufacturing a device 100 of the present disclosure is shown in the block diagram of FIG. 10. As shown in FIG. 10, method 1000 comprises the step of introducing at least one groove 104 into an elongated body 102 (an exemplary groove introduction step 1002), and optionally applying a coating 500 (as shown in FIG. 2B) of non-conductive material to at least part of body 102 (an exemplary body coating step 1004) so that when a conductor wire 110 is positioned within one or more grooves 104, conductor wires 110 are insulated from body 102 in the event body 102 is conductive. Method 1000 also comprises the step of positioning at least one conductor wire 110 within at least part of groove 104 (an exemplary conductor wire positioning step 1008). An optional step of introducing an adhesive agent 602 to the groove 104 and/or the conductor wire 110 may also be performed prior to performing the exemplary conductor wire positioning step 1008 (an exemplary adhesive application step 1006). Adhesive application step 1006 may also be performed after conductor wire positioning step 1008, whereby agent 602 is applied to the conductor wire 110 after conductor wire 110 is positioned within groove 104.

An exemplary method 1000 may further comprise the step of applying a coating 600 to conductor wire 110 within groove 104 or to the outside of the entire guidewire assembly (device 100) (an exemplary coating step 1010) so to potentially protect conductor wire 110 within groove 104 and/or improve the overall consistency of the outer profile of the portion of device 100 having groove(s) 104 and conductor wire(s) 110 present therein. Such a step may be performed so that when device 100 is introduced into a patient's body, for example, the introduction is smoother as there are less portions of device 100 to potentially get caught and/or injure a luminal organ of a patient.

Method 1000, in at least one embodiment, would comprise the step of applying one or more electrodes 802, 804, 806, 808 and/or connecting one or more thermistor wire ends 812, 814 to device 100 (an exemplary electrode application step 1012). Further, and in at least one embodiment, method 1000 would comprise the step of effectively connecting the one or more electrodes 802, 804, 806, 808 and/or one or more thermistor wire ends 812, 814 to one or more connectors 832, 834, 836, 838, 840, 842 by way of one or more conductor wires 110 (an exemplary connector coupling step 1014).

The present disclosure includes disclosure of a method of using an exemplary device 100 of the present disclosure. In at least one such exemplary method 1100, method 1100 comprises the steps of inserting an exemplary device 100 of the present disclosure into a luminal organ of a patient (an exemplary device insertion step 1102) and advancing device 100 to a desired location within the patient (an exemplary advancement step 1104). Device 100 is then activated by way of applying a current therethrough (an exemplary activation step 1106) and one or more fluid injections may be made so that the fluid passes the various electrodes 802, 804, 806, 808 and/or thermistor electrodes 812, 814 to facilitate any number of impedance readings, such as those to ultimately determine fractional flow reserve (FFR), coronary flow reserve (CFR), cross-sectional area (CSA), and/or temperature readings (an exemplary fluid injection step 1108). The use of fluid injections in connection with an impedance device has been previously described by Kassab et al. in U.S. Pat. No. 7,454,244, and one or more saline injections, for example, as referenced in U.S. Pat. No. 7,454,244 could be performed to obtain impedance readings to be used as referenced herein and as referenced in said patent. Method 1100 may also comprise obtaining one or more impedance readings such as those to ultimately determine FFR, CFR, CSA, and/or temperature, based upon fluid native to the luminal organ and not based upon and introduced bolus of fluid (an exemplary native reading step 1110). Repeating exemplary fluid injection steps 1108 and native reading steps 1110 would generate a series of impedance data that could be used in connection with the aforementioned determinations and/or other determinations, such as potentially diagnosing a disease or disorder, based upon said readings and determinations. Method 1100 may then comprise the step of withdrawing device 100 from the patient (an exemplary device withdrawal step 1112).

Additional device 100 embodiments are also included within the present disclosure. For example, and as shown in FIGS. 12A and 12B, exemplary devices 100 of the present disclosure may incorporate more than one configuration of grooves 104 therein. As shown in FIGS. 12A and 12B, for example, an exemplary device 100 of the present disclosure may have a first portion 1200 of grooves 104 in a first configuration, and may have a second portion 1202 of grooves 104 in a second configuration.

FIG. 12A shows an exemplary device 100 of the present disclosure, wherein the first portion 1200 has one or more grooves 104 in a clockwise spiral configuration as viewed from the distal end of device 100, an exemplary first configuration, and wherein the second portion 1202 has one or more grooves 104 in a counter-clockwise spiral configuration, an exemplary second configuration. Such an alternating configuration of grooves in opposite spiral directions, in at least one embodiment, helps to cancel the negative effects of device 100 whip and improve overall torque transfer.

Torque transfer, as referenced herein, relates to the ability of a device to transmit a turning (torque) from one portion of a device to another. For example, and if considering an elongated device 100 having a length, torque transfer can relate to a physical turning at or near a proximal end of device 100 that is transmitted to a distal end of device 100. For example, if the proximal end of an exemplary device 100 was turned clockwise 90°, and if the distal end of device 100 also turned 90°, there would be 100% torque transfer. However, if the proximal end of device 100 was turned clockwise 90° and the distal end only turned 45°, the torque transfer would only be 50%.

Whip, as referenced herein, relates to a second portion of a device "catching up" to the turning engagement, for example, of a first portion of the device. For example, if turning a proximal end of a device 180° only initially results in the distal end turning 135° (a 75% torque transfer), and turning the proximal end of the device an additional 90° (for a total of 270°) causes to distal end to turn an additional 180° (also for a total of 270°), that latter distal end rotation is referred to as a whip, as the rotation of the distal end effectively "catches up" with the rotation at the proximal end. Whip can also refer to overcompensation of the second portion due to rotation of the first portion. For example, and in the example referenced above, if the additional proximal end turning of 90° (for a total turning of 270°) results in the distal end turning an additional 180° (for a total of 315°), the whip caused the distal end to overcompensate by an extra 45°. A "perfect" device 100, as referenced herein, would have perfect torque transfer and zero whip.

FIG. 12B shows an exemplary embodiment of a device 100 of the present disclosure, wherein the first portion 1200 has one or more grooves 104 in a counter-clockwise spiral configuration, and wherein the second portion 1202 has one or more grooves 104 in a clockwise spiral configuration. Additional device 100 embodiments are shown in FIGS. 12C and 12D, wherein one of the portions (1200 or 1202) has a spiral configuration, and wherein the other portion (1200 or 1202) has a straight configuration. Various device 100 embodiments of the present disclosure may have a first portion 1200 and second portion 1202 with different configurations.

FIG. 13A shows an exemplary embodiment of a device 100 of the present disclosure, whereby device 100 has a first portion 1200, a second portion 1202, and a third portion 1300, with at least one portion 1200, 1202, 1300 having a different configuration than the remaining portions. In FIG. 13A, for example, device 100 has a first portion 1200 has one or more grooves 104 in a clockwise spiral configuration, a second portion 1202 with one or more grooves 104 in a counter-clockwise spiral configuration, and a third portion 1300, in between first portion 1200 and second portion 1202, with one or more grooves 104 in a straight configuration. FIG. 13B shows an exemplary device 100 embodiment, whereby a first portion 1200 has one or more grooves 104 in a counter-clockwise spiral configuration, a second portion 1202 with one or more grooves 104 in a clockwise spiral configuration, and a third portion 1300, in between first portion 1200 and second portion 1202, with one or more grooves 104 in a straight configuration. FIG. 13C shows a device 100 embodiment having straight, clockwise, and counterclockwise groove 104 configurations, and FIG. 13D shows a device 100 embodiment having straight, counterclockwise, and clockwise groove 104 configurations. Other embodiments of devices 100 of the present disclosure may have additional portions with various configurations of straight, clockwise, and/or counter-clockwise groove 104 configurations, such as those with four or more portions.

Figure 14A:
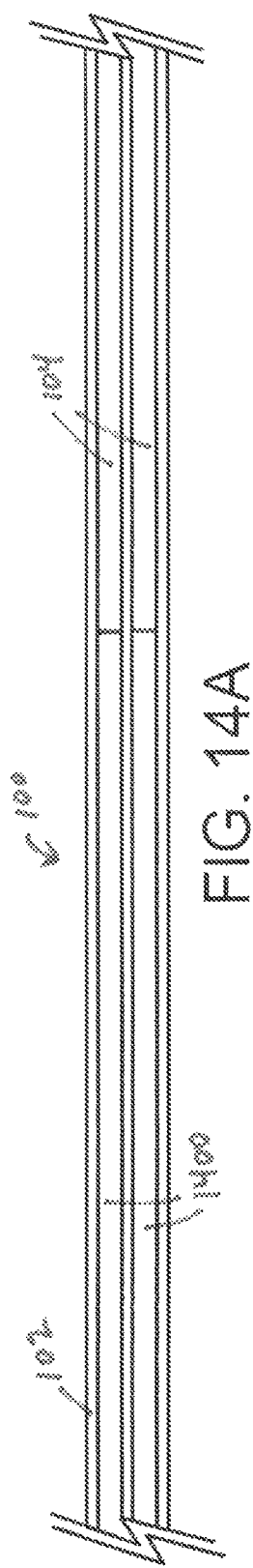
FIG. 14A shows a side view of a device with grooves and a conductive polymer positioned therein, according to an exemplary embodiment of the present disclosure.

FIG. 14A shows an additional device 100 embodiment of the present disclosure. As shown in FIG. 14A, device 100 comprises a body 102 having a plurality of grooves 104 defined therein. In at least one groove 104 (noting that the exemplary device 100 embodiment may have a single groove 104 instead of a plurality of grooves 104), a conductive polymer 1400 is placed therein, and is used to transmit the signal to and/or from one or more sensors (such as the electrodes and/or thermistors referenced herein). In a number of embodiments referenced herein, the signal(s) is/are is transmitted using one or more conductor wires 110 placed within groove(s) 104, and in the embodiment shown in FIG. 14A, a conductive polymer 1400 is used instead of one or more conductor wires 110. Conductive polymer 1400, as shown in FIG. 14A, is shown only within part of grooves 104 (so that conductive polymer 1400 can be visualized in the figure as being different from grooves 104), but in various actual embodiments, conductive polymer 1400 would need to extend from the sensors to the connection portion 830, for example, so that a signal can be transmitted over that distance.

Figure 14B:
FIGS. 14B, 14C, and 15A show side views of a device with clockwise and counter-clockwise groove configurations, according to exemplary embodiments of the present disclosure.
Figure 14C:

FIG. 14B shows an exemplary device 100 embodiment with a plurality of grooves 104 defined therein. As shown in FIG. 14, the body 102 of device 100 has one or more grooves 104 in a clockwise spiral configuration and also has one or more grooves 104 in an opposing counter-clockwise spiral configuration. One or more conductor wires 110 (as shown in FIG. 14A, or alternatively a conductive polymer 1400) can be positioned within one of the groove configurations, such as the clockwise configuration shown in FIG. 14A, and can be used to conduct signals as referenced herein. Such an opposing groove 104 configuration, in at least one device 100 embodiment, is defined within the body 102 of device 100 so to balance overall torque transfer and/or reduce instances of device 100 whip. FIG. 14C shows another exemplary device 100 embodiment of the present disclosure, whereby conductor wires 110 (or alternatively, a conductive polymer 1400) is positioned within one of the groove configurations (clockwise or counter-clockwise), and whereby a coating 500 (or coating 600, as the case may be) is positioned in the other groove configuration to help further balance overall torque transfer and/or reduce instances of device 100 whip. Coating 500, 600, in various embodiments, may comprise various polymers, epoxies, adhesives, and/or other materials capable of being placed within one or more grooves 104 and not interfering with conductive wires 110 and/or conductive polymers 1400 placed in other grooves and/or positioned about a surface of an exemplary device 100.

Figure 15A:
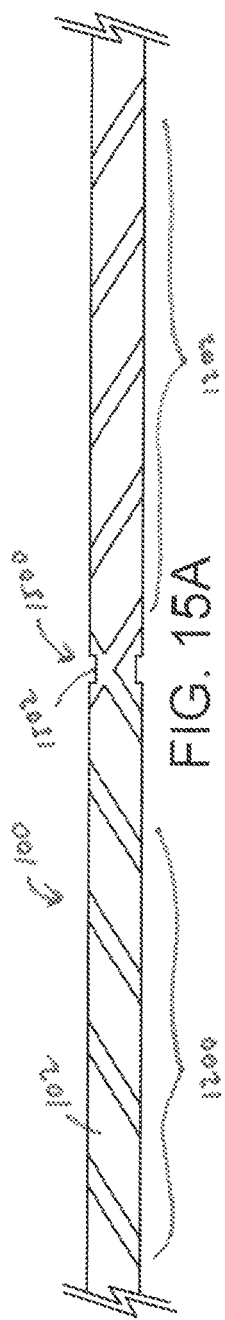
Figure 15B:
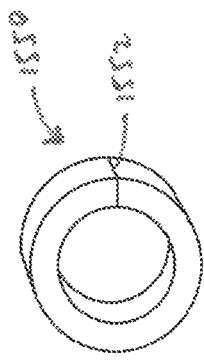
FIG. 15B shows a coupler configured to fit around a device, according to an exemplary embodiment of the present disclosure.

An additional device 100 embodiment of the present disclosure is shown in FIG. 15A. As shown therein, device 100 comprises a first portion 1200 having one or more grooves 104 in a clockwise spiral configuration (as viewed from the distal end of device 100), and a second portion 1202 has one or more grooves 104 in a counter-clockwise spiral configuration. The one or more grooves 104 of first portion 1200 and second portion 1202 are in communication with one another at a coupler portion 1500, so that one or more conductor wires 100 positioned within grooves 104 can extend from first portion 1200 to second portion 1202. Coupler portion 1500, as shown in FIG. 15A, can include one or more notches 1502 defined therein, such as the circumferential notch 1502 as shown in the figure. To facilitate placement of conductor wires 110 within grooves 104, a portion of conductor wires 110 can be positioned, for example, within groove(s) 104 of first portion 1200, and can be held in place at coupler portion 1500 using a coupler 1550, such as coupler 1550 shown in FIG. 15B. Coupler 1550, as shown in FIG. 15B, may open and close at contact 1552, so that coupler 1550 can be positioned around body 102 and closed to hold conductor wires 110 in place. Conductor wires 110 can then be positioned within groove(s) 104 of second portion 1202, noting that the change in rotation of grooves 104 (or change to/or from a straight to/from a spiral configuration) would not negatively affect conductor wire 110 positioning as coupler 1550 would sufficiently hold conductor wires 110 in place.

Figure 15C:
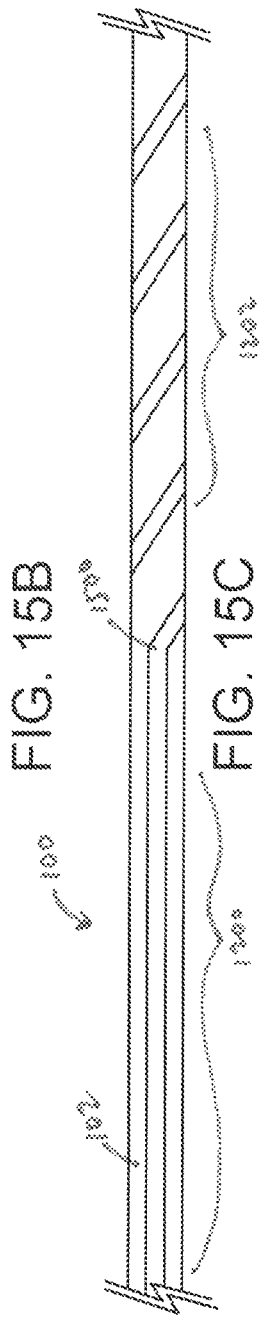
FIGS. 15C and 15D show side views of devices with two groove configurations, according to exemplary embodiments of the present disclosure.
Figure 15D:
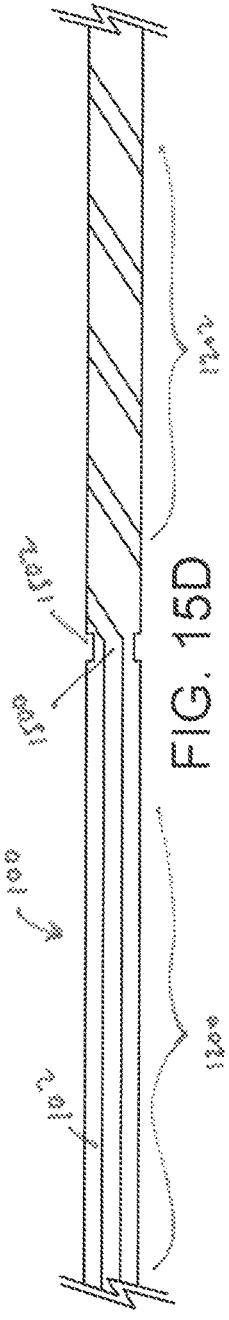

FIGS. 15C and 15D show additional device 100 embodiments, whereby grooves 104 defined therein are effectively coupled (or in communication with) each other between the first portion 1200 and the second portion 1202 of said devices. As shown in FIG. 15C, device 100 comprises a first portion 1200 with a straight configuration of grooves 104, and a second portion 1200 with a counter-clockwise configuration of grooves therein, whereby grooves 104 of each portion 1200, 1202 are in communication with each other at coupler portion 1500. FIG. 15D shows a similar device 100 embodiment, but the second portion 1202 has a clockwise groove 104 configuration, and coupler portion 1500 includes a notch 1502 configured to receive a coupler 1550 to hold conductor wires 110 in place. Additional embodiments are also possible, with various configurations and numbers of portions, including those with multiple coupler portions 1500 with optional multiple notches.

The present disclosure also includes disclosure of device 100 whereby one or more conductive portions may be initially formed on a separate substrate and subsequently added to the body 102 of device 100. In at least one embodiment, and as shown in FIG. 16A, an impedance substrate 1600 may be initially separate from device 100, and subsequently added to device 100 to form an operable impedance device 100. In at least one embodiment, impedance substrate 1600 is configured to fit around at least part of an elongated body (such as a body 102) sized and shaped to fit within a mammalian body lumen.

As shown in FIG. 16A, impedance substrate 1600 comprises a flexible material 1602 capable of having conductors and electrodes positioned thereon and/or defined therein. In FIG. 16A, an exemplary impedance substrate 1600 has an impedance portion 800 (including electrodes 802, 804, 806, 808, for example) positioned thereon, along with temperature portion 810 with two thermistor wire ends 812, 814 thereon as well. Said items are coupled to at least one conductor wire 110 as shown on FIG. 16A, with conductor wires 110 terminating at or near a proximal end 1602 of impedance substrate 1600. Other embodiments of impedance substrates 1600 of the present disclosure may, for example, comprise only an impedance portion 800 with conductor wires 110, or comprise only a temperature portion 810 with conductor wires 110. In various embodiments, the impedance portion 800, temperature portion 810, and/or the conductor wires 110 are deposited and/or printed on the impedance substrate 1600, as desired.

An exemplary impedance substrate 1600, such as shown in FIG. 16A, may be used in connection with an exemplary device 100 of the present disclosure as shown in FIGS. 16B and 16C. As shown in FIG. 16B, a body 102 of an exemplary device 100 may have a series of grooves 104 defined therein and one or more conductor wires 110 positioned therein. In other embodiments, device 100 would not need to have any grooves 104 defined therein, but would instead include one or more conductor wires 110 adjacent to the body 102 of device 100, so that said conductor wires 110 can contact the conductor wires 110 of impedance substrate 1600.

Conductor wires 110 may then terminate at or near the proximal end 1602 of impedance substrate 1600 when impedance substrate 1600 is positioned thereon as shown in FIG. 16C. FIG. 16C shows an exemplary impedance substrate 1600 positioned relative to body 102 but not yet wrapped around body 102, and FIG. 16D shows an exemplary impedance substrate 1600 wrapped around body 102 to form an operable impedance device 100. To allow for such wrapping, impedance substrate 1600 must be sufficiently flexible and sufficiently thin so not to detrimentally increase the overall diameter of device 100.

As referenced above, electrodes 802, 804, 806, 808 may be positioned differently in various embodiments. As generally referenced herein, electrodes 802 and 804 are the outer, excitation electrodes, and electrodes 806 and 808 are the inner, detection electrodes. In various embodiments, electrode 802 may be the most distal electrode, and in other embodiments, electrode 804 may be the most distal electrode, out of electrodes 802, 804, 806, 808.

Similarly, the present disclosure also includes disclosure of device 100 whereby one or more connectors may be initially formed on a separate substrate and subsequently added to the body 102 of device 100. In at least one embodiment, and as shown in FIG. 16E, a connector substrate 1675 may be initially separate from device 100, and subsequently added to device 100 to form an operable (or potentially operable) impedance device 100.

As shown in FIG. 16E, connector substrate 1675 comprises a flexible material substrate 1685 capable of having connectors positioned thereon and/or defined therein. In FIG. 16E, an exemplary connector substrate 1675 includes a connection portion 830 with connectors 832, 834, 836, 838, 840, 842 positioned thereon. Said connectors are coupled to at least one conductor wire 110 as shown on FIG. 16E, with conductor wires 110 terminating at or near a distal end 1680 of connector substrate 1675. Other embodiments of connector substrate 1675 of the present disclosure may, for example, comprise fewer or more connectors, whereby said connectors correspond to one or more sensors/electrodes at another portion of device 100. In various embodiments, the connectors are deposited and/or printed on the connector substrate 1675, as desired.

An exemplary connector substrate 1675, such as shown in FIG. 16E, may be used in connection with an exemplary device 100 of the present disclosure as shown in FIGS. 16F and 16G. As shown in FIG. 16F, a body 102 of an exemplary device 100 may have a series of grooves 104 defined therein and one or more conductor wires 110 positioned therein. In other embodiments, device 100 would not need to have any grooves 104 defined therein, but would instead include one or more conductor wires 110 adjacent to the body 102 of device 100, so that said conductor wires 110 can contact the conductor wires 110 of connector substrate 1675.

Conductor wires 110 may then terminate at or near the distal end 1680 of connector substrate 1675 when connector substrate 1675 is positioned thereon as shown in FIG. 16G. FIG. 16G shows an exemplary connector substrate 1675 positioned relative to body 102 but not yet wrapped around body 102, and FIG. 16H shows an exemplary connector substrate 1675 wrapped around body 102 to form an operable (or potentially operable) impedance device 100. To allow for such wrapping, connector substrate 1675 must be sufficiently flexible and sufficiently thin so not to detrimentally increase the overall diameter of device 100. FIG. 16I shows an exemplary device of the present disclosure having a body 102, conductor wires 110 along body 102 (within grooves 104 and/or positioned adjacent to body 102 not within grooves 104), an exemplary impedance substrate 1600 positioned at or near the distal end of body 102 and wrapped around body 102, and a connector substrate 1675 positioned at or near the proximal end of body 102 and wrapped around body 102. Such a device 100 embodiment would entail the preparation of two flexible substrates with the various sensors/electrodes/connectors positioned thereon.

So that impedance substrate 1600 and/or connector substrate 1675 remain(s) coupled to body 102, an adhesive 1650 (or an adhesive 602) may be positioned on the back of impedance substrate 1600, connector substrate 1675, and/or about body 102, or a portion of impedance substrate 1600 and/or connector substrate may be heated and pressed onto body 102 so that when the substrate cools, it remains coupled to body 102. In addition, various elements of impedance substrate 1600 (such as electrodes and other sensors) may be positioned onto impedance substrate 1600 using an adhesive 1650, 602, such as a non-metallic epoxy or a silver epoxy, for example. Connectors may be coupled to connector substrate 1675 in a similar fashion.

Figure 17A:
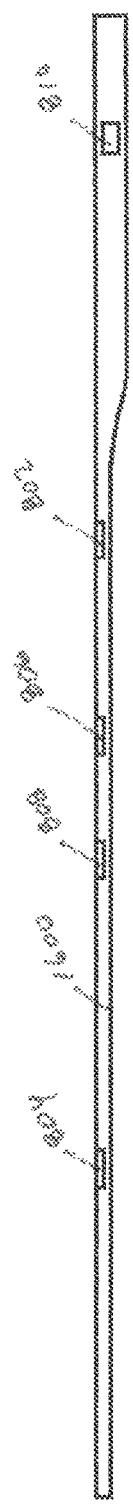
FIG. 17A shows an impedance substrate having a relatively larger size near a temperature portion, according to an exemplary embodiment of the present disclosure.

A side view of an exemplary impedance substrate 1600 of the present disclosure is shown in FIG. 17A. As shown therein, an exemplary impedance substrate 1600 has electrodes 802, 804, 806, 808 positioned thereon or defined therein, as well as a temperature portion 810 positioned thereon or defined therein. In at least one embodiment, temperature portion 810 (such as a thermistor, for example), is physically larger than electrodes 802, 804, 806, 808, and therefore requires more impedance substrate 1600 at temperature portion 810. So that such an embodiment may still be wrapped around a portion of an exemplary device 100 of the present disclosure and maintain a desired outer dimension, device 100 may be tapered at taper 1700 shown in FIG. 17B, so that a proximal body portion 1702 has a relatively larger cross-sectional area than a distal body portion 1704 distal to taper 1700. In such an embodiment, a relatively larger portion of impedance substrate 1600 would be positioned about body 102 at or distal to taper 1700, so that when impedance substrate 1600 is wrapped around body 102, desired device 100 outer dimensions are achieved. Taper 1700, in at least one embodiment, is configured so that a portion of conductor wires 110 positioned within body 102 (such as those within one or more grooves 104 or otherwise embedded within body 102) can be "released" and subsequently connected to one or more sensors/electrodes as desired. In at least one embodiment the taper 1700 would cause the distal body portion 1704 to have a cross-sectional area down to 0.004" to 0.005" from an initial cross-sectional area of, for example, 0.014" or 0.035".

Figure 17B:
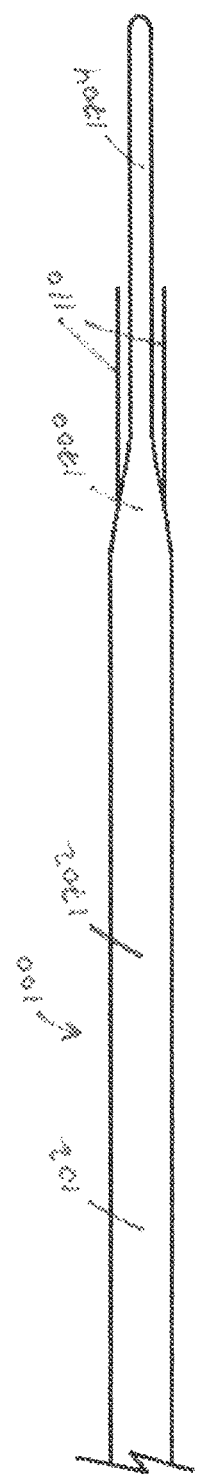
FIG. 17B shows a core body having a tapered portion, according to an exemplary embodiment of the present disclosure.
Figure 17C:
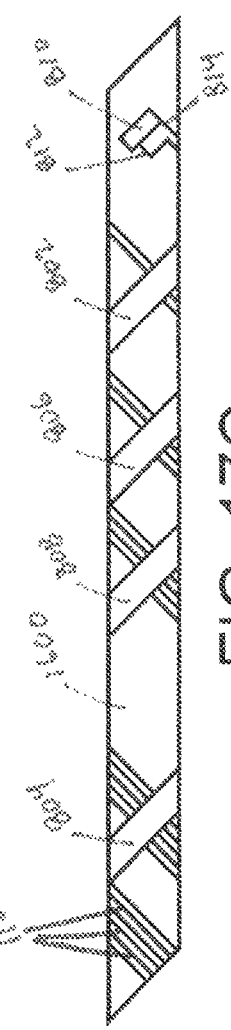
FIG. 17C shows an impedance substrate configured for coiling around a core body, according to an exemplary embodiment of the present disclosure.

An additional impedance substrate 1600 of the present disclosure is shown in FIG. 17C. Such an embodiment, as shown in FIG. 17C, is configured so that it can be wound about a portion of a body 102 of a device 100 of the present disclosure, so that when wound, conductor wires 110 properly contact one another across impedance substrate 1600, and wherein electrodes 802, 804, 806, 808 and/or temperature portion 810 are properly aligned so that they operate as desired. As shown in FIG. 17C, an exemplary impedance substrate 1600 may have an angled proximal end 1750 and/or an angled distal end 1752, so that when impedance substrate 1600 is wound about a body 102, proximal end 1750 and distal end 1752 are perpendicular to the longitudinal axis of body 102. As referenced herein, various embodiments of impedance substrates 1600 and/or connector substrates 1675 may be used in connection with various devices, including devices 100 of the present disclosure having grooves 104 therein, or other wires or catheters with or without grooves 104 defined therein.

Figure 17D:
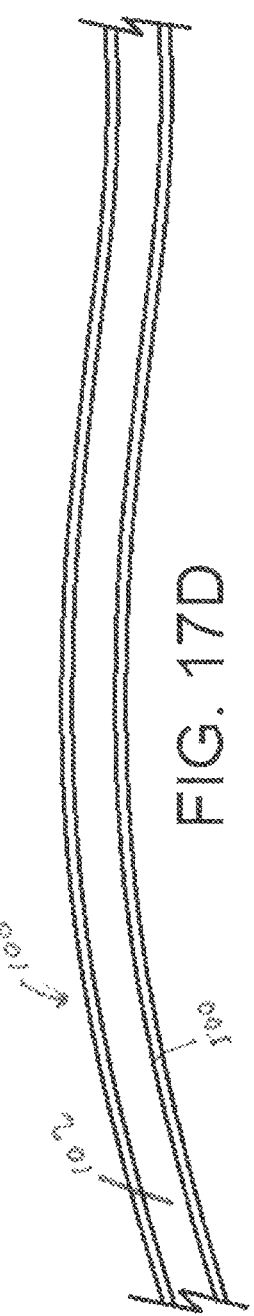
FIG. 17D shows a device having a curvature and a coating positioned thereon, according to an exemplary embodiment of the present disclosure.

Various device 100 embodiments of the present disclosure may have a coating 500 (or 600) positioned thereon, such as shown in FIG. 17D. As shown in FIG. 17D, coating 500, 600 is sufficiently flexible so that when body 102 of device 100 is curved/bent, coating 500, 600 remains sufficiently about body 102. In addition, coatings 500, 600 that are sufficiently flexible so not to negatively impact torque transfer and/or increase the instance of whip are preferred, either by their material composition, amount of coating, or both.

FIGS. 18A and 18B show an exemplary assembly 1800 of conductor wires 110 useful with exemplary devices 100 of the present disclosure. FIG. 18A shows a cross-sectional end view of an exemplary assembly, whereby the individual conductor wires 110 are insulated/separated from one another using an exemplary coating 500 (or 600) of the present disclosure. Such an assembly 1800 allows all conductor wires 110 (such as two, four, six, or another number of conductor wires 110) to be positioned within a groove 104 of a body 102 of a device 100, such as the portion of a device 100 shown in FIG. 18B. FIG. 18B shows a top view of such a device 100, whereby assembly 1800, including the desired number of conductor wires 110, is positioned within a groove 104.

Figure 19A:
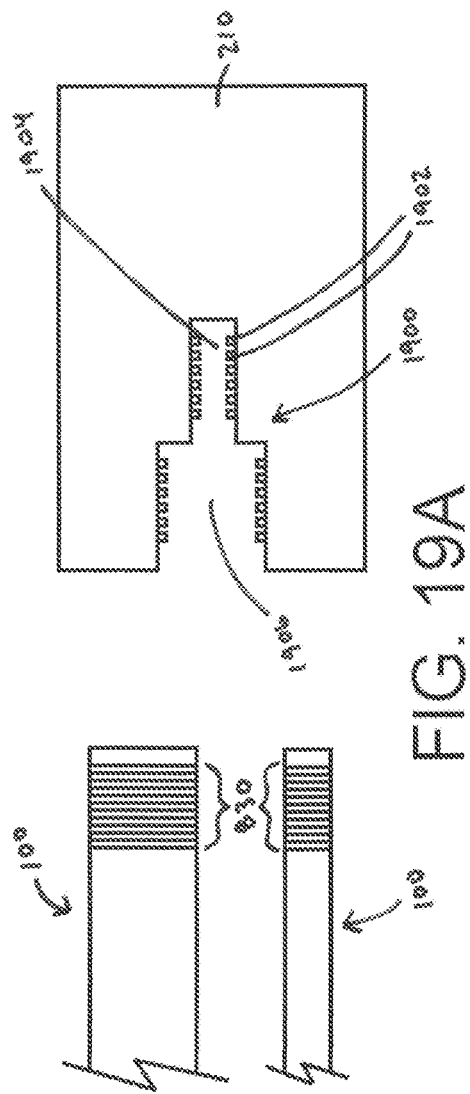
FIG. 19A shows the proximal ends of two devices positioned relative to a coupler unit, according to an exemplary embodiment of the present disclosure.
Figure 19B:
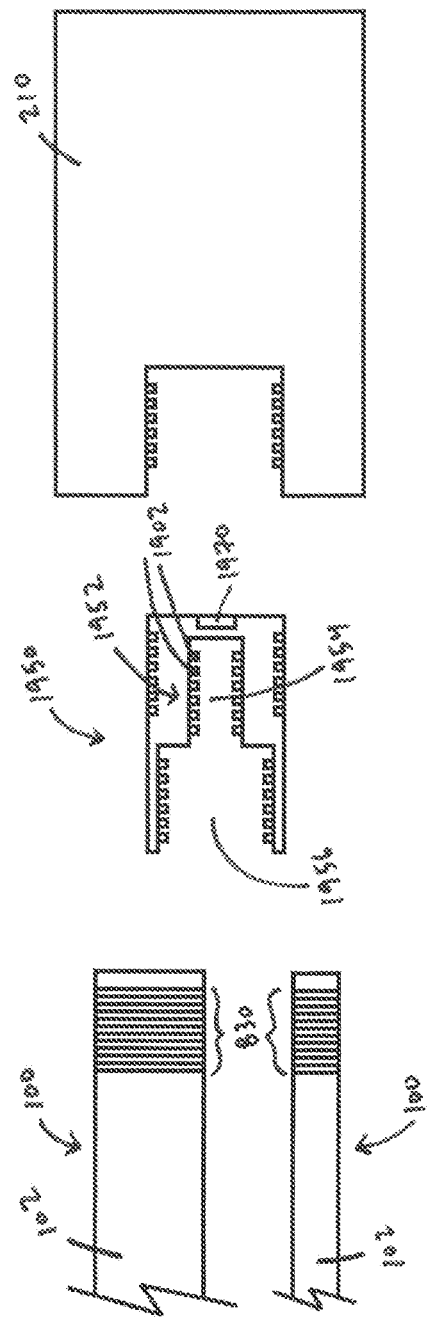
FIG. 19B shows the proximal ends of two devices and an adapter positioned relative to a coupler unit, according to an exemplary embodiment of the present disclosure.

FIGS. 19A and 19B show exemplary embodiments of coupler units 210 of the present disclosure, such as, for example, a console, a current source, a data acquisition and processing system, and/or the like, configured to receive various devices 100 of the present disclosure and/or connectors configured to receive various devices 100 of the present disclosure. FIG. 19A shows the proximal ends of two exemplary devices 100 of the present disclosure (such as, for example, devices with a 0.014" and a 0.035" outer diameter) with connection portions 830 shown thereon. Coupler unit 210, as shown in FIG. 19A, may have a tiered receptacle 1900 having connector receivers 1902 therein, so that when a smaller outer diameter device 100 is inserted, the inner portion 1904 of tiered receptacle 1900 would receive the device 100, and so that when a larger outer diameter device 100 is inserted, the outer portion 1906 of tiered receptacle 1900 would receive the device 100. The connection portion 830 of the inserted device would then contact a particular set of connector receivers 1902, which would signal to the coupler unit that a device 100 of a particular size has been inserted. Coupler units 210 may, in various embodiments, use a different set of settings, formulas, and/or offsets depending on the size of the device 100 inserted, so that more accurate measurements may be obtained using a device 100 of a particular size.

FIG. 19B shows an embodiment of a coupler unit 210 configured to receive an adapter 1950, whereby adapter 1950 is itself configured to receive proximal ends of one or more devices 100 of different sizes. As shown in FIG. 19B, adapter 1950 has a tiered receiver portion 1952, whereby an inner portion 1954 of tiered receiver portion 1952 is configured to receive a smaller outer diameter device 100, and further has an outer portion 1956 configured to receive a larger outer diameter device. A set of adapter connector receivers 1902 would then contact a connection portion 830 of a device and coupler unit 210 would then know the size of the device 100 depending on which set of adapter connector receivers 1902 contacts connection portion 830 of device 100. External connectors 1960 of adapter 1950, in at least one embodiment and when in contact with coupler unit 210, could be used to transmit one or more signals from adapter 1950 to coupler unit 210 by way of connector receivers 1902 of coupler unit 210. In at least one embodiment, and as shown in FIG. 19B, adapter 1950 may have a memory portion 1970, whereby memory portion 1970 could store various parameters, settings, formulas, offsets, and the like, for use with coupler unit 210.

Figure 20A:
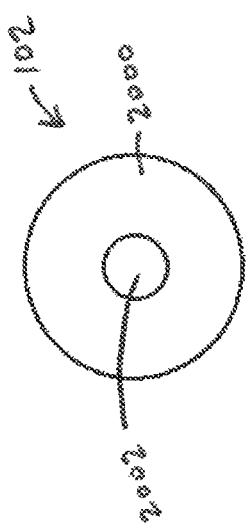
FIG. 20A shows a cross-sectional view of a device having a first portion surrounding a second portion, according to an exemplary embodiment of the present disclosure.
Figure 20B:
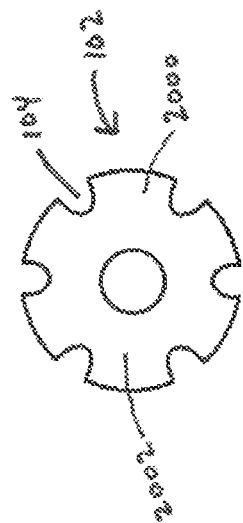
FIG. 20B shows a cross-sectional view of a device having a first portion surrounding a second portion and grooves formed in the first portion, according to an exemplary embodiment of the present disclosure.

In addition to the foregoing, the present disclosure includes various device 100 embodiments comprising different body 102 materials other than those previously described. For example, and in at least one embodiment, an exemplary device 100 of the present disclosure could comprise a body 102 comprising a flexible polymer (such as an epoxy, a polyimide (such as Kapton), and/or another polycarbon) combined with carbon fiber, so that the body 102 would have the strength and durability of carbon fiber, but the added benefit of being more flexible than only a carbon fiber body 102 due to the epoxy and/or one or more additional polycarbons. So to minimize or eliminate the concerns with potential device 100 breakage, a portion of device 100 could be reinforced with a metallic member, such as a metallic wire. An exemplary cross-section of such an embodiment is shown in FIG. 20A, whereby body 102 comprises a first portion 2000 (comprising carbon fiber combined with epoxy and/or one or more other polycarbons) and a second portion 2002 (comprising a thin metallic wire, for example, having a cross-sectional area larger than conductor wires 110). In at least one embodiment, body 102 comprises a first portion 2000 comprising a combination of carbon fiber and epoxy, and a second portion 2002 comprising a stainless steel wire, whereby first portion 2000 completely or substantially surrounds second portion 2002. Such an embodiment would not then require the need for an additional coating 500, 600 when conductor wires 110 are placed adjacent to body 102, or within grooves defined within the second portion 2002 as shown in FIG. 20B.

Figure 20C:
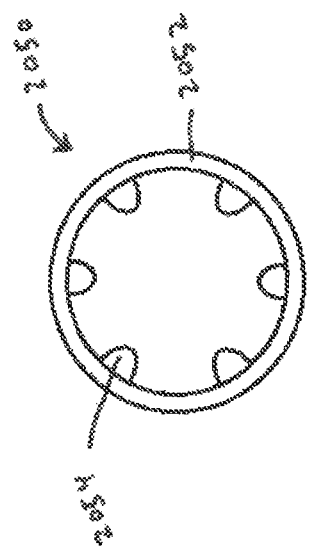
FIG. 20C shows a cross-sectional view of a die used to manufacture a device, according to an exemplary embodiment of the present disclosure.

Such an embodiment of a body 102 (having a first portion 2000 and a second portion 2002) may be easier to manufacture/extrude given its material properties. For example, and as shown in FIG. 20C, a die 2050 having an outer portion 2052 and one or more die tabs 2054 positioned therein could be used to define one or more grooves 104 within a body 102 of an exemplary device 100 of the present disclosure. A body 102 could be advanced (or pulled) through die 2050 to define one or more grooves 104 within body 102, and a relative twisting of body 102 and/or die 2050 during the process could cause the grooves 104 to have a spiral configuration (instead of a straight configuration of no twisting (or offsetting twisting)) were to occur.

Figure 20D:
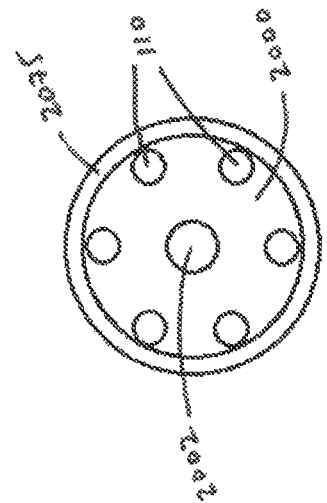
FIG. 20D shows a cross-sectional view of a device having a first portion surrounding a second portion and conductor wires positioned in the first portion, according to an exemplary embodiment of the present disclosure.

An exemplary device 100 of the present disclosure, using a non-metallic first portion 2000 as referenced above, may be manufactured as follows. An elongated shell 2075, as shown in cross-section in FIG. 20D, could house one or more conductor wires 110, and material for a first portion 2000 (such as a combination of carbon fiber and epoxy) could be introduced into elongated shell 2075. Curing and/or cooling of said material, for example, would result in a device having one or more wires 110 formed therein. An optional second portion 2002, such as a stainless steel wire, could also be positioned within elongated shell during the manufacturing process so that a device 100 with one or more wires 110 formed in a first portion 2000 and a second portion 2002 results therefrom.

Figure 20E:
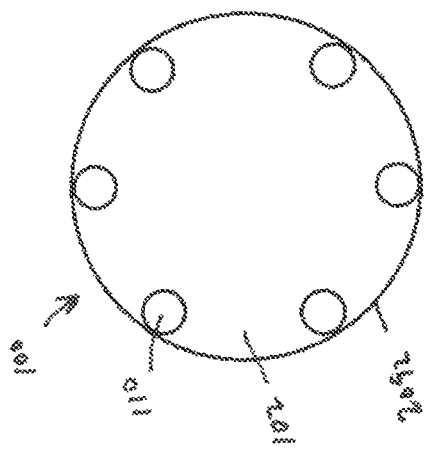
FIGS. 20E-20H show cross-sectional views of devices having conductor wires embedded therein, according to exemplary embodiments of the present disclosure.
Figure 20F:
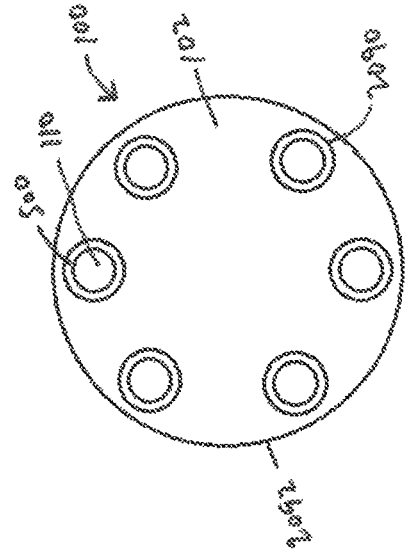

Regardless of method of formation, additional device 100 embodiments of the present disclosure are shown in FIGS. 20E-20F. As shown in FIG. 20E, for example, a plurality of conductor wires 110 may be positioned completely within core body 102 (as shown in cross-section), whereby core body 102 is itself insulative (non-conductive) so that conductor wires 110 do not require any coating 500, 600. FIG. 20F shows another exemplary device 100 embodiment, whereby an optional coating 500 (or 600) is positioned around conductor wires 110 and/or an optional coating 500, 600 is positioned within openings 2090 used to house conductor wires 110, or by another configuration as described herein. As shown therein, and in at least one embodiment, conductor wires 110 are separated from one another by at least part of core body 102, and are positioned around a relative perimeter of body 102. In the embodiments shown in FIG. 20E and FIG. 20F, conductor wires 110 are completely subsurface, in that a particular cross-section of device 100 does not have any conductor wires 110 exposed along a surface 2092 of device 100.

Figure 20G:
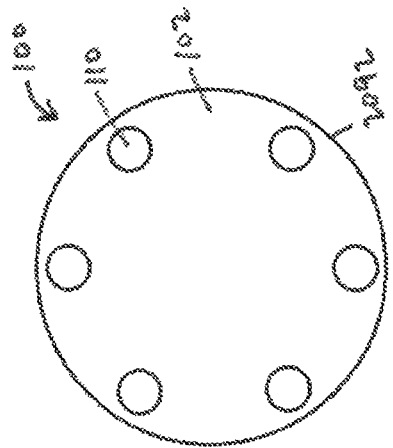
Figure 20I:
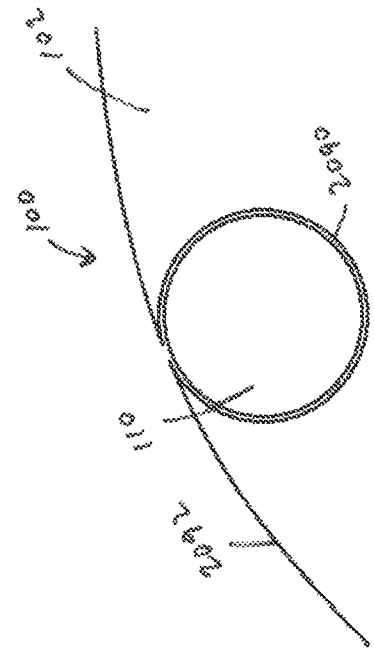
FIG. 20I shows a close-up view of a portion of a cross-section of a device with a conductor wire therein, according to an exemplary embodiment of the present disclosure.
Figure 20H:
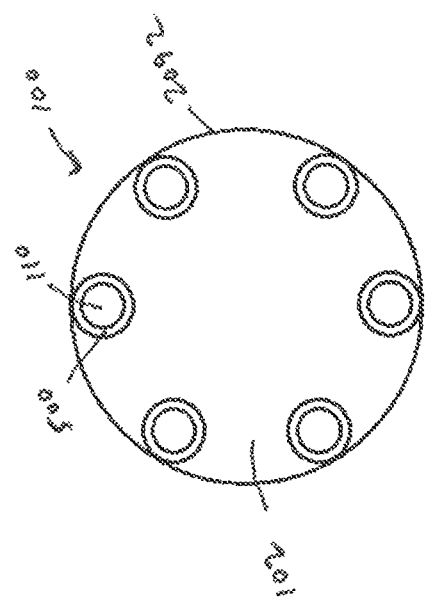

Additional embodiments of devices 100 of the present disclosure are shown in FIGS. 20G and 20H, whereby conductor wires 110, or a coating 500 (or 600) positioned around conductor wires 110, are either only slightly exposed along a surface 2092 of body 102, or not exposed, but just subsurface, so that the amount of body 102 between the surface 2092 of body 102 and a conductor wire 110 (or a coating 500, 600 around a conductor wire 110) is nominal so to provide potential relatively easy access to conductor wire 110 by way of puncture of the surface 2092 of body 102. FIG. 20I shows a close-up view of a portion of a device 100, whereby a conductor wire 110 is only slightly exposed along a surface 2092 of body 102. In at least one embodiment, approximately 10% or less of a circumference of the conductor wires 110 are exposed along a surface 2092 of the elongated body.

Various devices 100 of the present application have various inherent properties, such as, for example, flexural rigidity, pushability, and steerability (torque transfer). Use of such a device 100 within a patient's body would require the user to be able to push/pull the device, steer the device, and know that the device is sufficiently rigid (but not too rigid) to be used as desired.

Figure 21:
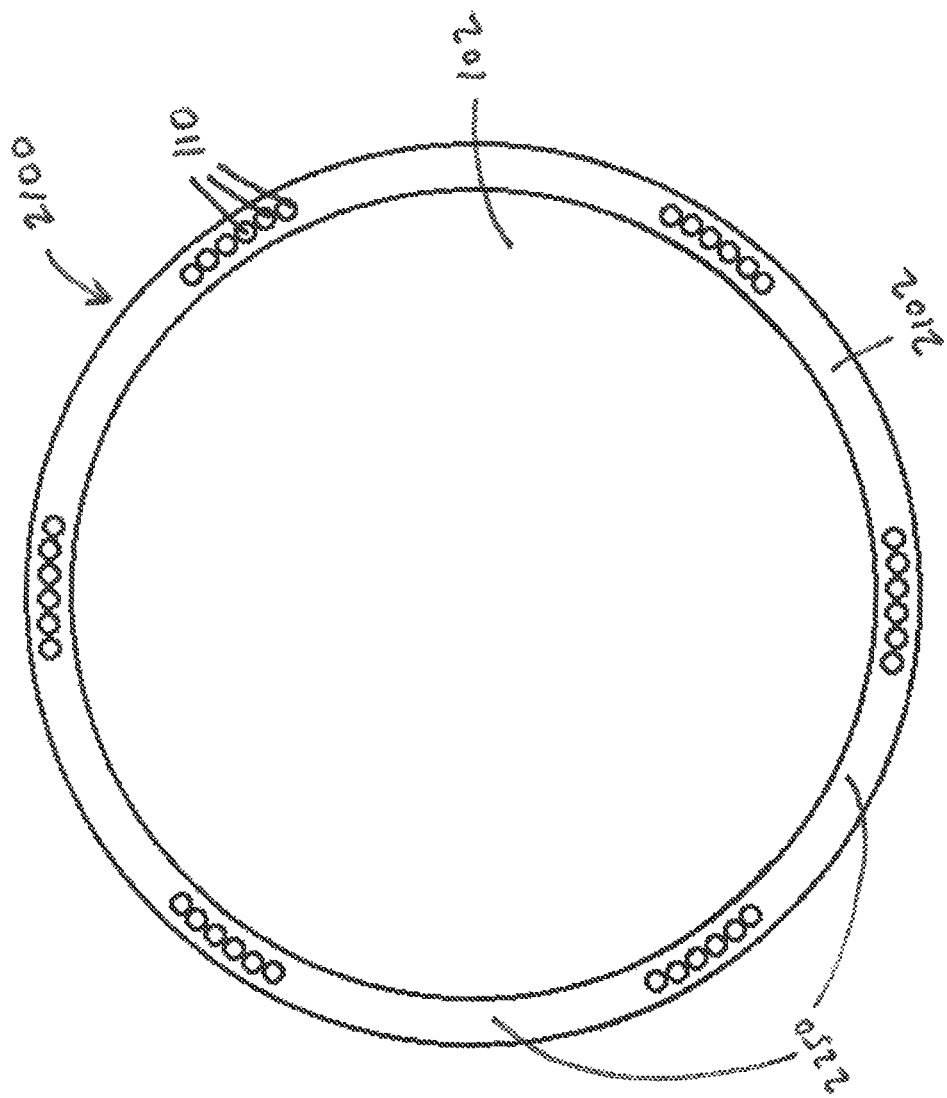
FIGS. 21 and 22 show wraps having conductive elements positioned therein, according to exemplary embodiments of the present disclosure.

An additional embodiment of a device 100 of the present disclosure is shown in FIG. 21. As shown in FIG. 21, a cross-sectional view of an elongated wrap 2100 is shown comprising one or more conductive elements may be used in connection with a core body 102, whereby wrapping the wrap 2100 around body 102 would produce a device 100 that is either fully or partially operable as a conductive device 100. For example, a wrap 2100 can have a plurality of conductive wires 110 (which can be, in this and in various other embodiments of the present disclosure, conductive traces that are deposited in or on a film, resulting in a printed circuit) embedded therein (within a flexible wrap body 2102) or thereon (upon a flexible wrap body 2202) around a relative perimeter of wrap body 2102, and when wrap 2100 is placed around a body 102, it can either be affixed (using an adhesive 602, 1675 of the present disclosure) thereto or heat-shrinked (or shrink-wrapped) around body 102. Wrap 2100, in at least one embodiment, may be completely circumferential or otherwise fit completely around a portion of a body 102, or it may be planar and wrapped around body 102. In a heat-shrinkable embodiment, the inner diameter of wrap 2100 may be somewhat larger than an outer diameter of body 102, and the heat-shrink properties of the wrap 2100 material itself would allow wrap 2100 to fit securely around body 102. In at least one embodiment, a wrap 2100 would have dimensions to eventually fit around an 0.0131" diameter body 102, whereby wrap 2100 has a thickness of approximately 0.0004" and conductor wires 110 therein have an outer diameter of approximately 0.0004" or less. In other embodiments, the conductor wires 110 can be as small as 0.0001" to 0.0003" in diameter, or larger as desired. In at least one embodiment, wrap 2100 itself (without any wires, electrodes, traces, sensors, connectors, etc., attached thereto or embedded therein) is approximately 10 microns (0.0004") thick, and the conductor wires 110 (traces, for example) deposited thereon would locally increase the thickness of wrap 2100 to approximately 20 microns (0.0008"). In at least one embodiment, wrap 2100 comprises a polyimide.

In various embodiments, wrap 2100 can comprise one or more conductor wires 110, an exemplary assembly 1800 of conductor wires 110, electrodes, traces, sensors, connectors, and the like attached thereto or embedded therein, including, but not limited to, an impedance portion 800, a temperature portion 810, and a connection portion 830. The conductor wires 110 (or conductive traces, as referenced above) can be in a straight configuration, a helical configuration, or any other configuration whereby at least one conductive wire 110 or trace extends the desired length of wrap 2100. A complete wrap 2100 (including, for example, conductor wires 110) would be flexible, so that the wrap 2100 substrate itself is flexible and the conductor wires 110 are also flexible. An exemplary wrap 2100, an exemplary impedance substrate 1600, and/or an exemplary connector substrate 1675 of the present disclosure can be positioned about a body 102 of the present disclosure or other wires or catheters with or without grooves 104 defined therein, to form at least a portion of an operable device 100 of the present disclosure.

If the conductor wires 110 are adjacent to one another and not shielded from one another (as shown in an individual combination of six conductor wires in FIG. 21), there would be enough adjacent wires to transmit the desired signal without excessive resistance. As resistance is directly related to the diameter of the conductor wire 110 itself, additional conductor wires 110 could be added as needed. For example, if a desired resistance is achieved using a combination of six conductor wires 110 of a particular diameter, and conductor wires having approximately ⅙ the diameter are desired, then resistance is increased by 36 (six squared), and as such, 36 conductor wires 110 would be needed to transmit an individual signal. In an embodiment where six signals are transmitted using device 100 simultaneously, a total of 216 (36×6) conductor wires 110 would be needed in total to maintain the same level of resistance. In such an embodiment, the 216 conductor wires 110 could be placed circumferentially about wrap 2100, with insulative spaces between each group of 36 conductor wires 110, if desired. In addition, and in various embodiments, conductive wires 110 of the present disclosure may have any number of cross-section configurations, such as round, square, or rectangular as described below.

Figure 22:
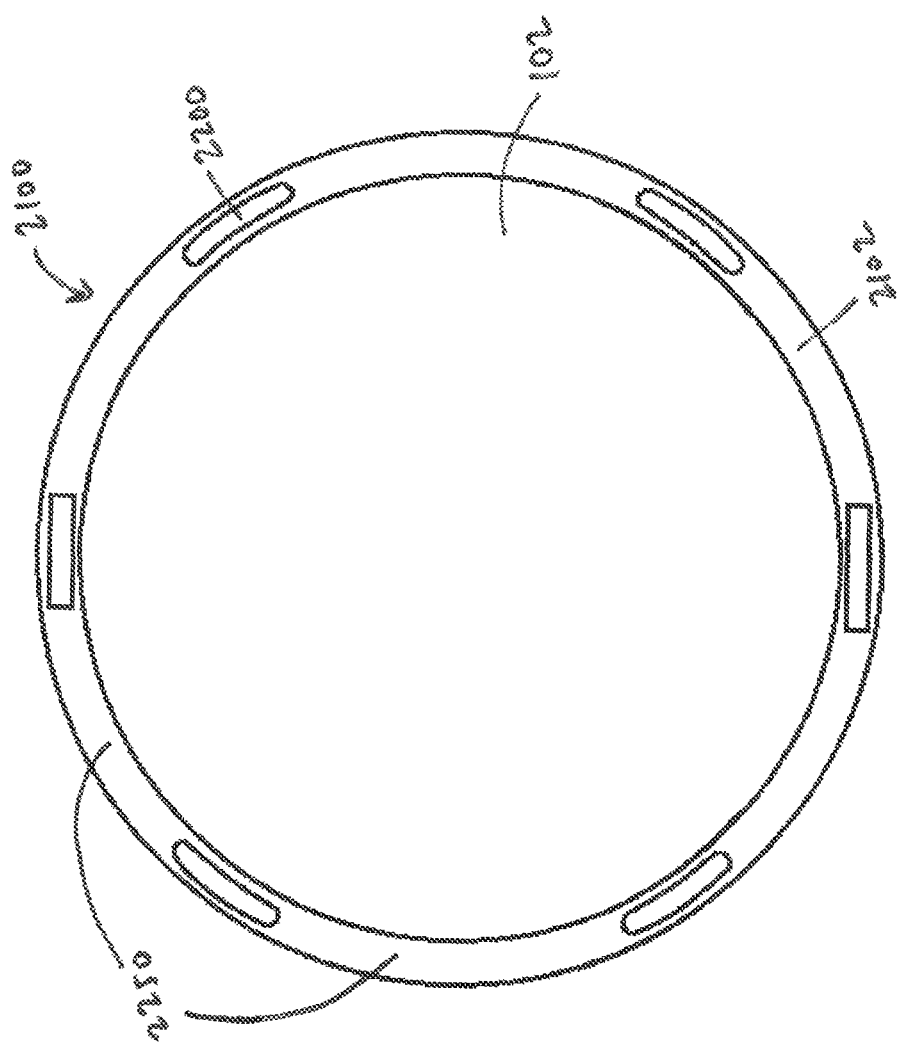

An additional exemplary wrap 2100 embodiment is shown in FIG. 22. As shown therein, a cross-sectional view of an elongated wrap 2100 is shown comprising one or more conductive elements within or upon wrap body 2102 may be used in connection with a core body 102, whereby wrapping the wrap 2100 around body 102 would produce a device 100 that is either fully or partially operable as a conductive device 100. For example, and as shown in FIG. 22, a wrap 2100 can have a plurality of wide conductors 2200 embedded therein or thereon, and when wrap 2100 is placed around a body 102, it can either be affixed (using an adhesive 602, 1675 of the present disclosure) thereto or heat-shrinked (or shrink-wrapped) around body 102. Wide conductors, as shown in FIG. 22, can have a rectangular cross-section, or can have a quasi-rectangular cross-section, whereby the relative smaller sides and/or the relative larger sides have a curvature. Examples of such wide conductors 2200 are shown in FIG. 22, noting that in any given embodiment, a device 2200 may have one or more configurations of wide conductors 2200 therein or thereon.

In addition, and as shown in FIG. 22, an exemplary elongated wrap may have one or more shrink zones 2250 present therein, whereby shrink zones 2250 are present in between portions of wrap 2100 that do not have conductor wires 110 or traces. Shrink zones 2250, applicable to various wrap embodiments, would allow said portions of wrap 2100 to shrink about a core body 102, for example, while portions of wrap 2100 having conductor wires 110, for example, may not be as susceptible to heat shrinking, for example.

An additional device embodiment 100 of the present disclosure is shown in FIG. 23. As shown in FIG. 23, device 100 comprises a body 102 having a wavy configuration, whereby one or more conductor wires 110 (or traces) may be positioned within grooves 104 defined within body 102. The wavy configuration, which may be within one plane, for example, would allow a user of said device 100 to steer the device 100 within a luminal organ of interest and allow for flexing of device 100 as desired. The wavy configuration may be positioned in one or more places about body 102.

Figure 24A:
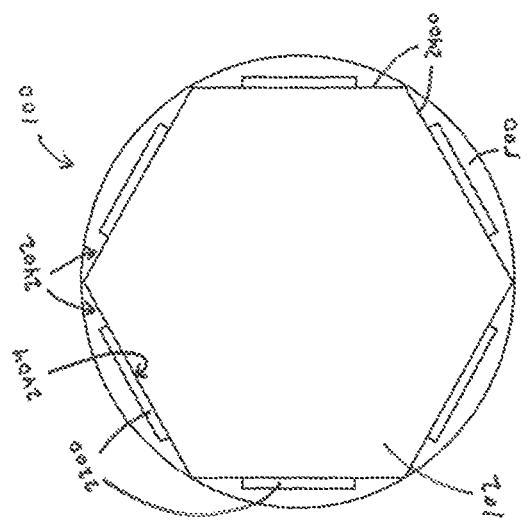
FIGS. 24A and 24B show cross-sectional views of devices having core bodies with flat sides and wide conductors placed thereon, according to exemplary embodiments of the present disclosure.
Figure 24B:
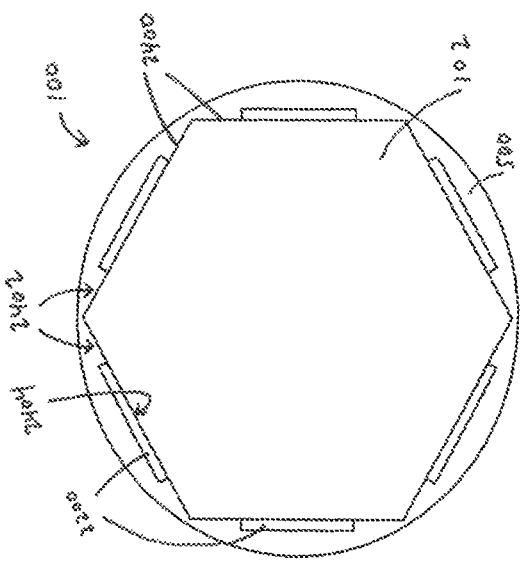

Additional embodiments of exemplary devices 100 of the present disclosure are shown in FIGS. 24A and 24B. As shown in FIGS. 24A and 24B, by way of cross-section of a portion of said devices 100, devices 100 comprise a body 102 having at least one planar side 2400 configured so that one or more wide conductors 2200 (and/or conductor wires 110, if desired) may be positioned thereon. Contrary to the device 100 embodiments shown in FIGS. 1B and 1D, for example, planar sides 2400 do not have, create, or form a pocket to receive one or more wide conductors 2200, while the grooves 104 shown in FIGS. 1B and 1D do form a pocket to receive one or more conductor wires 110. Wide conductors 2200 (which could also be shown as being deposited conductive traces as referenced herein), would be positioned on one or more planar sides 2400 upon core body 102, so that a signal may be transmitted therethrough (from an electrode to a connector, for example).

Planar sides 2400, as shown in FIGS. 24A and 24B, define a planar surface 2402, and wide conductors 2200 define a wide conductor surface 2404, so that wide conductor 2200 could be placed directly upon planar side 2400, and so that planar surface 2402 and wide conductor surface 2404 would contact one another. Such an embodiment would differ from an embodiment using a round conductor wire 110, as such a conductor wire 110 would not have a flat surface to contact planar surface 2402 of device 100. This would allow a wide conductor 2200 to be placed directly upon a planar side 2400, and make placement of the same easier during manufacturing as wide conductor 2200 would not be prone to rolling off of planar side 2400 like a round conductor wire 110 would. In addition, and as referenced above, a trace (which would be placed on a planar side 2400 like a wide conductor 2200 shown in FIGS. 24A and B) could be placed directly on one or more planar sides 2400 during manufacturing, which would be a relatively easier process than attempting to place such a trace about a curved surface.

In an embodiment where it is preferred to coat core body 102 with a coating 500, 600, a coating 500, 600 would be positioned about core body 102, and a conductor wire 110 would be positioned upon coating 500, 600 at one or more planar sides 2400. Any number of planar sides 2400 could be defined about core body 102, including one, two, three, or more, including the six planar sides 2400 shown in FIGS. 24A and 24B. In an embodiment having six planar sides 2400 and no other sides, core body 102 would have a hexagonal cross-section. In various embodiments, and as shown in FIGS. 24A and 24B, an additional coating 500 (or 600) may be positioned around some or all of core body 102 with conductor wires 110 (or traces) positioned on one or more planar sides, so to smooth the outer dimension of said device 100. Coating 500 (or 600) may be present at a relative corner 2450 of core body 102 with some thickness (as shown in FIG. 24A) or little to no thickness (as shown in FIG. 24B).

Figure 25C:
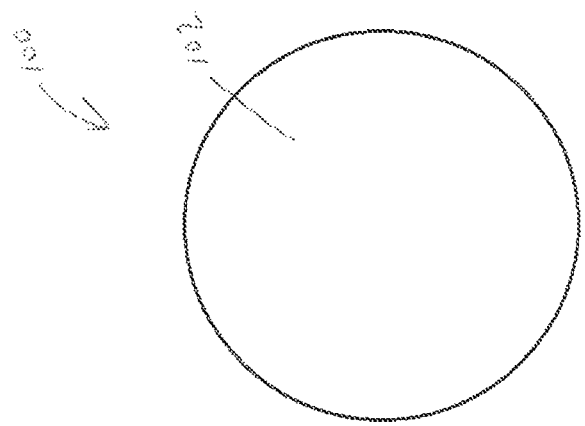
FIGS. 25A, 25B, and 25C show cross-sectional configurations of various core bodies, according to exemplary embodiments of the present disclosure.
Figure 25B:
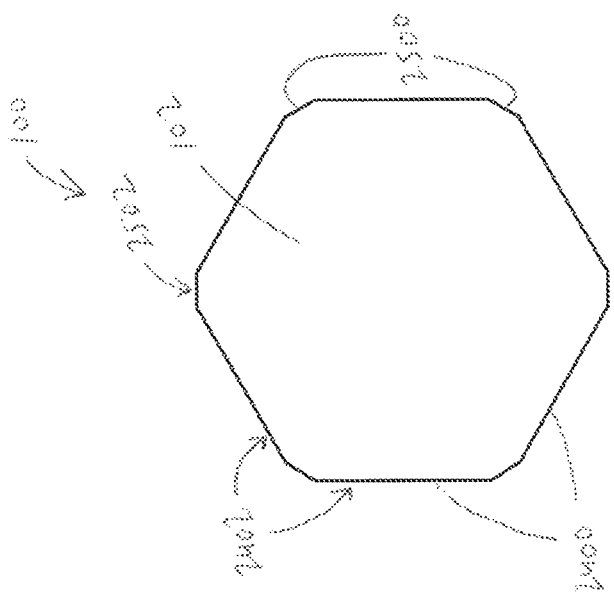
Figure 25A:
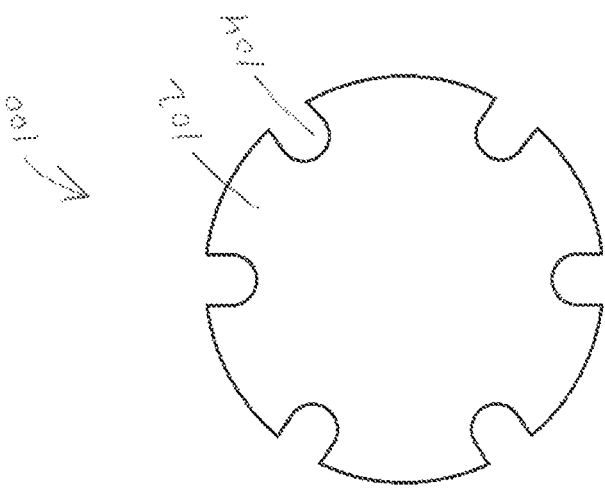

As referenced above, and as shown in cross-section in FIGS. 25A-25C, a number of potential exemplary core body 102 configurations may be useful in connection with one or more device 100 embodiments of the present disclosure. An exemplary multi-hole core 102, shown in cross-section in FIG. 25A and previously shown in cross-section in at least FIGS. 1C, 1D, 2A, and 20B, may require a number of processing steps to potentially grind, etch, and/or extrude, for example, core body 102 to create the multi-hole core body 102 having one or more grooves 104 defined thereon. In addition, and in attempt to mimic or substantially meet one or more properties of a traditional 0.014" diameter wire having a round core, such a multi-hole core could be at or between, for example, 0.013" to 0.0138" in maximum diameter, or even as high as 0.014" in maximum diameter, not including any sort of coating 500, 600 or other componentry positioned thereon.

An exemplary hexagonal core body 102 configuration, shown in cross-section in FIG. 25B and previously shown in cross-section in FIGS. 24A and 24B, may also require one or more processing and/or shaping steps so that the resulting core body 102 resembles a hexagonal core. In attempt to mimic or substantially meet one or more properties of a traditional 0.014" diameter wire having a round core, such a hexagonal core could be at or between, for example, 0.0127" to 0.0138" in maximum diameter, or even as high as 0.014" in maximum diameter, not including any sort of coating 500, 600 or other componentry positioned thereon. As shown in FIG. 25B, for example, such an embodiment has six planar sides 2400, each defining a planar surface 2402, as previously shown in FIGS. 24A and 24B. However, and as shown in FIG. 25B, an exemplary device 100 embodiment with a hexagonal core body 102 may further have one or more reduced corners 2500, whereby the one or more reduced corners 2500 define one or more planar edges 2502 in between the one or more planar sides 2400. In such an embodiment, the overall core body 102 diameter can remain at a desired size, but the amount of core body 102 (in cross-sectional area, for example) for that same diameter would be greater as compared to a hexagonal core body 102 without any reduced corners 2500. For any given diameter, for example, the larger/longer the planar edges 2502, the greater the cross-sectional area of core body 102, up until the size/length of planar edges 2502 is equal to the size/length of planar sides 2400, forming an effective twelve-sided core body 102 having sides of equal size.

A solid round core body 102, such as shown in FIG. 25C, may require the least amount of processing (given its native round shape), and in various embodiments, the core body 102 would have a diameter at or between 0.013" up to 0.014".

Table 1 below shows data in connection with various core body 102 configurations and sizes. As listed therein, various core bodies (in the "Description" column) of various maximum diameters (in inches in the "Diameter" column) were tested, with the flexural rigidities (EI of the dimension N·mm$^2$ (a combination of E, which is the effective Young's Modulus of the composite material and I is the second moment of inertia as previously referenced above) and the amount of degradation as compared to a 0.013" standard round core.

TABLE 1

| Description | Diameter (in) | Flexural Rigidity | Degradation |
| --- | --- | --- | --- |
| Round | 0.013 | 116.71 | Standard |
| Hexagon | 0.0127 | 73.26 | −37.23% |
| 0.12" pitch helical single-groove | 0.013 | 73.34 | −37.16% |
| 0.12" pitch helical single-groove | 0.0134 | 75.6 | −35.23% |
| Hexagon | 0.013 | 80.43 | −31.08% |
| Hexagon | 0.0131 | 82.94 | −28.94% |
| Round | 0.012 | 84.73 | −27.40% |
| 0.12" pitch helical multi-hole | 0.013 | 88.87 | −23.85% |
| 0.12" pitch helical multi-hole | 0.0134 | 91.6 | −21.51% |
| Hexagon | 0.0136 | 96.37 | −17.45% |
| Round | 0.0125 | 99.76 | −14.52% |
| Hexagon | 0.0138 | 102.13 | −12.49% |

As shown in Table 1, the tested device 100 embodiment with the highest flexural rigidity, and thus the lowest amount of degradation as compared to the standard 0.013" diameter round core, had the 0.0138" diameter hexagonal core body 102. One exemplary goal, with the various core body 102 configurations, is to balance degradation with the various construction options so to arrive at electrical performance with acceptable mechanical performance and behavior.

With respect to the various types of conductor wires 110 (or traces 110), certain configurations may be preferred over others. For the purposes of this disclosure, and to clarify prior references herein to conductor wires 110 or traces, element "110" shall generally apply to both conductor wires and traces. As such, references herein to conductor wires 110 may also refer to traces, and the term traces 110 may also be used, which may refer to wire embodiments as well.

In various embodiments, and if round or flat conductor wires 110 are used, a 5:1 ratio of width:height would may be preferred, and conductor wires 110 may comprise copper. In many embodiments, flat conductor wires 110 cannot be independently insulated. If a trace 110 (such as a conductive polymer or plating material) is used, a resistivity of 0.0001 Ω-cm would be needed, and such trace 110 material may be used to completely or partially fill a groove 104, for example, or be placed around a wire.

Figure 26B:
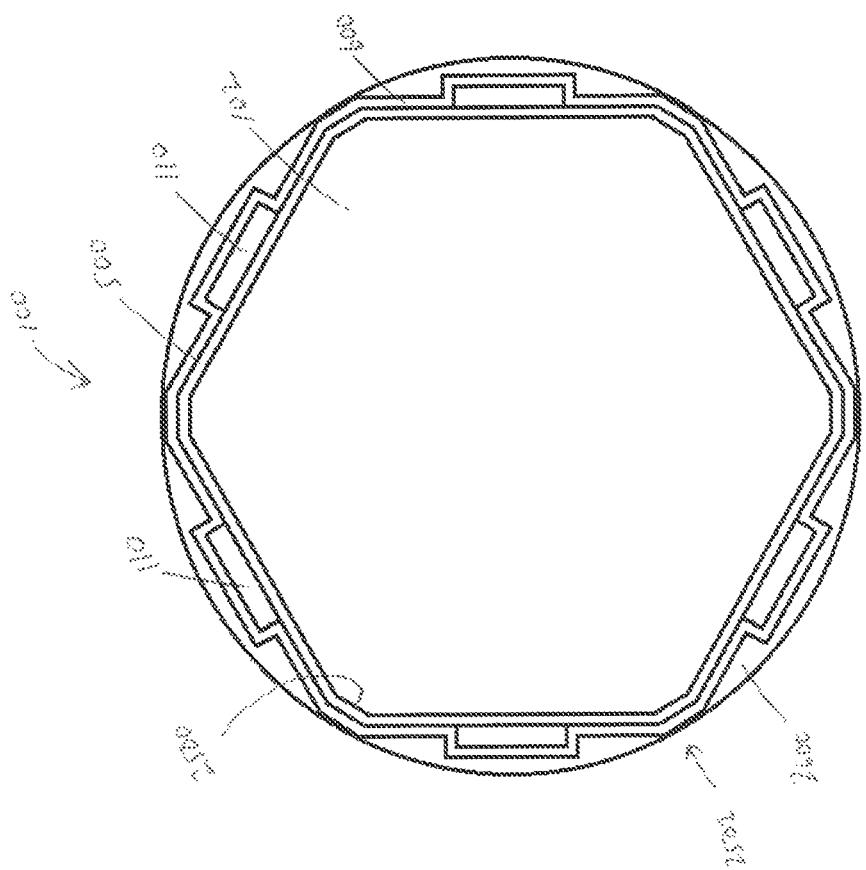
Figure 26A:
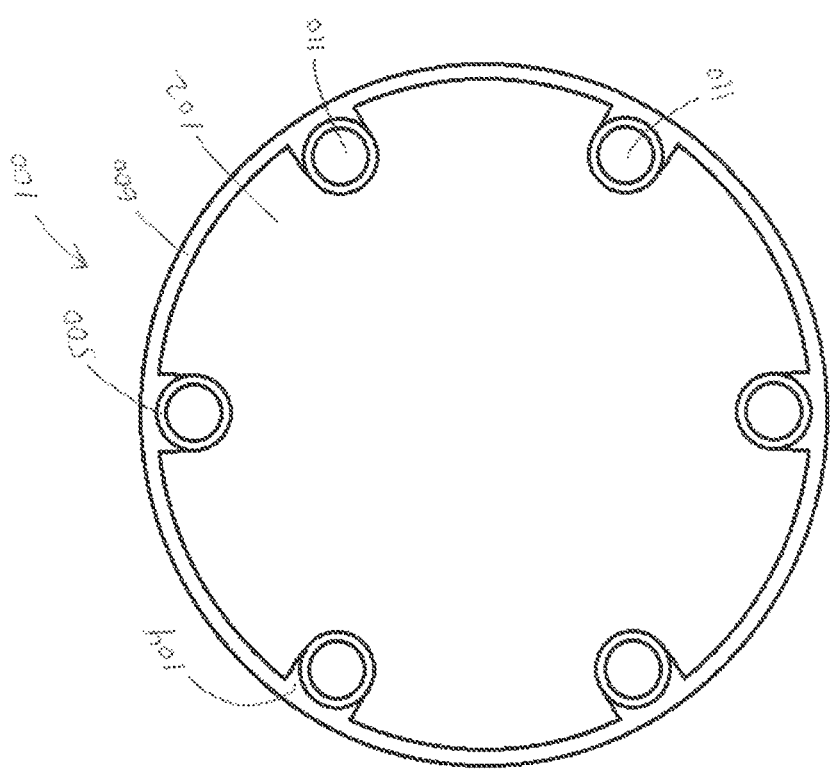

Another exemplary device 100 embodiment of the present disclosure is shown in cross-section in FIG. 26A. As shown therein, device 100 comprises a multi-hole (or multi-slot) core body 102 configuration, shown by way of example with six grooves 104. Such an embodiment, for example, may have a core diameter at or between 0.013" to 0.0136", so to not exceed 0.014" with coating 600 (or coating 500) positioned around core body 102. Core body 102, with coating 600 (or coating 500) positioned thereon, and in at least one embodiment, would have an overall diameter of or approximately 0.0139". Coating 500, 600, in at least one embodiment, may comprise polytetrafluoroethylene (PTFE). In such an embodiment, core body 102 is itself conductive (stainless steel, for example), and so that conductor wires 110 do not come into conductive contact with core body 102, each conductor wire 110 would have a coating 500 (or coating 600) positioned thereon as shown in FIG. 26A. In at least one embodiment, conductor wires 110 would have a diameter at or between 0.0015" to 0.003", and may comprise, for example, stainless steel (1.15 k$\Omega$/190 cm) or copper (28$\Omega$/190 cm). Such an exemplary embodiment is anticipated to have an overall degradation (as described in connection with Table 1 above) of between approximately 20-23%.

An additional device 100 embodiment of the present disclosure is shown in cross-section in FIG. 26B. As shown in FIG. 26B, device 100 comprises a hexagonal configuration core body 102 surrounded by a first coating 500 (or coating 600). An optional adhesive agent 602 (not shown in FIG. 26B) may be used to secure conductor wires 110 to the coating 500 surrounding core body 102. In at least one embodiment, conductor wires 110 are positioned upon the coating 500 surrounding core body 102 without adhesive agent 602. A second coating (shown as coating 600 in FIG. 26B) may be applied around device 100 so that coating 600 encases conductor wires 110. So to form an overall outer round shape, a third coating (shown as coating 2600 in the figure, which may also be coating 500 or coating 600) is used to surround coating 600. In such an embodiment, for example, core body 102 may itself have a diameter of or approximately 0.0127" at its largest dimension, and conductor wires 110 may comprise wires having a width of or approximately 0.002" and a height of or approximately 0.0004". Such a conductor wire 110 dimension, if comprising copper (62$\Omega$/190 cm at that size), would be able to transmit signals therethrough as needed. With all coatings applied (coatings 500, 600, 2600), an exemplary device 100 of the present disclosure may have an overall outer diameter of or approximately 0.0139".

Figure 27B:
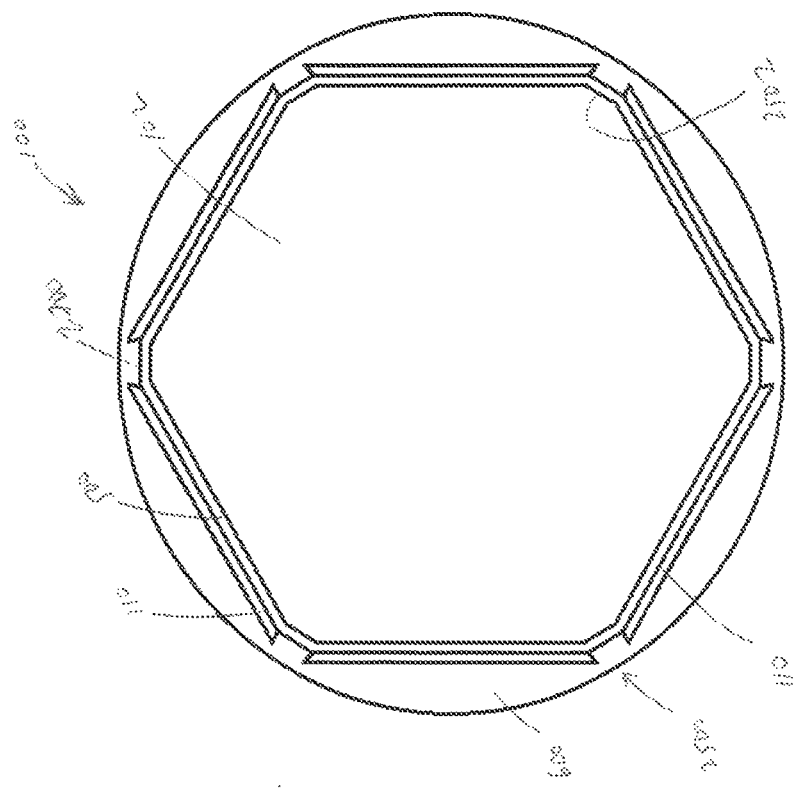
Figure 27A:
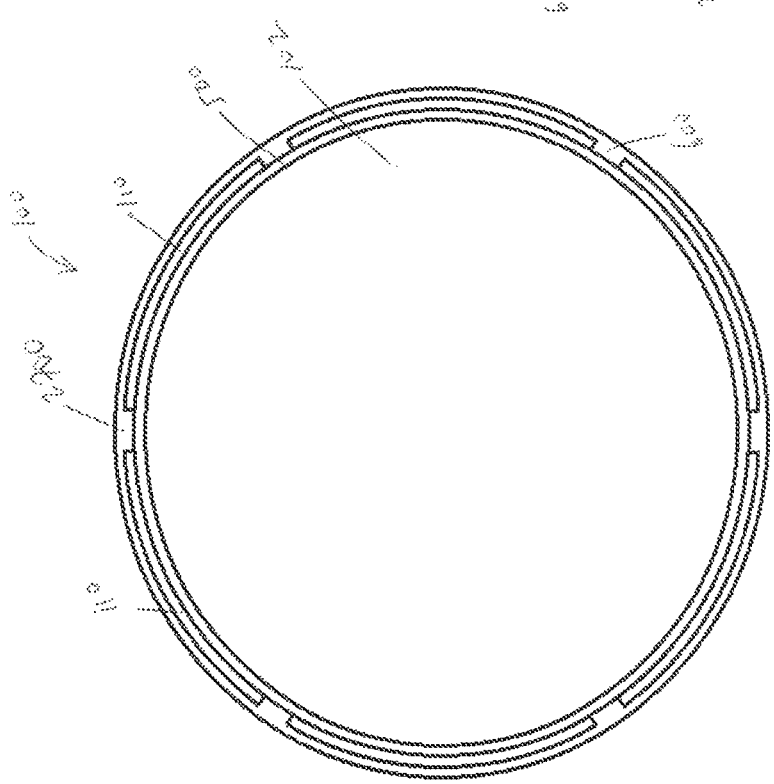
Figures 28A, 28B:
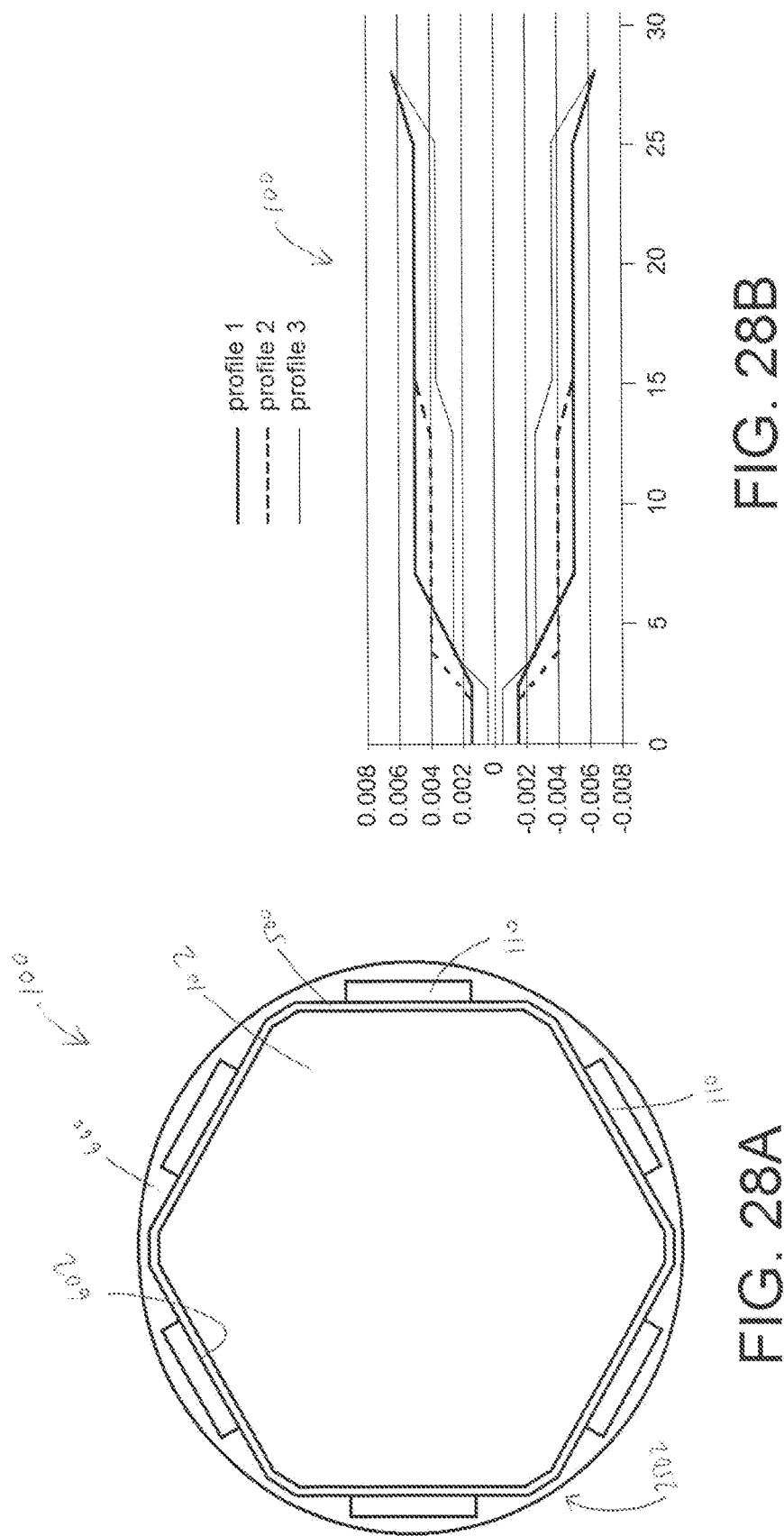

Additional device embodiments using conductive traces 110 (or conductive adhesives, for example), are shown in FIGS. 27A, 27B, and 28A. As shown in the exemplary device 100 embodiment of FIG. 27A, device 100 comprises a core body 102 with a round cross-section, and in at least one embodiment, the round core body 102 has a diameter of or approximately 0.013". Other diameters, such as diameters larger than 0.013" and approaching 0.014", may be used in other embodiments. As referenced above, a 0.013" round stainless steel core is the standard used to determine flexural rigidity and degradation, so such a core, as compared to other cores, has zero degradation. As shown in FIG. 27A, device 100 comprises a first coating 500 around core body 102, which may be a polyimide coating 500 or another coating 500 suitable to prohibit a signal from transferring from core body 102 to or from conductor wires 110 or traces 110. Traces 110, which may be, for example, gold or copper traces having dimensions of or approximately 0.0002"×0.006" (60$\Omega$/190 cm at that size), would be positioned on top of coating 500. In at least one embodiment, one trace 110 is initially used that spans most or all of an entire device 100 circumference at a given location along a length of device 100, and one or more gaps 2700 may be formed within trace 110 using a laser and/or a physical device to score/cut trace 110 at one or more locations. Gaps 2700, in various embodiments, may be relatively small (0.001"-0.002", for example), so that a larger amount of trace 110 can be used. Therefore, and as shown in FIG. 27A, for example, six traces 110 could be applied to coating 500, with six gaps 2700 defined therebetween, or fewer traces 110 could be applied with one or more gaps 2700 formed therein after initial trace 110 placement. After trace 110 placement, a second coating 600 may be applied around device 100, so that traces 110 are insulated from the outside of device 100. Such a device 100 embodiment may then have an overall diameter at or below 0.014", if 0.014" is a maximum diameter allowed/desired for a particular application.

The device 100 embodiments shown in FIGS. 26A, 26B, 27A, and others referenced herein, are shown in cross-section, with all conductor wires 110 (or traces 110) surrounded by some sort of coating so that wires/traces 110 are not exposed on a relative outside of the devices 100. However, when forming portions of devices 100 (such as impedance portions 800 and/or connection portions 830), the various electrodes and/or connectors would be electrically coupled/connected to wires/traces 110 at or near the locations where electrodes and/or connectors are exposed on the outside of devices 100. Such configurations allow wires/traces 110 to be properly shielded and also allow for proper connection of the various electrodes/connectors.

An additional device 100 embodiment of the present disclosure is shown in FIG. 27B, wherein core body 102 has a hexagonal configuration. Such an embodiment, for example, may also have a coating 500 surrounding core body 102, and one or more traces 110 positioned upon coating 500. A stainless-steel hexagonal core having a largest diameter of 0.0127" (or another size) may be used, and if such a size is used, the initial core body 102 degradation is approximately 37% as compared to a 0.013" round core body. If six traces 110 are used, for example, a gap 2700 would be defined between each trace 110. If less than six traces 110 are used, one or more gaps 2700 may then be laser or mechanically cut into trace(s) 110 to form the desired number of traces 110, which may be any number of total traces 110 (1, 2, 3, or more). In at least one embodiment, gaps may be at or approximately 0.001", and gold or copper traces 110 of or approximately 0.0001"×0.006" (120$\Omega$/190 cm at that size) may surround core body 102. A second coating 600 may then be used to surround all traces 110, forming the external dimensions of device 100 as with second coating 600 in FIG. 27A, for example.

Yet another exemplary device 100 embodiment of the present disclosure is shown in FIG. 28A. As shown therein, device 100 has a hexagonal core body 102 (such as a 0.0127" stainless steel core), surrounded by a first coating 500. First coating 500, if used, may comprise polyimide, polytetrafluoroethylene (PTFE), or another suitable material. If an adhesive agent 602 is used to facilitate application of conductive wires 110 or traces 110 therein, such an agent may comprise a flexible silver adhesive 602 and may be applied at a dimension at or about 0.0005"×0.0036" (1.61$\Omega$/190 cm at that dimension) at or near wires/traces 110. A second coating 600 would then be applied around wires/traces 110 to form the overall cross-sectional dimension of device 100, which would be larger than the initial core body 102 up to 0.014" should 0.014" be a maximum diameter. As such, the device 100 embodiments shown in FIGS. 26B, 27B, and 28A each have hexagonal core bodies 102 but an overall round device 100 shape in cross-section.

In addition to the foregoing, and as referenced herein in connection with at least FIG. 17B, a relative distal end of an exemplary device embodiment 100 of the present disclosure may have any number of configurations. As shown in FIG. 28B, three separate distal end profiles are shown, with profile 1 being a known profile in the art, and profiles 2 and 3 being exemplary profiles 2800 of the present disclosure. Profile 2, as shown in FIG. 28B, has the same initial overall distal end size as profile 1 (the first portion), but tapers to a smaller second portion than profile 1, and then to the same final portion as profile 1. Such an embodiment may relate to a device 100 of the present disclosure having a nitinol tip. Profile 3, also as shown in FIG. 28B, has the smallest overall distal end (first portion), and tapers to a second portion and then to a third portion, with each portion being the smallest of the three profiles. Profile 3, for example, may relate to a device 100 embodiment having a stainless steel tip.

FIGS. 29A and 29C show exemplary distal portions 2900 of devices 100 of the present disclosure. As shown therein, distal portions 2900 include an impedance portion 800 having electrodes 802, 804, 806, 808, and thermistor wire ends 812, 814 positioned relative to impedance portion 800. Various conductor wires/traces 110 connect to impedance portion 800 and thermistor wire ends 812, 814, whereby, for example, conductive path connections may be made from the backside of electrodes 802, 804, 806, 808 (which may be electrode bands) to conductive wires/traces 110. A compliant portion 820 (distal coil) with an atraumatic tip 822, as shown in the exemplary embodiments in FIGS. 29A and 29C, is at the very distal end of device 100. Such a distal portion 2900 may have such componentry as part of device 100 and not part of an impedance substrate 1600, or may have some componentry (such as some conductive wires/traces 110), while impedance substrate 1600 has the remaining components, including additional conductive wires/traces, as shown in FIGS. 29B and 29C. Impedance substrate 1600, shown in FIGS. 29B and 29C, comprises a flexible substrate 1602 (such as polyimide, including but not limited to Kapton) having electrodes 802, 804, 806, 808, and thermistor wire ends 812, 814 thereon/therein, with multiple conductor wires/traces 110 coupled to the same. Impedance substrate 1600 can then be placed on device 100, as shown in FIG. 29C, so that conductor wires/traces 110 of device 100 can electrically couple to conductor wires/traces 110 of impedance substrate 1600. Impedance substrate 1600 may be wrapped around device 100 in a number of configurations, including spiral-wrapped. With such an impedance substrate 1600, the conductive path connections may be formed from the backside of the impedance substrate 1600 or at flanges, for example, on the relative proximal end of impedance substrate 1600. With such an impedance substrate 1600, electrode spacing tolerance should be repeatedly achievable. Various adhesives (such as adhesives 1650 or 602) can be used to couple the impedance substrate 1600 to device 100, if desired.

Similar distal portions 2900 to those shown in FIGS. 29A and 29C are previously referenced herein in FIGS. 16C and 16D. Connector substrates 1675, such as those shown in FIGS. 16E-16I, can be positioned around a relative proximal device 100 portion, whereby, in addition to the various embodiments previously referenced herein, various gold traces 110 can be laser patterned thereon, with epoxy injection molding used to position the various conductors.

While various embodiments of devices and systems for obtaining conductance data and methods of manufacturing and using the same have been described in considerable detail herein, the embodiments are merely offered as non-limiting examples of the disclosure described herein. It will therefore be understood that various changes and modifications may be made, and equivalents may be substituted for elements thereof, without departing from the scope of the present disclosure. The present disclosure is not intended to be exhaustive or limiting with respect to the content thereof.

Further, in describing representative embodiments, the present disclosure may have presented a method and/or a process as a particular sequence of steps. However, to the extent that the method or process does not rely on the particular order of steps set forth therein, the method or process should not be limited to the particular sequence of steps described, as other sequences of steps may be possible. Therefore, the particular order of the steps disclosed herein should not be construed as limitations of the present disclosure. In addition, disclosure directed to a method and/or process should not be limited to the performance of their steps in the order written. Such sequences may be varied and still remain within the scope of the present disclosure.

The invention claimed is:

1. A device, comprising:
   an elongated core body having a length, a perimeter, a cross-sectional configuration, and only one groove defined therein; and
   a plurality of conductive elements positioned around the perimeter of the core body and extending a majority of the length of the core body, the plurality of conductive elements surrounded by a first substantially or completely non-conductive coating;
   wherein the only one groove is configured to receive at least one conductive element of the plurality of conductive elements therein; and
   wherein the device, having the first substantially or completely non-conductive coating, has an overall round cross-section and an overall diameter between approximately 0.013" and approximately 0.050".

2. The device of claim 1, wherein the plurality of conductive elements are selected from the group consisting of a plurality of conductive wires and a plurality of conductive traces.

3. The device of claim 1, wherein the cross-sectional configuration is selected from the group consisting of a round cross-sectional configuration and a hexagonal cross-sectional configuration defining six planar sides.

4. The device of claim 1, wherein the cross-sectional configuration comprises a hexagonal cross-sectional configuration defining six planar sides and further defining one or more reduced corners.

5. The device of claim 4, wherein the elongated core body is at least partially surrounded by the first substantially or completely non-conductive coating, and wherein the plurality of conductive elements are positioned on the first substantially or completely non-conductive coating.

6. The device of claim 5, wherein the plurality of conductive elements comprise a plurality of conductor wires having a rectangular cross-section.

7. The device of claim 5, wherein the device is further surrounded by a second substantially or completely non-conductive coating, the second substantially or completely non-conductive coating defining the overall round cross-section.

8. The device of claim 1, wherein the elongated core body is at least partially surrounded by the first substantially or completely non-conductive coating, and wherein the plurality of conductive elements are positioned on the first substantially or completely non-conductive coating.

9. The device of claim 8, wherein the plurality of conductive elements are selected from the group consisting of a plurality of conductive wires and a plurality of conductive traces.

10. The device of claim 1, further comprising:
a detector coupled to the device at or near a distal end of the device, the detector configured to obtain conductance data when the device is operated in a fluid environment.

11. The device of claim 10, wherein the detector is coupled to one or more of the plurality of conductive elements, so that a signal may be transmitted along the one or more of the plurality of conductive elements to and/or from the detector, and wherein the detector comprises two detection electrodes positioned in between two excitation electrodes, wherein the excitation electrodes are operable to generate an electric field within a luminal organ that can be detected by the detection electrodes to obtain conductance data indicative of the luminal organ.

12. The device of claim 11, further comprising:
two thermistor wire ends operable to detect a temperature of a fluid within the luminal organ.

13. A device, comprising:
an elongated core body having a length, a perimeter, a cross-sectional configuration, and a first groove defined therein; and
a plurality of conductive elements positioned around the perimeter of the core body and extending a majority of the length of the core body, the plurality of conductive elements surrounded by a first substantially or completely non-conductive coating;
wherein the first groove is configured to receive at least one conductive element of the plurality of conductive elements therein;
wherein the device, having the first substantially or completely non-conductive coating, has an overall round cross-section and an overall diameter between approximately 0.013" and approximately 0.050";
wherein the elongated core body is at least partially surrounded by the first substantially or completely non-conductive coating, and wherein the plurality of conductive elements are positioned on the first substantially or completely non-conductive coating; and
wherein the plurality of conductive elements comprises a plurality of conductive traces produced by initially placing one or more conductive traces upon the elongated core body at least partially surrounded by the first substantially or completely non-conductive coating and removing portions of the one or more conductive traces to result in the plurality of conductive traces.

14. A device, comprising:
an elongated core body having a length, a perimeter, a cross-sectional configuration selected from the group consisting of a round configuration and a hexagonal configuration, and only one groove defined therein;
a plurality of conductive elements positioned around the perimeter of the core body and extending a majority of the length of the core body, the plurality of conductive elements surrounded by a first substantially or completely non-conductive coating; and
a detector coupled to the device at or near a distal end of the device and operably connected to one or more of the plurality of conductive elements, the detector configured to obtain conductance data when the device is operated in a fluid environment and to transmit the conductance data along one or more of the plurality of conductive elements;
wherein the only one groove is configured to receive at least one conductive element of the plurality of conductive elements therein; and
wherein the device, having the first substantially or completely non-conductive coating, has an overall round cross-section and an overall diameter between approximately 0.013" and approximately 0.050".

15. The device of claim 14, wherein the detector comprises two detection electrodes positioned in between two excitation electrodes, wherein the excitation electrodes are operable to generate an electric field within a luminal organ that can be detected by the detection electrodes to obtain conductance data indicative of the luminal organ.

16. The device of claim 14, further comprising:
two thermistor wire ends operable to detect a temperature of a fluid within the luminal organ.

17. The device of claim 14:
wherein the device is further surrounded by a second substantially or completely non-conductive coating, the second substantially or completely non-conductive coating defining the overall round cross-section; and
wherein the device, having the first substantially or completely non-conductive coating and the second substantially or completely non-conductive coating, has an overall round cross-section and an overall diameter between approximately 0.013" and approximately 0.050".

* * * * *